United States Patent
Ogawa et al.

[11] Patent Number: 6,096,736
[45] Date of Patent: Aug. 1, 2000

[54] BENZAZEPINE DERIVATIVES WITH VASOPRESSIN AGONISTIC ACTIVITY

[75] Inventors: Hidenori Ogawa; Kazumi Kondo, both of Tokushima-ken; Tomoichi Shinohara, Naruto; Keizo Kan, Tokushima; Yoshihisa Tanada; Muneaki Kurimura, both of Naruto; Seiji Morita, Tokushima; Minoru Uchida, Komatsushima; Toyoki Mori, Naruto; Michiaki Tominaga, Tokushima-ken; Yoichi Yabuuchi, Tokushima, all of Japan

[73] Assignee: Otsuka Pharmaceutical Company, Limited, Tokyo, Japan

[21] Appl. No.: 09/091,295

[22] PCT Filed: Dec. 13, 1996

[86] PCT No.: PCT/JP96/03652

§ 371 Date: Jun. 12, 1998

§ 102(e) Date: Jun. 12, 1998

[87] PCT Pub. No.: WO97/22591

PCT Pub. Date: Jun. 26, 1997

[30] Foreign Application Priority Data

Dec. 15, 1995 [JP] Japan ...................... 7-326136
Jul. 18, 1996 [JP] Japan ...................... 8-189500

[51] Int. Cl.[7] .......................... A61K 31/55; C07D 223/16
[52] U.S. Cl. ............................. 514/213; 540/593
[58] Field of Search ............................. 540/593; 514/213

[56] References Cited

U.S. PATENT DOCUMENTS 5,244,898  9/1993  Ogawa et al. .......................... 514/213
5,258,510 11/1993  Ogawa et al. .......................... 540/476
5,622,947  4/1997  Ogawa et al. .......................... 514/213

FOREIGN PATENT DOCUMENTS 0620 216 A1 10/1994 European Pat. Off. .
5-320135   3/1993  Japan .
WO 91/05549  5/1991  WIPO .
WO 94/01113  1/1994  WIPO .
WO 94/20473  9/1994  WIPO .
WO 95/18105  7/1995  WIPO .
WO 95/34540 12/1995  WIPO .

OTHER PUBLICATIONS

CAS structure search results of WO 94/08582 and WO 95/34540, 1999.

*Primary Examiner*—Mukund J. Shah
*Assistant Examiner*—Bruck Kifle
*Attorney, Agent, or Firm*—Finnegan, Henderson, Farabow, Garrett & Dunner, L.L.P.

[57] ABSTRACT

Novel benzazepine derivative of the formula [1]:

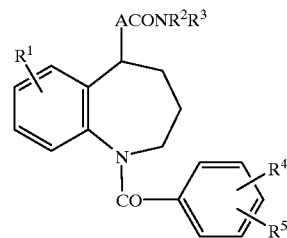

wherein $R^1$ is H or halogen, A is lower alkylene, $R^2$ and $R^3$ are the same or different and each H, lower alkoxy, lower alkyl having optionally a lower alkoxy substituent, etc., or $R^2$ and $R^3$ may combine together with the nitrogen to which they bond to form a 5- to 7-membered saturated heterocyclic group which may optionally be substituted by a lower alkyl, etc., $R^4$ is H, lower alkyl, OH, etc., $R^5$ is —$NHR^6$ ($R^6$ is lower alkyl) or pyrrolidinyl, or a salt thereof, which show excellent anti-vasopressin activity, oxytocin antagonistic activity and vasopressin agonistic activity, and are useful as a vasopressin antagonist, a vasopressin agonist and an oxytocin antagonist.

24 Claims, No Drawings

BENZAZEPINE DERIVATIVES WITH VASOPRESSIN AGONISTIC ACTIVITY

TECHNICAL FIELD

The present invention relates to novel benzazepine derivatives which have vasopressin antagonistic, vasopressin agonistic and oxytocin antagonistic activities and are useful as medicines.

BACKGROUND ART

Various benzazepine derivatives analogous to the compounds of the present invention have been known to have vasopressin antagonistic or oxytocin antagonistic activities. For example, it is described in U.S. Pat. No. 5,258,510 (=WO 91/05549), and WO 94/01113 that the benzazepine compounds of the following formula have vasopressin antagonistic and oxytocin antagonistic activities and further are useful as a medicament for the treatment of cataract.

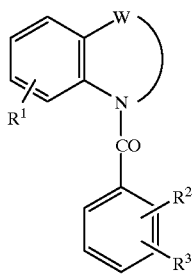

wherein $R^1$ is H, halogen, lower alkyl, amino, alkylamino, etc., $R^2$ is H, halogen, lower alkoxy, OH, etc., $R^3$ is —$NR^4R^5$ ($R^4$ is H, alkyl, etc., $R^5$ is substituted or unsubstituted benzoyl, phenylalkoxycarbonyl, alkanoyl, pyridylcarbonyl, etc.) or —$CONR^{11}R^{12}$, and W is —$(CH_2)_p$— (p is 3–5) or —CH=CH—$(CH_2)_q$— (q is 1–3) which may have 1–3 substituents selected from alkyl, hydroxyalkyl, alkoxycarbonyl, aminocarbonyloxy, aminocarbonylalkoxy, sulfoxyimino, —O—A—CO—$NR^{82}R^{83}$ (A being alkylene, $R^{82}$, $R^{83}$ being H, alkyl, hydroxyalkyl, pyridylalkyl, etc., or combine together with nitrogen atom to form heterocyclic groups), —$(CO)_n$—$NR^{14}R^{15}$, etc. However, these known compounds are different from the compounds of the present invention in the kinds of the substituents at 1- and 5-positions, and further in that the compounds of the present invention have further vasopressin agonistic activity.

It is also described in U.S. Pat. No. 5,244,898 (=European Patent 0514667) that the benzazepine compounds of the following formula have vasopressin antagonistic activity.

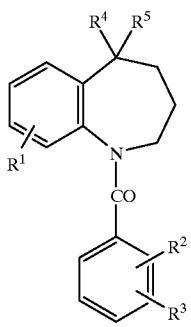

wherein $R^1$ is H, halogen, OH, alkanoyloxy, amino-alkoxy, etc., $R^2$ is H, alkyl, halogen, alkoxy, $R^3$ is substituted benzoylamino, $R^4$ is H, —$NR^6R^7$ ($R^6$, $R^7$ being H, alkyl, etc.), alkenyloxy, —O—A—CO—$NR^8R^9$ (A being alkylene, $R^8$, $R^9$ being H, alkyl, or combine together with nitrogen atom to form heterocyclic groups), —A—$CONR^{11}R^{12}$ (A being alkylene, and $R^{11}$, $R^{12}$ being H, alkyl, piperidinyl having optionally phenylalkyl substituent, etc., or combine together with nitrogen atom to form heterocyclic groups), —O—A—CO—$NR^{23}R^{24}$, etc., and $R^5$ is H or OH. However, these known compounds are different from the compounds of the present invention in the kinds of the substituents at 1-position, and further in that the compounds of the present invention have further vasopressin agonistic activity.

WO 94/08582 discloses also that benzazepine compounds the same as or very close to those of the above U.S. Pat. No. 5,244,898 have vasopressin antagonistic and oxytocin antagonistic activities, but these known compounds are different from the compounds of the present invention in the kinds of the substituents at 1-position, and further in that the compounds of the present invention have further vasopressin agonistic activity.

It is further disclosed in JP-A-5-320135 that the benzazepine compounds of the following formula have vasopressin antagonistic activities.

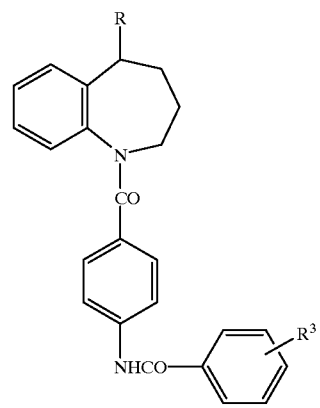

wherein R is formyl or =$CR^1R^2$ ($R^1$, $R^2$: one being H, another being alkoxy, alkoxycarbonyl, phenyl), and $R^3$ is H or alkyl. However, these known compounds are different from the compounds of the present invention in the kinds of the substituents at 1- and 5-positions, and further in that the compounds of the present invention have further vasopressin agonistic activity.

It is further disclosed in WO 94/20473 that the benzazepine compounds of the following formula have vasopressin antagonistic activity.

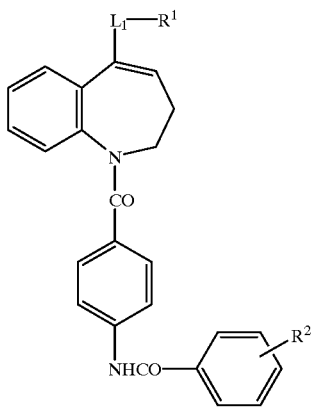

wherein $L_1$ is alkylene, $R^1$ is —COOH, —CONR$^6$R$^7$ ($R^6$, $R^7$ being H, alkyl, pyridyl-substituted alkyl), or —CO—heterocyclic group. However, these known compounds are different from the compounds of the present invention in the kinds of the substituents at 1-position, and further in that the compounds of the present invention have further vasopressin agonistic activity.

Furthermore, it is disclosed in EP 0620216 A1 that the benzazepine compounds of the following formula have vasopressin antagonistic activity.

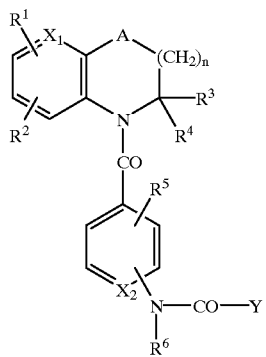

wherein $R^1$ is H or alkyl, $R^2$ is H, alkyl, halogen, alkoxy, etc., $R^3$ and $R^4$ are each H, alkyl, combine together to form =O, $R^5$ is H, halogen, NO$_2$, OH, alkyl, etc., $R^6$ is H, alkyl, or acyl, A is

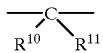

($R^{10}$ being H, $R^{11}$ being H, OH, alkyl-amino, alkyl, acyl-substituted alkyl) or —CR$^{12}$=CH— ($R^{12}$ being alkyl, acyl-substituted alkyl), etc., $X^1$, $X^2$ are CH or N, and Y is substituted or unsubstituted phenyl or naphthyl. However, these known compounds are different from the compounds of the present invention in the kinds of the substituents at 1- and 5-positions, and further in that the compounds of the present invention have further vasopressin agonistic activity.

Besides, it is described in WO 95/18105 that the indole compounds of the following formula have vasopressin antagonistic and/or agonistic activities and oxytocin antagonistic and/or agonistic activities.

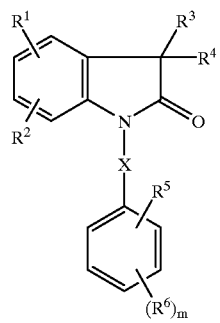

wherein $R^1$ and $R^2$ are each H, halogen, alkyl, alkoxy, CF$_3$, $R^3$ is alkyl, cycloalkyl, phenyl, etc., $R^4$ is —N$_3$, —NHN(CH$_3$)$_2$, —NR$^7$R$^8$, etc., $R^5$ is H, or the same as $R^6$, $R^6$ is halogen, alkyl, CF$_3$, CN, NO$_2$, —CONR$^9$R$^{11}$, etc., X is —SO$_2$— or —CH$_2$—, and m is 1 or 2, 3 or 4. However, these known compounds are different from the compounds of the present invention in the basic ring structure, that is, indole ring against the benzazepine ring.

DISCLOSURE OF THE INVENTION

An object of the present invention is to provide a novel benzazepine derivative which has never been disclosed in any literature, and has the following formula [1]:

[1]

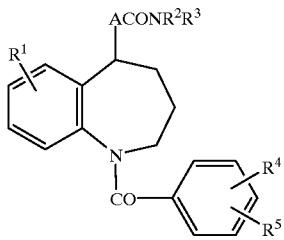

wherein $R^1$ is a hydrogen atom or a halogen atom,

A is a lower alkylene group, $R^2$ and $R^3$ are the same or different and each are a hydrogen atom, a lower alkoxy group, a lower alkyl group having optionally a lower alkoxy substituent, a hydroxy-substituted lower alkyl group, an amino-substituted lower alkyl group having optionally a lower alkyl substituent, a carbamoyl-substituted lower alkyl group, an adamantyl-substituted lower alkyl group, a lower alkylsulfonyl group, a thiazolyl group, a phenoxy-lower alkyl group, a pyridyl group, a pyridyl-lower alkyl group, an imidazolyl-lower alkyl group, a phenyl group having optionally a halogen substituent or an imidazolyl group having optionally a lower alkyl substituent, or $R^2$ and $R^3$ may combine together with the nitrogen atom to which they bond to form a 5- to 7-membered saturated heterocyclic group which may be intervened or not with another nitrogen atom or an oxygen atom, wherein said heterocyclic group may optionally be substituted by a lower alkyl group or a phenyl-lower alkyl group, $R^4$ is a hydrogen atom, a lower alkyl group, a hydroxy group, an amino group having optionally a lower alkanoyl substituent, a nitro group, a halogen atom or a lower alkoxy group, and $R^5$ is a group of the formula: —$NHR^6$ (wherein $R^6$ is a lower alkyl group) or a pyrrolidinyl group,
or a salt thereof.

Another object of the present invention is to provide a process for preparing the benzazepine derivative of the above formula [1].

Further object of the present invention is to provide a vasopressin antagonist, a vasopressin agonist and an oxytocin antagonist containing as an active ingredient the benzazepine derivative of the formula [1].

The present inventors have intensively studied and have found that the compounds of the formula [1] and a salt thereof have excellent vasopressin antagonistic activities, eacellent vasopressin agonistic activities and excellent oxytocin antagonistic activities, and that they are useful as a vasopressin antagonist, a vasopressin agonist and an oxytocin antagonist.

The vasopressin antagonist containing as an active ingredient the compound of the formula [1] of the present invention or a salt thereof shows excellent vasopressin antagonistic activities, for examples, vasodilating activity, hypotensive activity, activity of inhibiting saccharide release in liver, activity of inhibiting growth of mesangium cells, water diuretic activity, platelet agglutination inhibitory activity, inhibitory activity of vomiting, activity of promoting urea excretion, inhibitory activity on secretion of factor VIII, activity of promoting heart function, activity of inhibiting constriction of mesangium cells, inhibitory activity of production of saccharide in liver, inhibitory activity of aldosterone secretion, inhibitory activity of production of endothelin, regulation activity of renin secretion, memory regulation activity, thermoregulation activity, activity of regulating production of prostaglandin, and hence, it is useful as vasodilators, hypotensive agents, water diuretics, platelet agglutination inhibitors, promoters for urea excretion, agent for heart failure, agent for renal failure, etc., and can be used in the prophylaxis or treatment of hypertension, edema, ascites, heart failure, renal function disorder, vasopressin parasecretion syndrome, syndrome of inappropriate secretion of antidiuretic hormone (SIADH), hepatocirrhosis, hyponatremia, hypokalemia, diabetes, circulation disorder, motion sickness, water metabolism disorder, renal failure, various diseases associated with ischemic, and the like.

The vasopressin agonist containing as an active ingredient the compound [1] of the present invention or a salt thereof also shows vasopressin agonistic activities, for example, effects on various urinary disorders, polyuria or hemostatic disorders, and hence, it is useful in the prophylaxis or treatment of pollakisuria, diabetes insipidus, urine incontinence, enuresis, especially nocturnal enuresis, spontaneous hemorrhage, hemophilia, von Willebrand's disease, uremia, congenital and acquired platelet dysfunction, hemostatic derangement caused by surgical procedures or accidental trauma, or hepatocirrhosis.

In addition, the oxytocin antagonist containing as an active ingredient the compounds [1] of the present invention or a salt thereof also shows oxytocin antagonistic activities, for example, inhibitory effect on uterine smooth muscle constriction, inhibitory effect on milk secretion, inhibitory effect on synthesis and secretion of prostaglandin, and vasodilating activity, and hence, is useful in the protection or treatment of oxytocin-associated diseases, especially premature delivery, dysmenorrhea, endometritis, or in stopping labor preparatory to Caesarian delivery.

Specifically, the optically active benzazepine derivative [1] of the present invention shows especially excellent vasopressin agonistic activities, and is characteristic in its excellent efficiency of migration into the blood flow, absorbability and solubility.

Besides, the compounds of the present invention and salts thereof are characteristic in less side effects, and in prolonged action for a long time in living body.

Further, an optically active benzazpepine derivative of the formula [1-i]:

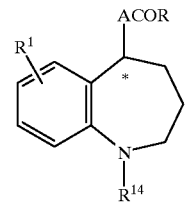

[1-i]

wherein $R^1$ and A are the same as defined above, $R^{14}$ is a hydrogen atom, a phenylsulfonyl group having optionally a lower alkyl substituent on the phenyl ring, or a group of the formula:

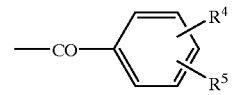

($R^4$ and $R^5$ are the same as defined above), and R is a hydroxy group or a group of the formula: —$NR^2R^3$ ($R^2$ and $R^3$ are the same as defined above), provided that when R is a group of the formula: —$NR^2R^3$, $R^{14}$ should not be a group of the formula:

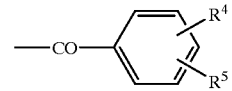

($R^4$ and $R^5$ are the same as defined above), is a very important intermediate for preparing the optically active compounds of the formula [1].

Each group in the above formula [1] specifically includes the following groups.

The "halogen atom" includes fluorine atom, chlorine atom, bromine atom, and iodine atom.

The "lower alkylene group" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkoxy group" includes a straight chain or branched chain alkoxy group having 1 to 6 carbon atoms, for example, methoxy, ethoxy, propoxy, isopropoxy, butoxy, t-butoxy, pentyloxy, hexyloxy, and the like.

The "lower alkyl group having optionally a lower alkoxy substituent" includes a straight chain or branched chain alkyl group having 1 to 6 carbon atoms, which may optionally be substituted by 1 to 3 straight chain or branched chain alkoxy groups having 1 to 6 carbon atoms, for example, methyl, ethyl, propyl, isopropyl, butyl, isobutyl, t-butyl, pentyl, hexyl, methoxymethyl, 3-methoxypropyl, ethoxymethyl, 2-methoxyethyl, 3-ethoxypropyl, 4-ethoxybutyl, 5-isopropoxypentyl, 6-propoxyhexyl, 1,1-dimethyl-2- butoxyethyl, 2-methyl-3-t-butoxypropyl, 2-pentyloxyethyl, hexyloxymethyl, and the like.

The "hydroxy-substituted lower alkyl group" includes a straight chain or branched chain alkyl group having 1 to 6 carbon atoms which is substituted by 1 to 3 hydroxy groups, for example, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, and the like.

The "amino-substituted lower alkyl group having optionally a lower alkyl substituent" includes a straight chain or branched chain alkyl group having 1 to 6 carbon atoms which is substituted by an amino group optionally being substituted by 1 to 2 straight chain or branched chain alkyl groups having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diethylaminoethyl, 2-dimethylaminoethyl, (N-ethyl-N-propylamino)methyl, 2-(N-methyl-N-hexylamino)ethyl, and the like.

The "carbamoyl-substituted lower alkyl group" includes a carbamoylalkyl group wherein the alkyl moiety is a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, and the like.

The "adamantyl-substituted lower alkyl group" includes an adamantylalkyl group wherein the alkyl moiety is a straight chain or branched chain alkyl group having 1 to 6 carbon atoms, for example, adamantylmethyl, 2-adamantylethyl, 1-adamantylethyl, 3-adamantylpropyl, 4-adamantylbutyl, 5-adamantylpentyl, 6-adamantylhexyl, 1,1-dimethyl-2-adamantylethyl, 2-methyl-3-adamantylpropyl, and the like.

The "lower alkylsulfonyl group" includes a straight chain or branched chain alkylsulfonyl group having 1 to 6 carbon atoms, for example, methylsulfonyl, ethylsulfonyl, propylsulfonyl, isopropylsulfonyl, butylsulfonyl, t-butylsulfonyl, pentylsulfonyl, hexylsulfonyl, and the like.

The "phenoxy-lower alkyl group" includes a straight chain or branched chain alkyl group having 1 to 6 carbon atoms which is substituted by 1 to 2 phenoxy groups, for example, phenoxymethyl, 2-phenoxyethyl, 1-phenoxyethyl, 3-phenoxypropyl, 4-phenoxybutyl, 5-phenoxypentyl, 6-phenoxyhexyl, 1,1-dimethyl-2-phenoxethyl, 2-methyl-3-phenoxypropyl, diphenoxymethyl, 2,2-diphenoxyethyl, and the like.

The "pyridyl-lower alkyl group" includes a pyridylalkyl group wherein the alkyl moiety is a straight chain or branched chain alkyl group having 1 to 6 carbon atoms, for example, (4-pyridyl)methyl, 1-(3-pyridyl)ethyl, 2-(2-pyridyl)ethyl, 3-(2-pyridyl)propyl, 4-(3-pyridyl)butyl, 5-(4-pyridyl)pentyl, 6-(2-pyridyl)hexyl, 1,1-dimethyl-2-(3-pyridyl)ethyl, 2-methyl-3-(4-pyridyl)propyl, and the like.

The "imidazolyl-lower alkyl group" includes an imidazolyl-alkyl group wherein the alkyl moiety is a straight chain or branched chain alkyl group having 1 to 6 carbon atoms, for example, (2-imidazolyl)methyl, 1-(4-imidazolyl) ethyl, 2-(5-imidazolyl)ethyl, 3-(1-imidazolyl)propyl, 4-(1-imidazolyl)butyl, 5-(2-imidazolyl)pentyl, 6-(1-imidazolyl) hexyl, 1,1-dimethyl-2-(4-imidazolyl)ethyl, 2-methyl-3-(5-imidazolyl)propyl, and the like.

The "phenyl group having optionally a halogen substituent" includes a phenyl group having optionally 1 to 3 halogen substituents, for example, phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 2,6-dichloro phenyl, 2,3-dichlorophenyl, 2,4-dichlorophenyl, 3,4-difluorophenyl, 3,5-dibromophenyl, 3,4,5-trichlorophenyl, and the like.

The "imidazolyl group having optionally a lower alkyl substituent" includes an imidazolyl group being optionally substituted by 1 to 3 straight chain or branched chain alkyl groups having 1 to 6 carbon atoms, for example, imidazolyl, 1-methylimidazolyl, 2-ethylimidazolyl, 4-propylimidazolyl, 5-butylimidazolyl, 1-pentylimidazolyl, 2-hexylimidazolyl, 1,5-dimethylimidazolyl, 1,4,5-trimethylimidazolyl, and the like.

The "5- to 7-membered saturated heterocyclic group which is formed by combining $R^2$ and $R^3$ with the nitrogen atom to which they bond, and may be intervened or not with another nitrogen atom or oxygen atom" includes pyrrolidinyl, piperidinyl, piperazinyl, morpholino, homopiperazinyl, and the like.

The "lower alkyl group" includes a straight chain or branched chain alkyl group having 1 to 6 carbon atoms, for example, methyl, ethyl, propyl, isopropyl, butyl, isobutyl, t-butyl, pentyl, hexyl, and the like.

The "phenyl-lower alkyl group" includes a straight chain or branched chain alkyl group having 1 to 6 carbon atoms which is substitued by 1 to 2 phenyl groups, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, diphenylmethyl, 2,2-diphenylethyl, and the like.

The "phenylsulfonyl group having optionally a lower alkyl substituent on the phenyl ring" includes a phenylsulfonyl group having optionally 1 to 3 straight chain or branched chain alkyl groups having 1 to 6 carbon atoms, for example, phenylsulfonyl, 2-methylphenylsulfonyl, 3-methylphenylsulfonyl, 4-methylphenylsulfonyl, 2-ethylphenylsulfonyl, 3-propylphenylsulfonyl, 4-butylphenylsulfonyl, 2-pentylphenylsulfonyl, 3-hexylphenylsulfonyl, 2,3-dimethylphenylsulfonyl, 2,4,6-trimethylphenylsulfonyl, and the like.

The "above mentioned heterocyclic group which is substituted by a lower alkyl group or a phenyl-lower alkyl group" includes the above mentioned heterocyclic groups which are substituted by 1 to 3 groups selected from a straight chain or branched chain alkyl group having 1 to 6 carbon atoms and a straight chain or branched chain alkyl group having 1 to 6 carbon atoms and being substituted by 1 to 2 phenyl groups, for example, 4-methylpiperazinyl, 3,4-dimethylpiperazinyl, 3-ethylpyrrolidinyl, 2-propylpyrrolidinyl, 1-methylpyrrolidinyl, 3,4,5-trimethylpiperidinyl, 4-butylpiperidinyl, 3-pentylmorpholino, 4-ethylhomopiperazinyl, 4-methylhomopiperazinyl, 4-hexylpiperazinyl, 4-diphenylmethylpiperazinyl, 4-benzylpiperazinyl, 3-methyl-4-benzylpiperazinyl, 3-(2-phenylethyl) pyrrolidinyl, 2-(1-phenylethyl)pyrrolidinyl, 4-(3-phenylpropyl)piperidinyl, 3-(4-phenylbutyl)morpholino, 3-(5-phenylpentyl)piperidinyl, 4-(6-phenylhexyl) piperazinyl, and the like.

The "lower alkanoyl group" includes a straight chain or branched chain alkanoyl group having 1 to 6 carbon atoms, for example, formyl, acetyl, propionyl, butyryl, isobutyryl, pentanoyl, t-butylcarbonyl, hexanoyl, and the like.

The "amino group having optionally a lower alkanoyl substituent" includes an amino group having optionally a straight chain or branched chain alkanoyl substituent having 1 to 6 carbon atoms, for example, amino, formylamino, acetylamino, propionylamino, butyrylamino, isobutyrylamino, pentanoylamino, t-butylcarbonylamino, hexanoylamino, and the like.

The benzazepine derivatives of the formula [1] of the present invention especially include the following compounds.

(1) The benzazepine derivative of the above formula [1] wherein $R^1$ is a hydrogen atom, both $R^2$ and $R^3$ are a hydrogen atom, $R^4$ is a hydrogen atom, a lower alkyl group, a hydroxy group, an amino group having optionally a lower alkanoyl substituent, a nitro group, a halogen atom or a lower alkoxy group, and $R^5$ is a group of the formula: —$NHR^6$ ($R^6$ is a lower alkyl group), or a salt thereof.

(2) The benzazepine derivative of the above formula [1] wherein $R^1$ is a hydrogen atom, both $R^2$ and $R^3$ are a lower alkoxy group, and $R^4$ and $R^5$ are the same as defined in the above compound (1), or a salt thereof.

(3) The benzazepine derivative of the above formula [1] wherein $R^1$ is a hydrogen atom, both $R^2$ and $R^3$ are a lower alkyl group having optionally a lower alkoxy substituent, and $R^4$ and $R^5$ are the same as defined in the above compound (1), or a salt thereof.

(4) The benzazepine derivative of the above formula [1] wherein $R^1$ is a hydrogen atom, both $R^2$ and $R^3$ are a hydroxy-substituted lower alkyl group, and $R^4$ and $R^5$ are the same as defined in the above compound (1), or a salt thereof.

(5) The benzazepine derivative of the above formula [1] wherein $R^1$ is a hydrogen atom, both $R^2$ and $R^3$ are an amino-substituted lower alkyl group having optionally a lower alkyl substituent, and $R^4$ and $R^5$ are the same as defined in the above compound (1), or a salt thereof.

(6) The benzazepine derivative of the above formula [1] wherein $R^1$ is a hydrogen atom, both $R^2$ and $R^3$ are a carbamoyl-substituted lower alkyl group, and $R^4$ and $R^5$ are the same as defined in the above compound (1), or a salt thereof.

(7) The benzazepine derivative of the above formula [1] wherein $R^1$ is a hydrogen atom, both $R^2$ and $R^3$ are an adamantyl-substituted lower alkyl group, and $R^4$ and $R^5$ are the same as defined in the above compound (1), or a salt thereof.

(8) The benzazepine derivative of the above formula [1] wherein $R^1$ is a hydrogen atom, both $R^2$ and $R^3$ are a lower alkylsulfonyl group, and $R^4$ and $R^5$ are the same as defined in the above compound (1), or a salt thereof.

(9) The benzazepine derivative of the above formula [1] wherein $R^1$ is a hydrogen atom, both $R^2$ and $R^3$ are a pyridyl group, and $R^4$ and $R^5$ are the same as defined in the above compound (1), or a salt thereof.

(10) The benzazepine derivative of the above formula [1] wherein $R^1$ is a hydrogen atom, both $R^2$ and $R^3$ are a pyridyl-lower alkyl group, and $R^4$ and $R^5$ are the same as defined in the above compound (1), or a salt thereof.

(11) The benzazepine derivative of the above formula [1] wherein $R^1$ is a hydrogen atom, both $R^2$ and $R^3$ are an imidazolyl-lower alkyl group, and $R^4$ and $R^5$ are the same as defined in the above compound (1), or a salt thereof.

(12) The benzazepine derivative of the above formula [1] wherein $R^1$ is a hydrogen atom, both $R^2$ and $R^3$ are a phenyl group having optionally a halogen substituent, and $R^4$ and $R^5$ are the same as defined in the above compound (1), or a salt thereof.

(13) The benzazepine derivative of the above formula [1] wherein $R^1$ is a hydrogen atom, both $R^2$ and $R^3$ are an imidazolyl group having optionally a lower alkyl substituent, and $R^4$ and $R^5$ are the same as defined in the above compound (1), or a salt thereof.

(14) The benzazepine derivative of the above formula [1] wherein $R^1$ is a hydrogen atom, $R^2$ and $R^3$ are different, and are a hydrogen atom or a lower alkoxy group, and $R^4$ and $R^5$ are the same as defined in the above compound (1), or a salt thereof.

(15) The benzazepine derivative of the above formula [1] wherein $R^1$ is a hydrogen atom, $R^2$ and $R^3$ are different, and are a hydrogen atom or a lower alkyl group having optionally a lower alkoxy substituent, and $R^4$ and $R^5$ are the same as defined in the above compound (1), or a salt thereof.

(16) The benzazepine derivative of the above formula [1] wherein $R^1$ is a hydrogen atom, $R^2$ and $R^3$ are different, and are a hydrogen atom or a hydroxy-substituted lower alkyl group, and $R^4$ and $R^5$ are the same as defined in the above compound (1), or a salt thereof.

(17) The benzazepine derivative of the above formula [1] wherein $R^1$ is a hydrogen atom, $R^2$ and $R^3$ are different, and are a hydrogen atom or an amino-substituted lower alkyl group having optionally a lower alkyl substituent, and $R^4$ and $R^5$ are the same as defined in the above compound (1), or a salt thereof.

(18) The benzazepine derivative of the above formula [1] wherein $R^1$ is a hydrogen atom, $R^2$ and $R^3$ are different, and are a hydrogen atom or a carbamoyl-substituted lower alkyl group, and $R^4$ and $R^5$ are the same as defined in the above compound (1), or a salt thereof.

(19) The benzazepine derivative of the above formula [1] wherein $R^1$ is a hydrogen atom, $R^2$ and $R^3$ are different, and are a hydrogen atom or a adamantyl-substituted lower alkyl group, and $R^4$ and $R^5$ are the same as defined in the above compound (1), or a salt thereof.

(20) The benzazepine derivative of the above formula [1] wherein $R^1$ is a hydrogen atom, $R^2$ and $R^3$ are different, and are a hydrogen atom or a lower alkylsulfonyl group, and $R^4$ and $R^5$ are the same as defined in the above compound (1), or a salt thereof.

(21) The benzazepine derivative of the above formula [1] wherein $R^1$ is a hydrogen atom, $R^2$ and $R^3$ are different, and are a hydrogen atom or a pyridyl group, and $R^4$ and $R^5$ are the same as defined in the above compound (1), or a salt thereof.

(22) The benzazepine derivative of the above formula [1] wherein $R^1$ is a hydrogen atom, $R^2$ and $R^3$ are different, and are a hydrogen atom or a pyridyl-lower alkyl group, and $R^4$ and $R^5$ are the same as defined in the above compound (1), or a salt thereof.

(23) The benzazepine derivative of the above formula [1] wherein $R^1$ is a hydrogen atom, $R^2$ and $R^3$ are different, and are a hydrogen atom or an imidazolyl-lower alkyl group, and $R^4$ and $R^5$ are the same as defined in the above compound (1), or a salt thereof.

(24) The benzazepine derivative of the above formula [1] wherein $R^1$ is a hydrogen atom, $R^2$ and $R^3$ are different, and are a hydrogen atom or a phenyl group having optionally a halogen substituent, and $R^4$ and $R^5$ are the same as defined in the above compound (1), or a salt thereof.

(25) The benzazepine derivative of the above formula [1] wherein $R^1$ is a hydrogen atom, $R^2$ and $R^3$ are different, and are a hydrogen atom or an imidazolyl group having optionally a lower alkyl substituent, and $R^4$ and $R^5$ are the same as defined in the above compound (1), or a salt thereof.

(26) The benzazepine derivative of the above formula [1] wherein $R^1$ is a hydrogen atom, $R^2$ and $R^3$ are different, and are a lower alkoxy group or a lower alkyl group having optionally a lower alkoxy substituent, and $R^4$ and $R^5$ are the same as defined in the above compound (1), or a salt thereof.

(27) The benzazepine derivative of the above formula [1] wherein $R^1$ is a hydrogen atom, $R^2$ and $R^3$ are different, and are a lower alkoxy group or a hydroxy-substituted lower alkyl group, and $R^4$ and $R^5$ are the same as defined in the above compound (1), or a salt thereof.

(28) The benzazepine derivative of the above formula [1] wherein $R^1$ is a hydrogen atom, $R^2$ and $R^3$ are different, and are a lower alkoxy group or an amino-substituted lower alkyl group having optionally a lower alkyl substituent, and $R^4$ and $R^5$ are the same as defined in the above compound (1), or a salt thereof.

(29) The benzazepine derivative of the above formula [1] wherein $R^1$ is a hydrogen atom, $R^2$ and $R^3$ are different, and are a lower alkoxy group or a carbamoyl-substituted lower alkyl group, and $R^4$ and $R^5$ are the same as defined in the above compound (1), or a salt thereof.

(30) The benzazepine derivative of the above formula [1] wherein $R^1$ is a hydrogen atom, $R^2$ and $R^3$ are different, and are a lower alkoxy group or an adamantyl-substituted lower alkyl group, and $R^4$ and $R^5$ are the same as defined in the above compound (1), or a salt thereof.

(31) The benzazepine derivative of the above formula [1] wherein $R^1$ is a hydrogen atom, $R^2$ and $R^3$ are different, and are a lower alkoxy group or a lower alkylsulfonyl group, and $R^4$ and $R^5$ are the same as defined in the above compound (1), or a salt thereof.

(32) The benzazepine derivative of the above formula [1] wherein $R^1$ is a hydrogen atom, $R^2$ and $R^3$ are different, and are a lower alkoxy group or a pyridyl group, and $R^4$ and $R^5$ are the same as defined in the above compound (1), or a salt thereof.

(33) The benzazepine derivative of the above formula [1] wherein $R^1$ is a hydrogen atom, $R^2$ and $R^3$ are different, and are a lower alkoxy group or a pyridyl-lower alkyl group, and $R^4$ and $R^5$ are the same as defined in the above compound (1), or a salt thereof.

(34) The benzazepine derivative of the above formula [1] wherein $R^1$ is a hydrogen atom, $R^2$ and $R^3$ are different, and are a lower alkoxy group or an imidazolyl-lower alkyl group, and $R^4$ and $R^5$ are the same as defined in the above compound (1), or a salt thereof.

(35) The benzazepine derivative of the above formula [1] wherein $R^1$ is a hydrogen atom, $R^2$ and $R^3$ are different, and are a lower alkoxy group or a phenyl group having optionally a halogen substituent, and $R^4$ and $R^5$ are the same as defined in the above compound (1), or a salt thereof.

(36) The benzazepine derivative of the above formula [1] wherein $R^1$ is a hydrogen atom, $R^2$ and $R^3$ are different, and are a lower alkoxy group or an imidazolyl group having optionally a lower alkyl substituent, and $R^4$ and $R^5$ are the same as defined in the above compound (1), or a salt thereof.

(37) The benzazepine derivative of the above formula [1] wherein $R^1$ is a hydrogen atom, $R^2$ and $R^3$ are different, and are a lower alkyl group having optionally a lower alkoxy substituent, or a hydroxy-substituted lower alkyl group, and $R^4$ and $R^5$ are the same as defined in the above compound (1), or a salt thereof.

(38) The benzazepine derivative of the above formula [1] wherein $R^1$ is a hydrogen atom, $R^2$ and $R^3$ are different, and are a lower alkyl group having optionally a lower alkoxy substituent, or an amino-substituted lower alkyl group having optionally a lower alkyl substituent, and $R^4$ and $R^5$ are the same as defined in the above compound (1), or a salt thereof.

(39) The benzazepine derivative of the above formula [1] wherein $R^1$ is a hydrogen atom, $R^2$ and $R^3$ are different, and are a lower alkyl group having optionally a lower alkoxy substituent, or a carbamoyl-substituted lower alkyl group, and $R^4$ and $R^5$ are the same as defined in the above compound (1), or a salt thereof.

(40) The benzazepine derivative of the above formula [1] wherein $R^1$ is a hydrogen atom, $R^2$ and $R^3$ are different, and are a lower alkyl group having optionally a lower alkoxy substituent, or an adamantyl-substituted lower alkyl group, and $R^4$ and $R^5$ are the same as defined in the above compound (1), or a salt thereof.

(41) The benzazepine derivative of the above formula [1] wherein $R^1$ is a hydrogen atom, $R^2$ and $R^3$ are different, and are a lower alkyl group having optionally a lower alkoxy substituent, or a lower alkylsulfonyl group, and $R^4$ and $R^5$ are the same as defined in the above compound (1), or a salt thereof.

(42) The benzazepine derivative of the above formula [1] wherein $R^1$ is a hydrogen atom, $R^2$ and $R^3$ are different, and are a lower alkyl group having optionally a lower alkoxy substituent, or a pyridyl group, and $R^4$ and $R^5$ are the same as defined in the above compound (1), or a salt thereof.

(43) The benzazepine derivative of the above formula [1] wherein $R^1$ is a hydrogen atom, $R^2$ and $R^3$ are different, and are a lower alkyl group having optionally a lower alkoxy substituent, or a pyridyl-lower alkyl group, and $R^4$ and $R^5$ are the same as defined in the above compound (1), or a salt thereof.

(44) The benzazepine derivative of the above formula [1] wherein $R^1$ is a hydrogen atom, $R^2$ and $R^3$ are different, and are a lower alkyl group having optionally a lower alkoxy substituent, or an imidazolyl-lower alkyl group, and $R^4$ and $R^5$ are the same as defined in the above compound (1), or a salt thereof.

(45) The benzazepine derivative of the above formula [1] wherein $R^1$ is a hydrogen atom, $R^2$ and $R^3$ are different, and are a lower alkyl group having optionally a lower alkoxy substituent, or a phenyl group having optionally a halogen substituent, and $R^4$ and $R^5$ are the same as defined in the above compound (1), or a salt thereof.

(46) The benzazepine derivative of the above formula [1] wherein $R^1$ is a hydrogen atom, $R^2$ and $R^3$ are different, and are a lower alkyl group having optionally a lower alkoxy substituent, or an imidazolyl group having optionally a lower alkyl substituent, and $R^4$ and $R^5$ are the same as defined in the above compound (1), or a salt thereof.

(47) The benzazepine derivative of the above formula [1] wherein $R^1$ is a hydrogen atom, $R^2$ and $R^3$ are different, and are a hydroxy-substituted lower alkyl group, or an amino-substituted lower alkyl group having optionally a lower alkyl substituent, and $R^4$ and $R^5$ are the same as defined in the above compound (1), or a salt thereof.

(48) The benzazepine derivative of the above formula [1] wherein $R^1$ is a hydrogen atom, $R^2$ and $R^3$ are different, and are a hydroxy-substituted lower alkyl group, or a carbamoyl-substituted lower alkyl group, and $R^4$ and $R^5$ are the same as defined in the above compound (1), or a salt thereof.

(49) The benzazepine derivative of the above formula [1] wherein $R^1$ is a hydrogen atom, $R^2$ and $R^3$ are different, and are a hydroxy-substituted lower alkyl group, or an adamantyl-substituted lower alkyl group, and $R^4$ and $R^5$ are the same as defined in the above compound (1), or a salt thereof.

(50) The benzazepine derivative of the above formula [1] wherein $R^1$ is a hydrogen atom, $R^2$ and $R^3$ are different, and are a hydroxy-substituted lower alkyl group, or a lower alkylsulfonyl group, and $R^4$ and $R^5$ are the same as defined in the above compound (1), or a salt thereof.

(51) The benzazepine derivative of the above formula [1] wherein $R^1$ is a hydrogen atom, $R^2$ and $R^3$ are different, and are a hydroxy-substituted lower alkyl group, or a pyridyl group, and $R^4$ and $R^5$ are the same as defined in the above compound (1), or a salt thereof.

(52) The benzazepine derivative of the above formula [1] wherein $R^1$ is a hydrogen atom, $R^2$ and $R^3$ are different, and are a hydroxy-substituted lower alkyl group, or a pyridyl-lower alkyl group, and $R^4$ and $R^5$ are the same as defined in the above compound (1), or a salt thereof.

(53) The benzazepine derivative of the above formula [1] wherein $R^1$ is a hydrogen atom, $R^2$ and $R^3$ are different, and are a hydroxy-substituted lower alkyl group, or an imidazolyl-lower alkyl group, and $R^4$ and $R^5$ are the same as defined in the above compound (1), or a salt thereof.

(54) The benzazepine derivative of the above formula [1] wherein $R^1$ is a hydrogen atom, $R^2$ and $R^3$ are different, and are a hydroxy-substituted lower alkyl group, or a phenyl group having optionally a halogen substituent, and $R^4$ and $R^5$ are the same as defined in the above compound (1), or a salt thereof.

(55) The benzazepine derivative of the above formula [1] wherein $R^1$ is a hydrogen atom, $R^2$ and $R^3$ are different, and are a hydroxy-substituted lower alkyl group, or an imidazolyl group having optionally a lower alkyl substituent, and $R^4$ and $R^5$ are the same as defined in the above compound (1), or a salt thereof.

(56) The benzazepine derivative of the above formula [1] wherein $R^1$ is a hydrogen atom, $R^2$ and $R^3$ are different, and are an amino-substituted lower alkyl group having optionally a lower alkyl substituent, or a carbamoyl-substituted lower alkyl group, and $R^4$ and $R^5$ are the same as defined in the above compound (1), or a salt thereof.

(57) The benzazepine derivative of the above formula [1] wherein $R^1$ is a hydrogen atom, $R^2$ and $R^3$ are different, and are an amino-substituted lower alkyl group having optionally a lower alkyl substituent, or an adamantyl-substituted lower alkyl group, and $R^4$ and $R^5$ are the same as defined in the above compound (1), or a salt thereof.

(58) The benzazepine derivative of the above formula [1] wherein $R^1$ is a hydrogen atom, $R^2$ and $R^3$ are different, and are an amino-substituted lower alkyl group having optionally a lower alkyl substituent, or a lower alkylsulfonyl group, and $R^4$ and $R^5$ are the same as defined in the above compound (1), or a salt thereof.

(59) The benzazepine derivative of the above formula [1] wherein $R^1$ is a hydrogen atom, $R^2$ and $R^3$ are different, and are an amino-substituted lower alkyl group having optionally a lower alkyl substituent, or a pyridyl group, and $R^4$ and $R^5$ are the same as defined in the above compound (1), or a salt thereof.

(60) The benzazepine derivative of the above formula [1] wherein $R^1$ is a hydrogen atom, $R^2$ and $R^3$ are different, and are an amino-substituted lower alkyl group having optionally a lower alkyl substituent, or a pyridyl-lower alkyl group, and $R^4$ and $R^5$ are the same as defined in the above compound (1), or a salt thereof.

(61) The benzazepine derivative of the above formula [1] wherein $R^1$ is a hydrogen atom, $R^2$ and $R^3$ are different, and are an amino-substituted lower alkyl group having optionally a lower alkyl substituent, or an imidazolyl-lower alkyl group, and $R^4$ and $R^5$ are the same as defined in the above compound (1), or a salt thereof.

(62) The benzazepine derivative of the above formula [1] wherein $R^1$ is a hydrogen atom, $R^2$ and $R^3$ are different, and are an amino-substituted lower alkyl group having optionally a lower alkyl substituent, or a phenyl group having optionally a halogen substituent, and $R^4$ and $R^5$ are the same as defined in the above compound (1), or a salt thereof.

(63) The benzazepine derivative of the above formula [1] wherein $R^1$ is a hydrogen atom, $R^2$ and $R^3$ are different, and are an amino-substituted lower alkyl group having optionally a lower alkyl substituent, or an imidazolyl group having optionally a lower alkyl substituent, and $R^4$ and $R^5$ are the same as defined in the above compound (1), or a salt thereof.

(64) The benzazepine derivative of the above formula [1] wherein $R^1$ is a hydrogen atom, $R^2$ and $R^3$ are different, and are a carbamoyl-substituted lower alkyl group, or an adamantyl-substituted lower alkyl group, and $R^4$ and $R^5$ are the same as defined in the above compound (1), or a salt thereof.

(65) The benzazepine derivative of the above formula [1] wherein $R^1$ is a hydrogen atom, $R^2$ and $R^3$ are different, and are a carbamoyl-substituted lower alkyl group, or a lower alkylsulfonyl group, and $R^4$ and $R^5$ are the same as defined in the above compound (1), or a salt thereof.

(66) The benzazepine derivative of the above formula [1] wherein $R^1$ is a hydrogen atom, $R^2$ and $R^3$ are different, and are a carbamoyl-substituted lower alkyl group, or a pyridyl group, and $R^4$ and $R^5$ are the same as defined in the above compound (1), or a salt thereof.

(67) The benzazepine derivative of the above formula [1] wherein $R^1$ is a hydrogen atom, $R^2$ and $R^3$ are different, and are a carbamoyl-substituted lower alkyl group, or a pyridyl-lower alkyl group, and $R^4$ and $R^5$ are the same as defined in the above compound (1), or a salt thereof.

(68) The benzazepine derivative of the above formula [1] wherein $R^1$ is a hydrogen atom, $R^2$ and $R^3$ are different, and are a carbamoyl-substituted lower alkyl group, or an imidazolyl-lower alkyl group, and $R^4$ and $R^5$ are the same as defined in the above compound (1), or a salt thereof.

(69) The benzazepine derivative of the above formula [1] wherein $R^1$ is a hydrogen atom, $R^2$ and $R^3$ are different, and are a carbamoyl-substituted lower alkyl group, or a phenyl group having optionally a halogen substituent, and $R^4$ and $R^5$ are the same as defined in the above compound (1), or a salt thereof.

(70) The benzazepine derivative of the above formula [1] wherein $R^1$ is a hydrogen atom, $R^2$ and $R^3$ are different, and are a carbamoyl-substituted lower alkyl group, or an imidazolyl group having optionally a lower alkyl substituent, and $R^4$ and $R^5$ are the same as defined in the above compound (1), or a salt thereof.

(71) The benzazepine derivative of the above formula [1] wherein $R^1$ is a hydrogen atom, $R^2$ and $R^3$ are different, and are an adamantyl-substituted lower alkyl group, or a lower alkylsulfonyl group, and $R^4$ and $R^5$ are the same as defined in the above compound (1), or a salt thereof.

(72) The benzazepine derivative of the above formula [1] wherein $R^1$ is a hydrogen atom, $R^2$ and $R^3$ are different, and are an adamantyl-substituted lower alkyl group, or a pyridyl group, and $R^4$ and $R^5$ are the same as defined in the above compound (1), or a salt thereof.

(73) The benzazepine derivative of the above formula [1] wherein $R^1$ is a hydrogen atom, $R^2$ and $R^3$ are different, and are an adamantyl-substituted lower alkyl group, or a pyridyl-lower alkyl group, and $R^4$ and $R^5$ are the same as defined in the above compound (1), or a salt thereof.

(74) The benzazepine derivative of the above formula [1] wherein $R^1$ is a hydrogen atom, $R^2$ and $R^3$ are different, and are an adamantyl-substituted lower alkyl group, or an imidazolyl-lower alkyl group, and $R^4$ and $R^5$ are the same as defined in the above compound (1), or a salt thereof.

(75) The benzazepine derivative of the above formula [1] wherein $R^1$ is a hydrogen atom, $R^2$ and $R^3$ are different, and are an adamantyl-substituted lower alkyl group, or a phenyl group having optionally a halogen substituent, and $R^4$ and $R^5$ are the same as defined in the above compound (1), or a salt thereof.
(76) The benzazepine derivative of the above formula [1] wherein $R^1$ is a hydrogen atom, $R^2$ and $R^3$ are different, and are an adamantyl-substituted lower alkyl group, or an imidazolyl group having optionally a lower alkyl substituent, and $R^4$ and $R^5$ are the same as defined in the above compound (1), or a salt thereof.
(77) The benzazepine derivative of the above formula [1] wherein $R^1$ is a hydrogen atom, $R^2$ and $R^3$ are different, and are a lower alkylsulfonyl group, or a pyridyl group, and $R^4$ and $R^5$ are the same as defined in the above compound (1), or a salt thereof.
(78) The benzazepine derivative of the above formula [1] wherein $R^1$ is a hydrogen atom, $R^2$ and $R^3$ are different, and are a lower alkylsulfonyl group, or a pyridyl-lower alkyl group, and $R^4$ and $R^5$ are the same as defined in the above compound (1), or a salt thereof.
(79) The benzazepine derivative of the above formula [1] wherein $R^1$ is a hydrogen atom, $R^2$ and $R^3$ are different, and are a lower alkylsulfonyl group, or an imidazolyl-lower alkyl group, and $R^4$ and $R^5$ are the same as defined in the above compound (1), or a salt thereof.
(80) The benzazepine derivative of the above formula [1] wherein $R^1$ is a hydrogen atom, $R^2$ and $R^3$ are different, and are a lower alkylsulfonyl group, or a phenyl group having optionally a halogen substituent, and $R^4$ and $R^5$ are the same as defined in the above compound (1), or a salt thereof.
(81) The benzazepine derivative of the above formula [1] wherein $R^1$ is a hydrogen atom, $R^2$ and $R^3$ are different, and are a lower alkylsulfonyl group, or an imidazolyl group having optionally a lower alkyl substituent, and $R^4$ and $R^5$ are the same as defined in the above compound (1), or a salt thereof.
(82) The benzazepine derivative of the above formula [1] wherein $R^1$ is a hydrogen atom, $R^2$ and $R^3$ are different, and are a pyridyl group, or a pyridyl-lower alkyl group, and $R^4$ and $R^5$ are the same as defined in the above compound (1), or a salt thereof.
(83) The benzazepine derivative of the above formula [1] wherein $R^1$ is a hydrogen atom, $R^2$ and $R^3$ are different, and are a pyridyl group, or an imidazolyl-lower alkyl group, and $R^4$ and $R^5$ are the same as defined in the above compound (1), or a salt thereof.
(84) The benzazepine derivative of the above formula [1] wherein $R^1$ is a hydrogen atom, $R^2$ and $R^3$ are different, and are a pyridyl group, or a phenyl group having optionally a halogen substituent, and $R^4$ and $R^5$ are the same as defined in the above compound (1), or a salt thereof.
(85) The benzazepine derivative of the above formula [1] wherein $R^1$ is a hydrogen atom, $R^2$ and $R^3$ are different, and are a pyridyl group, or an imidazolyl group having optionally a lower alkyl substituent, and $R^4$ and $R^5$ are the same as defined in the above compound (1), or a salt thereof.
(86) The benzazepine derivative of the above formula [1] wherein $R^1$ is a hydrogen atom, $R^2$ and $R^3$ are different, and are a pyridyl-lower alkyl group, or an imidazolyl-lower alkyl group, and $R^4$ and $R^5$ are the same as defined in the above compound (1), or a salt thereof.
(87) The benzazepine derivative of the above formula [1] wherein $R^1$ is a hydrogen atom, $R^2$ and $R^3$ are different, and are a pyridyl-lower alkyl group, or a phenyl group having optionally a halogen substituent, and $R^4$ and $R^5$ are the same as defined in the above compound (1), or a salt thereof.
(88) The benzazepine derivative of the above formula [1] wherein $R^1$ is a hydrogen atom, $R^2$ and $R^3$ are different, and are a pyridyl-lower alkyl group, or an imidazolyl group having optionally a lower alkyl substituent, and $R^4$ and $R^5$ are the same as defined in the above compound (1), or a salt thereof.
(89) The benzazepine derivative of the above formula [1] wherein $R^1$ is a hydrogen atom, $R^2$ and $R^3$ are different, and are an imidazolyl-lower alkyl group, or a phenyl group having optionally a halogen substituent, and $R^4$ and $R^5$ are the same as defined in the above compound (1), or a salt thereof.
(90) The benzazepine derivative of the above formula [1] wherein $R^1$ is a hydrogen atom, $R^2$ and $R^3$ are different, and are an imidazolyl-lower alkyl group, or an imidazolyl group having optionally a lower alkyl substituent, and $R^4$ and $R^5$ are the same as defined in the above compound (1), or a salt thereof.
(91) The benzazepine derivative of the above formula [1] wherein $R^1$ is a hydrogen atom, $R^2$ and $R^3$ are different, and are a phenyl group having optionally a halogen substituent, or an imidazolyl group having optionally a lower alkyl substituent, and $R^4$ and $R^5$ are the same as defined in the above compound (1), or a salt thereof.
(92) The benzazepine derivative of the above formula [1] wherein $R^1$ is a hydrogen atom, $R^2$ and $R^3$ combine together with the nitrogen atom to which they bond to form a 5- to 7-membered saturated heterocyclic group which may be intervened or not with another nitrogen atom or an oxygen atom, wherein said heterocyclic group may optionally be substituted by a lower alkyl group or a phenyl-lower alkyl group, and $R^4$ and $R^5$ are the same as defined in the above compound (1), or a salt thereof.
(93) The benzazepine derivative of the above formula [1] wherein $R^1$, $R^2$, $R^3$ and $R^4$ are the same as defined in the above compound (1), and $R^5$ is a pyrrolidinyl group, or a salt thereof.
(94) The benzazepine derivative of the above formula [1] wherein $R^1$, $R^2$, $R^3$ and $R^4$ are the same as defined in the above compound (2), and $R^5$ is a pyrrolidinyl group, or a salt thereof.
(95) The benzazepine derivative of the above formula [1] wherein $R^1$, $R^2$, $R^3$ and $R^4$ are the same as defined in the above compound (3), and $R^5$ is a pyrrolidinyl group, or a salt thereof.
(96) The benzazepine derivative of the above formula [1] wherein $R^1$, $R^2$, $R^3$ and $R^4$ are the same as defined in the above compound (4), and $R^5$ is a pyrrolidinyl group, or a salt thereof.
(97) The benzazepine derivative of the above formula [1] wherein $R^1$, $R^2$, $R^3$ and $R^4$ are the same as defined in the above compound (5), and $R^5$ is a pyrrolidinyl group, or a salt thereof.
(98) The benzazepine derivative of the above formula [1] wherein $R^1$, $R^2$, $R^3$ and $R^4$ are the same as defined in the above compound (6), and $R^5$ is a pyrrolidinyl group, or a salt thereof.
(99) The benzazepine derivative of the above formula [1] wherein $R^1$, $R_2$, $R^3$ and $R^4$ are the same as defined in the above compound (7), and $R^5$ is a pyrrolidinyl group, or a salt thereof.
(100) The benzazepine derivative of the above formula [1] wherein $R^1$, $R^2$, $R^3$ and $R^4$ are the same as defined in the above compound (8), and $R^5$ is a pyrrolidinyl group, or a salt thereof.
(101) The benzazepine derivative of the above formula [1] wherein $R^1$, $R^2$, $R^3$ and $R^4$ are the same as defined in the above compound (9), and $R^5$ is a pyrrolidinyl group, or a salt thereof.

(102) The benzazepine derivative of the above formula [1] wherein $R^1$, $R^2$, $R^3$ and $R^4$ are the same as defined in the above compound (10), and $R^5$ is a pyrrolidinyl group, or a salt thereof.
(103) The benzazepine derivative of the above formula [1] wherein $R^1$, $R^2$, $R^3$ and $R^4$ are the same as defined in the above compound (11), and $R^5$ is a pyrrolidinyl group, or a salt thereof.
(104) The benzazepine derivative of the above formula [1] wherein $R^1$, $R^2$, $R^3$ and $R^4$ are the same as defined in the above compound (12), and $R^5$ is a pyrrolidinyl group, or a salt thereof.
(105) The benzazepine derivative of the above formula [1] wherein $R^1$, $R^2$, $R^3$ and $R^4$ are the same as defined in the above compound (13), and $R^5$ is a pyrrolidinyl group, or a salt thereof.
(106) The benzazepine derivative of the above formula [1] wherein $R^1$, $R^2$, $R^3$ and $R^4$ are the same as defined in the above compound (14), and $R^5$ is a pyrrolidinyl group, or a salt thereof.
(107) The benzazepine derivative of the above formula [1] wherein $R^1$, $R^2$, $R^3$ and $R^4$ are the same as defined in the above compound (15), and $R^5$ is a pyrrolidinyl group, or a salt thereof.
(108) The benzazepine derivative of the above formula [1] wherein $R^1$, $R^2$, $R^3$ and $R^4$ are the same as defined in the above compound (16), and $R^5$ is a pyrrolidinyl group, or a salt thereof.
(109) The benzazepine derivative of the above formula [1] wherein $R^1$, $R^2$, $R^3$ and $R^4$ are the same as defined in the above compound (17), and $R^5$ is a pyrrolidinyl group, or a salt thereof.
(110) The benzazepine derivative of the above formula [1] wherein $R^1$, $R^2$, $R^3$ and $R^4$ are the same as defined in the above compound (18), and $R^5$ is a pyrrolidinyl group, or a salt thereof.
(111) The benzazepine derivative of the above formula [1] wherein $R^1$, $R^2$, $R^3$ and $R^4$ are the same as defined in the above compound (19), and $R^5$ is a pyrrolidinyl group, or a salt thereof.
(112) The benzazepine derivative of the above formula [1] wherein $R^1$, $R^2$, $R^3$ and $R^4$ are the same as defined in the above compound (20), and $R^5$ is a pyrrolidinyl group, or a salt thereof.
(113) The benzazepine derivative of the above formula [1] wherein $R^1$, $R^2$, $R^3$ and $R^4$ are the same as defined in the above compound (21), and $R^5$ is a pyrrolidinyl group, or a salt thereof.
(114) The benzazepine derivative of the above formula [1] wherein $R^1$, $R^2$, $R^3$ and $R^4$ are the same as defined in the above compound (22), and $R^5$ is a pyrrolidinyl group, or a salt thereof.
(115) The benzazepine derivative of the above formula [1] wherein $R^1$, $R^2$, $R^3$ and $R^4$ are the same as defined in the above compound (23), and $R^5$ is a pyrrolidinyl group, or a salt thereof.
(116) The benzazepine derivative of the above formula [1] wherein $R^1$, $R^2$, $R^3$ and $R^4$ are the same as defined in the above compound (24), and $R^5$ is a pyrrolidinyl group, or a salt thereof.
(117) The benzazepine derivative of the above formula [1] wherein $R^1$, $R^2$, $R^3$ and $R^4$ are the same as defined in the above compound (25), and $R^5$ is a pyrrolidinyl group, or a salt thereof.
(118) The benzazepine derivative of the above formula [1] wherein $R^1$, $R^2$, $R^3$ and $R^4$ are the same as defined in the above compound (26), and $R^5$ is a pyrrolidinyl group, or a salt thereof.
(119) The benzazepine derivative of the above formula [1] wherein $R^1$, $R^2$, $R^3$ and $R^4$ are the same as defined in the above compound (27), and $R^5$ is a pyrrolidinyl group, or a salt thereof.
(120) The benzazepine derivative of the above formula [1] wherein $R^1$, $R^2$, $R^3$ and $R^4$ are the same as defined in the above compound (28), and $R^5$ is a pyrrolidinyl group, or a salt thereof.
(121) The benzazepine derivative of the above formula [1] wherein $R^1$, $R^2$, $R^3$ and $R^4$ are the same as defined in the above compound (29), and $R^5$ is a pyrrolidinyl group, or a salt thereof.
(122) The benzazepine derivative of the above formula [1] wherein $R^1$, $R^2$, $R^3$ and $R^4$ are the same as defined in the above compound (30), and $R^5$ is a pyrrolidinyl group, or a salt thereof.
(123) The benzazepine derivative of the above formula [1] wherein $R^1$, $R^2$, $R^3$ and $R^4$ are the same as defined in the above compound (31), and $R^5$ is a pyrrolidinyl group, or a salt thereof.
(124) The benzazepine derivative of the above formula [1] wherein $R^1$, $R^2$, $R^3$ and $R^4$ are the same as defined in the above compound (32), and $R^5$ is a pyrrolidinyl group, or a salt thereof.
(125) The benzazepine derivative of the above formula [1] wherein $R^1$, $R^2$, $R^3$ and $R^4$ are the same as defined in the above compound (33), and $R^5$ is a pyrrolidinyl group, or a salt thereof.
(126) The benzazepine derivative of the above formula [1] wherein $R^1$, $R^2$, $R^3$ and $R^4$ are the same as defined in the above compound (34), and $R^5$ is a pyrrolidinyl group, or a salt thereof.
(127) The benzazepine derivative of the above formula [1] wherein $R^1$, $R^2$, $R^3$ and $R^4$ are the same as defined in the above compound (35), and $R^5$ is a pyrrolidinyl group, or a salt thereof.
(128) The benzazepine derivative of the above formula [1] wherein $R^1$, $R^2$, $R^3$ and $R^4$ are the same as defined in the above compound (36), and $R^5$ is a pyrrolidinyl group, or a salt thereof.
(129) The benzazepine derivative of the above formula [1] wherein $R^1$, $R^2$, $R^3$ and $R^4$ are the same as defined in the above compound (37), and $R^5$ is a pyrrolidinyl group, or a salt thereof.
(130) The benzazepine derivative of the above formula [1] wherein $R^1$, $R^2$, $R^3$ and $R^4$ are the same as defined in the above compound (38), and $R^5$ is a pyrrolidinyl group, or a salt thereof.
(131) The benzazepine derivative of the above formula [1] wherein $R^1$, $R^2$, $R^3$ and $R^4$ are the same as defined in the above compound (39), and $R^5$ is a pyrrolidinyl group, or a salt thereof.
(132) The benzazepine derivative of the above formula [1] wherein $R^1$, $R^2$, $R^3$ and $R^4$ are the same as defined in the above compound (40), and $R^5$ is a pyrrolidinyl group, or a salt thereof.
(133) The benzazepine derivative of the above formula [1] wherein $R^1$, $R^2$, $R^3$ and $R^4$ are the same as defined in the above compound (41), and $R^5$ is a pyrrolidinyl group, or a salt thereof.
(134) The benzazepine derivative of the above formula [1] wherein $R^1$, $R^2$, $R^3$ and $R^4$ are the same as defined in the above compound (42), and $R^5$ is a pyrrolidinyl group, or a salt thereof.
(135) The benzazepine derivative of the above formula [1] wherein $R^1$, $R^2$, $R^3$ and $R^4$ are the same as defined in the above compound (43), and $R^5$ is a pyrrolidinyl group, or a salt thereof.

(136) The benzazepine derivative of the above formula [1] wherein $R^1$, $R^2$, $R^3$ and $R^4$ are the same as defined in the above compound (44), and $R^5$ is a pyrrolidinyl group, or a salt thereof.
(137) The benzazepine derivative of the above formula [1] wherein $R^1$, $R^2$, $R^3$ and $R^4$ are the same as defined in the above compound (45), and $R^5$ is a pyrrolidinyl group, or a salt thereof.
(138) The benzazepine derivative of the above formula [1] wherein $R^1$, $R^2$, $R^3$ and $R^4$ are the same as defined in the above compound (46), and $R^5$ is a pyrrolidinyl group, or a salt thereof.
(139) The benzazepine derivative of the above formula [1] wherein $R^1$, $R^2$, $R^3$ and $R^4$ are the same as defined in the above compound (47), and $R^5$ is a pyrrolidinyl group, or a salt thereof.
(140) The benzazepine derivative of the above formula [1] wherein $R^1$, $R^2$, $R^3$ and $R^4$ are the same as defined in the above compound (48), and $R^5$ is a pyrrolidinyl group, or a salt thereof.
(141) The benzazepine derivative of the above formula [1] wherein $R^1$, $R^2$, $R^3$ and $R^4$ are the same as defined in the above compound (49), and $R^5$ is a pyrrolidinyl group, or a salt thereof.
(142) The benzazepine derivative of the above formula [1] wherein $R^1$, $R^2$, $R^3$ and $R^4$ are the same as defined in the above compound (50), and $R^5$ is a pyrrolidinyl group, or a salt thereof.
(143) The benzazepine derivative of the above formula [1] wherein $R^1$, $R^2$, $R^3$ and $R^4$ are the same as defined in the above compound (51), and $R^5$ is a pyrrolidinyl group, or a salt thereof.
(144) The benzazepine derivative of the above formula [1] wherein $R^1$, $R^2$, $R^3$ and $R^4$ are the same as defined in the above compound (52), and $R^5$ is a pyrrolidinyl group, or a salt thereof.
(145) The benzazepine derivative of the above formula [1] wherein $R^1$, $R^2$, $R^3$ and $R^4$ are the same as defined in the above compound (53), and $R^5$ is a pyrrolidinyl group, or a salt thereof.
(146) The benzazepine derivative of the above formula [1] wherein $R^1$, $R^2$, $R^3$ and $R^4$ are the same as defined in the above compound (54), and $R^5$ is a pyrrolidinyl group, or a salt thereof.
(147) The benzazepine derivative of the above formula [1] wherein $R^1$, $R^2$, $R^3$ and $R^4$ are the same as defined in the above compound (55), and $R^5$ is a pyrrolidinyl group, or a salt thereof.
(148) The benzazepine derivative of the above formula [1] wherein $R^1$, $R^2$, $R^3$ and $R^4$ are the same as defined in the above compound (56), and $R^5$ is a pyrrolidinyl group, or a salt thereof.
(149) The benzazepine derivative of the above formula [1] wherein $R^1$, $R^2$, $R^3$ and $R^4$ are the same as defined in the above compound (57), and $R^5$ is a pyrrolidinyl group, or a salt thereof.
(150) The benzazepine derivative of the above formula [1] wherein $R^1$, $R^2$, $R^3$ and $R^4$ are the same as defined in the above compound (58), and $R^5$ is a pyrrolidinyl group, or a salt thereof.
(151) The benzazepine derivative of the above formula [1] wherein $R^1$, $R^2$, $R^3$ and $R^4$ are the same as defined in the above compound (59), and $R^5$ is a pyrrolidinyl group, or a salt thereof.
(152) The benzazepine derivative of the above formula [1] wherein $R^1$, $R^2$, $R^3$ and $R^4$ are the same as defined in the above compound (60), and $R^5$ is a pyrrolidinyl group, or a salt thereof.
(153) The benzazepine derivative of the above formula [1] wherein $R^1$, $R^2$, $R^3$ and $R^4$ are the same as defined in the above compound (61), and $R^5$ is a pyrrolidinyl group, or a salt thereof.
(154) The benzazepine derivative of the above formula [1] wherein $R^1$, $R^2$, $R^3$ and $R^4$ are the same as defined in the above compound (62), and $R^5$ is a pyrrolidinyl group, or a salt thereof.
(155) The benzazepine derivative of the above formula [1] wherein $R^1$, $R^2$, $R^3$ and $R^4$ are the same as defined in the above compound (63), and $R^5$ is a pyrrolidinyl group, or a salt thereof.
(156) The benzazepine derivative of the above formula [1] wherein $R^1$, $R^2$, $R^3$ and $R^4$ are the same as defined in the above compound (64), and $R^5$ is a pyrrolidinyl group, or a salt thereof.
(157) The benzazepine derivative of the above formula [1] wherein $R^1$, $R^2$, $R^3$ and $R^4$ are the same as defined in the above compound (65), and $R^5$ is a pyrrolidinyl group, or a salt thereof.
(158) The benzazepine derivative of the above formula [1] wherein $R^1$, $R^2$, $R^3$ and $R^4$ are the same as defined in the above compound (66), and $R^5$ is a pyrrolidinyl group, or a salt thereof.
(159) The benzazepine derivative of the above formula [1 ] wherein $R^1$, $R^2$, $R^3$ and $R^4$ are the same as defined in the above compound (67), and $R^5$ is a pyrrolidinyl group, or a salt thereof.
(160) The benzazepine derivative of the above formula [1] wherein $R^1$, $R^2$, $R^3$ and $R^4$ are the same as defined in the above compound (68), and $R^5$ is a pyrrolidinyl group, or a salt thereof.
(161) The benzazepine derivative of the above formula [1] wherein $R^1$, $R^2$, $R^3$ and $R^4$ are the same as defined in the above compound (69), and $R^5$ is a pyrrolidinyl group, or a salt thereof.
(162) The benzazepine derivative of the above formula [1] wherein $R^1$, $R^2$, $R^3$ and $R^4$ are the same as defined in the above compound (70), and $R^5$ is a pyrrolidinyl group, or a salt thereof.
(163) The benzazepine derivative of the above formula [1] wherein $R^1$, $R^2$, $R^3$ and $R^4$ are the same as defined in the above compound (71), and $R^5$ is a pyrrolidinyl group, or a salt thereof.
(164) The benzazepine derivative of the above formula [1] wherein $R^1$, $R^2$, $R^3$ and $R^4$ are the same as defined in the above compound (72), and $R^5$ is a pyrrolidinyl group, or a salt thereof.
(165) The benzazepine derivative of the above formula [1] wherein $R^1$, $R^2$, $R^3$ and $R^4$ are the same as defined in the above compound (73), and $R^5$ is a pyrrolidinyl group, or a salt thereof.
(166) The benzazepine derivative of the above formula [1] wherein $R^1$, $R^2$, $R^3$ and $R^4$ are the same as defined in the above compound (74), and $R^5$ is a pyrrolidinyl group, or a salt thereof.
(167) The benzazepine derivative of the above formula [1] wherein $R^1$, $R^2$, $R^3$ and $R^4$ are the same as defined in the above compound (75), and $R^5$ is a pyrrolidinyl group, or a salt thereof.
(168) The benzazepine derivative of the above formula [1] wherein $R^1$, $R^2$, $R^3$ and $R^4$ are the same as defined in the above compound (76), and $R^5$ is a pyrrolidinyl group, or a salt thereof.
(169) The benzazepine derivative of the above formula [1] wherein $R^1$, $R^2$, $R^3$ and $R^4$ are the same as defined in the above compound (77), and $R^5$ is a pyrrolidinyl group, or a salt thereof.

(170) The benzazepine derivative of the above formula [1] wherein $R^1$, $R^2$, $R^3$ and $R^4$ are the same as defined in the above compound (78), and $R^5$ is a pyrrolidinyl group, or a salt thereof.
(171) The benzazepine derivative of the above formula [1] wherein $R^1$, $R^2$, $R^3$ and $R^4$ are the same as defined in the above compound (79), and $R^5$ is a pyrrolidinyl group, or a salt thereof.
(172) The benzazepine derivative of the above formula [1] wherein $R^1$, $R^2$, $R^3$ and $R^4$ are the same as defined in the above compound (80), and $R^5$ is a pyrrolidinyl group, or a salt thereof.
(173) The benzazepine derivative of the above formula [1] wherein $R^1$, $R^2$, $R^3$ and $R^4$ are the same as defined in the above compound (81), and $R^5$ is a pyrrolidinyl group, or a salt thereof.
(174) The benzazepine derivative of the above formula [1] wherein $R^1$, $R^2$, $R^3$ and $R^4$ are the same as defined in the above compound (82), and $R^5$ is a pyrrolidinyl group, or a salt thereof.
(175) The benzazepine derivative of the above formula [1] wherein $R^1$, $R^2$, $R^3$ and $R^4$ are the same as defined in the above compound (83), and $R^5$ is a pyrrolidinyl group, or a salt thereof.
(176) The benzazepine derivative of the above formula [1] wherein $R^1$, $R^2$, $R^3$ and $R^4$ are the same as defined in the above compound (84), and $R^5$ is a pyrrolidinyl group, or a salt thereof.
(177) The benzazepine derivative of the above formula [1] wherein $R^1$, $R^2$, $R^3$ and $R^4$ are the same as defined in the above compound (85), and $R^5$ is a pyrrolidinyl group, or a salt thereof.
(178) The benzazepine derivative of the above formula [1] wherein $R^1$, $R^2$, $R^3$ and $R^4$ are the same as defined in the above compound (86), and $R^5$ is a pyrrolidinyl group, or a salt thereof.
(179) The benzazepine derivative of the above formula [1] wherein $R^1$, $R^2$, $R^3$ and $R^4$ are the same as defined in the above compound (87), and $R^5$ is a pyrrolidinyl group, or a salt thereof.
(180) The benzazepine derivative of the above formula [1] wherein $R^1$, $R^2$, $R^3$ and $R^4$ are the same as defined in the above compound (88), and $R^5$ is a pyrrolidinyl group, or a salt thereof.
(181) The benzazepine derivative of the above formula [1] wherein $R^1$, $R^2$, $R^3$ and $R^4$ are the same as defined in the above compound (89), and $R^5$ is a pyrrolidinyl group, or a salt thereof.
(182) The benzazepine derivative of the above formula [1] wherein $R^1$, $R^2$, $R^3$ and $R^4$ are the same as defined in the above compound (90), and $R^5$ is a pyrrolidinyl group, or a salt thereof.
(183) The benzazepine derivative of the above formula [1] wherein $R^1$, $R^2$, $R^3$ and $R^4$ are the same as defined in the above compound (91), and $R^5$ is a pyrrolidinyl group, or a salt thereof.
(184) The benzazepine derivative of the above formula [1] wherein $R^1$, $R^2$, $R^3$ and $R^4$ are the same as defined in the above compound (92), and $R^5$ is a pyrrolidinyl group, or a salt thereof.
(185) The benzazepine derivative of the above formula [1] wherein $R^2$, $R^3$, $R^4$ and $R^5$ are the same as defined in the above compound (1), and $R^1$ is a halogen atom, or a salt thereof.
(186) The benzazepine derivative of the above formula [1] wherein $R^2$, $R^3$, $R^4$ and $R^5$ are the same as defined in the above compound (2), and $R^1$ is a halogen atom, or a salt thereof.
(187) The benzazepine derivative of the above formula [1] wherein $R^2$, $R^3$, $R^4$ and $R^5$ are the same as defined in the above compound (3), and $R^1$ is a halogen atom, or a salt thereof.
(188) The benzazepine derivative of the above formula [1] wherein $R^2$, $R^3$, $R^4$ and $R^5$ are the same as defined in the above compound (4), and $R^1$ is a halogen atom, or a salt thereof.
(189) The benzazepine derivative of the above formula [1] wherein $R^2$, $R^3$, $R^4$ and $R^5$ are the same as defined in the above compound (5), and $R^1$ is a halogen atom, or a salt thereof.
(190) The benzazepine derivative of the above formula [1] wherein $R^2$, $R^3$, $R^4$ and $R^5$ are the same as defined in the above compound (6), and $R^1$ is a halogen atom, or a salt thereof.
(191) The benzazepine derivative of the above formula [1] wherein $R^2$, $R^3$, $R^4$ and $R^5$ are the same as defined in the above compound (7), and $R^1$ is a halogen atom, or a salt thereof.
(192) The benzazepine derivative of the above formula [1] wherein $R^2$, $R^3$, $R^4$ and $R^5$ are the same as defined in the above compound (8), and $R^1$ is a halogen atom, or a salt thereof.
(193) The benzazepine derivative of the above formula [1] wherein $R^2$, $R^3$, $R^4$ and $R^5$ are the same as defined in the above compound (9), and $R^1$ is a halogen atom, or a salt thereof.
(194) The benzazepine derivative of the above formula [1] wherein $R^2$, $R^3$, $R^4$ and $R^5$ are the same as defined in the above compound (10), and $R^1$ is a halogen atom, or a salt thereof.
(195) The benzazepine derivative of the above formula [1] wherein $R^2$, $R^3$, $R^4$ and $R^5$ are the same as defined in the above compound (11), and $R^1$ is a halogen atom, or a salt thereof.
(196) The benzazepine derivative of the above formula [1] wherein $R^2$, $R^3$, $R^4$ and $R^5$ are the same as defined in the above compound (12), and $R^1$ is a halogen atom, or a salt thereof.
(197) The benzazepine derivative of the above formula [1] wherein $R^2$, $R^3$, $R^4$ and $R^5$ are the same as defined in the above compound (13), and $R^1$ is a halogen atom, or a salt thereof.
(198) The benzazepine derivative of the above formula [1] wherein $R^2$, $R^3$, $R^4$ and $R^5$ are the same as defined in the above compound (14), and $R^1$ is a halogen atom, or a salt thereof.
(199) The benzazepine derivative of the above formula [1] wherein $R^2$, $R^3$, $R^4$ and $R^5$ are the same as defined in the above compound (15), and $R^1$ is a halogen atom, or a salt thereof.
(200) The benzazepine derivative of the above formula [1] wherein $R^2$, $R^3$, $R^4$ and $R^5$ are the same as defined in the above compound (16), and $R^1$ is a halogen atom, or a salt thereof.
(201) The benzazepine derivative of the above formula [1] wherein $R^2$, $R^3$, $R^4$ and $R^5$ are the same as defined in the above compound (17), and $R^1$ is a halogen atom, or a salt thereof.
(202) The benzazepine derivative of the above formula [1] wherein $R^2$, $R^3$, $R^4$ and $R^5$ are the same as defined in the above compound (18), and $R^1$ is a halogen atom, or a salt thereof.
(203) The benzazepine derivative of the above formula [1] wherein $R^2$, $R^3$, $R^4$ and $R^5$ are the same as defined in the above compound (19), and $R^1$ is a halogen atom, or a salt thereof.

(204) The benzazepine derivative of the above formula [1] wherein $R^2$, $R^3$, $R^4$ and $R^5$ are the same as defined in the above compound (20), and $R^1$ is a halogen atom, or a salt thereof.
(205) The benzazepine derivative of the above formula [1] wherein $R^2$, $R^3$, $R^4$ and $R^5$ are the same as defined in the above compound (21), and $R^1$ is a halogen atom, or a salt thereof.
(206) The benzazepine derivative of the above formula [1] wherein $R^2$, $R^3$, $R^4$ and $R^5$ are the same as defined in the above compound (22), and $R^1$ is a halogen atom, or a salt thereof.
(207) The benzazepine derivative of the above formula [1] wherein $R^2$, $R^3$, $R^4$ and $R^5$ are the same as defined in the above compound (23), and $R^1$ is a halogen atom, or a salt thereof.
(208) The benzazepine derivative of the above formula [1] wherein $R^2$, $R^3$, $R^4$ and $R^5$ are the same as defined in the above compound (24), and $R^1$ is a halogen atom, or a salt thereof.
(209) The benzazepine derivative of the above formula [1] wherein $R^2$, $R^3$, $R^4$ and $R^5$ are the same as defined in the above compound (25), and $R^1$ is a halogen atom, or a salt thereof.
(210) The benzazepine derivative of the above formula [1] wherein $R^2$, $R^3$, $R^4$ and $R^5$ are the same as defined in the above compound (26), and $R^1$ is a halogen atom, or a salt thereof.
(211) The benzazepine derivative of the above formula [1] wherein $R^2$, $R^3$, $R^4$ and $R^5$ are the same as defined in the above compound (27), and $R^1$ is a halogen atom, or a salt thereof.
(212) The benzazepine derivative of the above formula [1] wherein $R^2$, $R^3$, $R^4$ and $R^5$ are the same as defined in the above compound (28), and $R^1$ is a halogen atom, or a salt thereof.
(213) The benzazepine derivative of the above formula [1] wherein $R^2$, $R^3$, $R^4$ and $R^5$ are the same as defined in the above compound (29), and $R^1$ is a halogen atom, or a salt thereof.
(214) The benzazepine derivative of the above formula [1] wherein $R^2$, $R^3$, $R^4$ and $R^5$ are the same as defined in the above compound (30), and $R^1$ is a halogen atom, or a salt thereof.
(215) The benzazepine derivative of the above formula [1] wherein $R^2$, $R^3$, $R^4$ and $R^5$ are the same as defined in the above compound (31), and $R^1$ is a halogen atom, or a salt thereof.
(216) The benzazepine derivative of the above formula [1] wherein $R^2$, $R^3$, $R^4$ and $R^5$ are the same as defined in the above compound (32), and $R^1$ is a halogen atom, or a salt thereof.
(217) The benzazepine derivative of the above formula [1] wherein $R^2$, $R^3$, $R^4$ and $R^5$ are the same as defined in the above compound (33), and $R^1$ is a halogen atom, or a salt thereof.
(218) The benzazepine derivative of the above formula [1] wherein $R^2$, $R^3$, $R^4$ and $R^5$ are the same as defined in the above compound (34), and $R^1$ is a halogen atom, or a salt thereof.
(219) The benzazepine derivative of the above formula [1] wherein $R^2$, $R^3$, $R^4$ and $R^5$ are the same as defined in the above compound (35), and $R^1$ is a halogen atom, or a salt thereof.
(220) The benzazepine derivative of the above formula [1] wherein $R^2$, $R^3$, $R^4$ and $R^5$ are the same as defined in the above compound (36), and $R^1$ is a halogen atom, or a salt thereof.
(221) The benzazepine derivative of the above formula [1] wherein $R^2$, $R^3$, $R^4$ and $R^5$ are the same as defined in the above compound (37), and $R^1$ is a halogen atom, or a salt thereof.
(222) The benzazepine derivative of the above formula [1] wherein $R^2$, $R^3$, $R^4$ and $R^5$ are the same as defined in the above compound (38), and $R^1$ is a halogen atom, or a salt thereof.
(223) The benzazepine derivative of the above formula [1] wherein $R^2$, $R^3$, $R^4$ and $R^5$ are the same as defined in the above compound (39), and $R^1$ is a halogen atom, or a salt thereof.
(224) The benzazepine derivative of the above formula [1] wherein $R^2$, $R^3$, $R^4$ and $R^5$ are the same as defined in the above compound (40), and $R^1$ is a halogen atom, or a salt thereof.
(225) The benzazepine derivative of the above formula [1] wherein $R^2$, $R^3$, $R^4$ and $R^5$ are the same as defined in the above compound (41), and $R^1$ is a halogen atom, or a salt thereof.
(226) The benzazepine derivative of the above formula [1] wherein $R^2$, $R^3$, $R^4$ and $R^5$ are the same as defined in the above compound (42), and $R^1$ is a halogen atom, or a salt thereof.
(227) The benzazepine derivative of the above formula [1] wherein $R^2$, $R^3$, $R^4$ and $R^5$ are the same as defined in the above compound (43), and $R^1$ is a halogen atom, or a salt thereof.
(228) The benzazepine derivative of the above formula [1] wherein $R^2$, $R^3$, $R^4$ and $R^5$ are the same as defined in the above compound (44), and $R^1$ is a halogen atom, or a salt thereof.
(229) The benzazepine derivative of the above formula [1] wherein $R^2$, $R^3$, $R^4$ and $R^5$ are the same as defined in the above compound (45), and $R^1$ is a halogen atom, or a salt thereof.
(230) The benzazepine derivative of the above formula [1] wherein $R^2$, $R^3$, $R^4$ and $R^5$ are the same as defined in the above compound (46), and $R^1$ is a halogen atom, or a salt thereof.
(231) The benzazepine derivative of the above formula [1] wherein $R^2$, $R^3$, $R^4$ and $R^5$ are the same as defined in the above compound (47), and $R^1$ is a halogen atom, or a salt thereof.
(232) The benzazepine derivative of the above formula [1] wherein $R^2$, $R^3$, $R^4$ and $R^5$ are the same as defined in the above compound (48), and $R^1$ is a halogen atom, or a salt thereof.
(233) The benzazepine derivative of the above formula [1] wherein $R^2$, $R^3$, $R^4$ and $R^5$ are the same as defined in the above compound (49), and $R^1$ is a halogen atom, or a salt thereof.
(234) The benzazepine derivative of the above formula [1] wherein $R^2$, $R^3$, $R^4$ and $R^5$ are the same as defined in the above compound (50), and $R^1$ is a halogen atom, or a salt thereof.
(235) The benzazepine derivative of the above formula [1] wherein $R^2$, $R^3$, $R^4$ and $R^5$ are the same as defined in the above compound (51), and $R^1$ is a halogen atom, or a salt thereof.
(236) The benzazepine derivative of the above formula [1] wherein $R^2$, $R^3$, $R^4$ and $R^5$ are the same as defined in the above compound (52), and $R^1$ is a halogen atom, or a salt thereof.
(237) The benzazepine derivative of the above formula [1] wherein $R^2$, $R^3$, $R^4$ and $R^5$ are the same as defined in the above compound (53), and $R^1$ is a halogen atom, or a salt thereof.

(238) The benzazepine derivative of the above formula [1] wherein $R^2$, $R^3$, $R^4$ and $R^5$ are the same as defined in the above compound (54), and $R^1$ is a halogen atom, or a salt thereof.
(239) The benzazepine derivative of the above formula [1] wherein $R^2$, $R^3$, $R^4$ and $R^5$ are the same as defined in the above compound (55), and $R^1$ is a halogen atom, or a salt thereof.
(240) The benzazepine derivative of the above formula [1] wherein $R^2$, $R^3$, $R^4$ and $R^5$ are the same as defined in the above compound (56), and $R^1$ is a halogen atom, or a salt thereof.
(241) The benzazepine derivative of the above formula [1] wherein $R^2$, $R^3$, $R^4$ and $R^5$ are the same as defined in the above compound (57), and $R^1$ is a halogen atom, or a salt thereof.
(242) The benzazepine derivative of the above formula [1] wherein $R^2$, $R^3$, $R^4$ and $R^5$ are the same as defined in the above compound (58), and $R^1$ is a halogen atom, or a salt thereof.
(243) The benzazepine derivative of the above formula [1] wherein $R^2$, $R^3$, $R^4$ and $R^5$ are the same as defined in the above compound (59), and $R^1$ is a halogen atom, or a salt thereof.
(244) The benzazepine derivative of the above formula [1] wherein $R^2$, $R^3$, $R^4$ and $R^5$ are the same as defined in the above compound (60), and $R^1$ is a halogen atom, or a salt thereof.
(245) The benzazepine derivative of the above formula [1] wherein $R^2$, $R^3$, $R^4$ and $R^5$ are the same as defined in the above compound (61), and $R^1$ is a halogen atom, or a salt thereof.
(246) The benzazepine derivative of the above formula [1] wherein $R^2$, $R^3$, $R^4$ and $R^5$ are the same as defined in the above compound (62), and $R^1$ is a halogen atom, or a salt thereof.
(247) The benzazepine derivative of the above formula [1] wherein $R^2$, $R^3$, $R^4$ and $R^5$ are the same as defined in the above compound (63), and $R^1$ is a halogen atom, or a salt thereof.
(248) The benzazepine derivative of the above formula [1] wherein $R^2$, $R^3$, $R^4$ and $R^5$ are the same as defined in the above compound (64), and $R^1$ is a halogen atom, or a salt thereof.
(249) The benzazepine derivative of the above formula [1] wherein $R^2$, $R^3$, $R^4$ and $R^5$ are the same as defined in the above compound (65), and $R^1$ is a halogen atom, or a salt thereof.
(250) The benzazepine derivative of the above formula [1] wherein $R^2$, $R^3$, $R^4$ and $R^5$ are the same as defined in the above compound (66), and $R^1$ is a halogen atom, or a salt thereof.
(251) The benzazepine derivative of the above formula [1] wherein $R^2$, $R^3$, $R^4$ and $R^5$ are the same as defined in the above compound (67), and $R^1$ is a halogen atom, or a salt thereof.
(252) The benzazepine derivative of the above formula [1] wherein $R^2$, $R^3$, $R^4$ and $R^5$ are the same as defined in the above compound (68), and $R^1$ is a halogen atom, or a salt thereof.
(253) The benzazepine derivative of the above formula [1] wherein $R^2$, $R^3$, $R^4$ and $R^5$ are the same as defined in the above compound (69), and $R^1$ is a halogen atom, or a salt thereof.
(254) The benzazepine derivative of the above formula [1] wherein $R^2$, $R^3$, $R^4$ and $R^5$ are the same as defined in the above compound (70), and $R^1$ is a halogen atom, or a salt thereof.
(255) The benzazepine derivative of the above formula [1] wherein $R^2$, $R^3$, $R^4$ and $R^5$ are the same as defined in the above compound (71), and $R^1$ is a halogen atom, or a salt thereof.
(256) The benzazepine derivative of the above formula [1] wherein $R^2$, $R^3$, $R^4$ and $R^5$ are the same as defined in the above compound (72), and $R^1$ is a halogen atom, or a salt thereof.
(257) The benzazepine derivative of the above formula [1] wherein $R^2$, $R^3$, $R^4$ and $R^5$ are the same as defined in the above compound (73), and $R^1$ is a halogen atom, or a salt thereof.
(258) The benzazepine derivative of the above formula [1] wherein $R^2$, $R^3$, $R^4$ and $R^5$ are the same as defined in the above compound (74), and $R^1$ is a halogen atom, or a salt thereof.
(259) The benzazepine derivative of the above formula [1] wherein $R^2$, $R^3$, $R^4$ and $R^5$ are the same as defined in the above compound (75), and $R^1$ is a halogen atom, or a salt thereof.
(260) The benzazepine derivative of the above formula [1] wherein $R^2$, $R^3$, $R^4$ and $R^5$ are the same as defined in the above compound (76), and $R^1$ is a halogen atom, or a salt thereof.
(261) The benzazepine derivative of the above formula [1] wherein $R^2$, $R^3$, $R^4$ and $R^5$ are the same as defined in the above compound (77), and $R^1$ is a halogen atom, or a salt thereof.
(262) The benzazepine derivative of the above formula [1] wherein $R^2$, $R^3$, $R^4$ and $R^5$ are the same as defined in the above compound (78), and $R^1$ is a halogen atom, or a salt thereof.
(263) The benzazepine derivative of the above formula [1] wherein $R^2$, $R^3$, $R^4$ and $R^5$ are the same as defined in the above compound (79), and $R^1$ is a halogen atom, or a salt thereof.
(264) The benzazepine derivative of the above formula [1] wherein $R^2$, $R^3$, $R^4$ and $R^5$ are the same as defined in the above compound (80), and $R^1$ is a halogen atom, or a salt thereof.
(265) The benzazepine derivative of the above formula [1] wherein $R^2$, $R^3$, $R^4$ and $R^5$ are the same as defined in the above compound (81), and $R^1$ is a halogen atom, or a salt thereof.
(266) The benzazepine derivative of the above formula [1] wherein $R^2$, $R^3$, $R^4$ and $R^5$ are the same as defined in the above compound (82), and $R^1$ is a halogen atom, or a salt thereof.
(267) The benzazepine derivative of the above formula [1] wherein $R^2$, $R^3$, $R^4$ and $R^5$ are the same as defined in the above compound (83), and $R^1$ is a halogen atom, or a salt thereof.
(268) The benzazepine derivative of the above formula [1] wherein $R^2$, $R^3$, $R^4$ and $R^5$ are the same as defined in the above compound (84), and $R^1$ is a halogen atom, or a salt thereof.
(269) The benzazepine derivative of the above formula [1] wherein $R^2$, $R^3$, $R^4$ and $R^5$ are the same as defined in the above compound (85), and $R^1$ is a halogen atom, or a salt thereof.
(270) The benzazepine derivative of the above formula [1] wherein $R^2$, $R^3$, $R^4$ and $R^5$ are the same as defined in the above compound (86), and $R^1$ is a halogen atom, or a salt thereof.
(271) The benzazepine derivative of the above formula [1] wherein $R^2$, $R^3$, $R^4$ and $R^5$ are the same as defined in the above compound (87), and $R^1$ is a halogen atom, or a salt thereof.

(272) The benzazepine derivative of the above formula [1] wherein $R^2$, $R^3$, $R^4$ and $R^5$ are the same as defined in the above compound (88), and $R^1$ is a halogen atom, or a salt thereof.
(273) The benzazepine derivative of the above formula [1] wherein $R^2$, $R^3$, $R^4$ and $R^5$ are the same as defined in the above compound (89), and $R^1$ is a halogen atom, or a salt thereof.
(274) The benzazepine derivative of the above formula [1] wherein $R^2$, $R^3$, $R^4$ and $R^5$ are the same as defined in the above compound (90), and $R^1$ is a halogen atom, or a salt thereof.
(275) The benzazepine derivative of the above formula [1] wherein $R^2$, $R^3$, $R^4$ and $R^5$ are the same as defined in the above compound (91), and $R^1$ is a halogen atom, or a salt thereof.
(276) The benzazepine derivative of the above formula [1] wherein $R^2$, $R^3$, $R^4$ and $R^5$ are the same as defined in the above compound (92), and $R^1$ is a halogen atom, or a salt thereof.
(277) The benzazepine derivative of the above formula [1] wherein $R^2$, $R^3$, $R^4$ and $R^5$ are the same as defined in the above compound (93), and $R^1$ is a halogen atom, or a salt thereof.
(278) The benzazepine derivative of the above formula [1] wherein $R^2$, $R^3$, $R^4$ and $R^5$ are the same as defined in the above compound (94), and $R^1$ is a halogen atom, or a salt thereof.
(279) The benzazepine derivative of the above formula [1] wherein $R^2$, $R^3$, $R^4$ and $R^5$ are the same as defined in the above compound (95), and $R^1$ is a halogen atom, or a salt thereof.
(280) The benzazepine derivative of the above formula [1] wherein $R^2$, $R^3$, $R^4$ and $R^5$ are the same as defined in the above compound (96), and $R^1$ is a halogen atom, or a salt thereof.
(281) The benzazepine derivative of the above formula [1] wherein $R^2$, $R^3$, $R^4$ and $R^5$ are the same as defined in the above compound (97), and $R^1$ is a halogen atom, or a salt thereof.
(282) The benzazepine derivative of the above formula [1] wherein $R^2$, $R^3$, $R^4$ and $R^5$ are the same as defined in the above compound (98), and $R^1$ is a halogen atom, or a salt thereof.
(283) The benzazepine derivative of the above formula [1] wherein $R^2$, $R^3$, $R^4$ and $R^5$ are the same as defined in the above compound (99), and $R^1$ is a halogen atom, or a salt thereof.
(284) The benzazepine derivative of the above formula [1] wherein $R^2$, $R^3$, $R^4$ and $R^5$ are the same as defined in the above compound (100), and $R^1$ is a halogen atom, or a salt thereof.
(285) The benzazepine derivative of the above formula [1] wherein $R^2$, $R^3$, $R^4$ and $R^5$ are the same as defined in the above compound (101), and $R^1$ is a halogen atom, or a salt thereof.
(286) The benzazepine derivative of the above formula [1] wherein $R^2$, $R^3$, $R^4$ and $R^5$ are the same as defined in the above compound (102), and $R^1$ is a halogen atom, or a salt thereof.
(287) The benzazepine derivative of the above formula [1] wherein $R^2$, $R^3$, $R^4$ and $R^5$ are the same as defined in the above compound (103), and $R^1$ is a halogen atom, or a salt thereof.
(288) The benzazepine derivative of the above formula [1] wherein $R^2$, $R^3$, $R^4$ and $R^5$ are the same as defined in the above compound (104), and $R^1$ is a halogen atom, or a salt thereof.
(289) The benzazepine derivative of the above formula [1] wherein $R^2$, $R^3$, $R^4$ and $R^5$ are the same as defined in the above compound (105), and $R^1$ is a halogen atom, or a salt thereof.
(290) The benzazepine derivative of the above formula [1] wherein $R^2$, $R^3$, $R^4$ and $R^5$ are the same as defined in the above compound (106), and $R^1$ is a halogen atom, or a salt thereof.
(291) The benzazepine derivative of the above formula [1] wherein $R^2$, $R^3$, $R^4$ and $R^5$ are the same as defined in the above compound (107), and $R^1$ is a halogen atom, or a salt thereof.
(292) The benzazepine derivative of the above formula [1] wherein $R^2$, $R^3$, $R^4$ and $R^5$ are the same as defined in the above compound (108), and $R^1$ is a halogen atom, or a salt thereof.
(293) The benzazepine derivative of the above formula [1] wherein $R^2$, $R^3$, $R^4$ and $R^5$ are the same as defined in the above compound (109), and $R^1$ is a halogen atom, or a salt thereof.
(294) The benzazepine derivative of the above formula [1] wherein $R^2$, $R^3$, $R^4$ and $R^5$ are the same as defined in the above compound (110), and $R^1$ is a halogen atom, or a salt thereof.
(295) The benzazepine derivative of the above formula [1] wherein $R^2$, $R^3$, $R^4$ and $R^5$ are the same as defined in the above compound (111), and $R^1$ is a halogen atom, or a salt thereof.
(296) The benzazepine derivative of the above formula [1] wherein $R^2$, $R^3$, $R^4$ and $R^5$ are the same as defined in the above compound (112), and $R^1$ is a halogen atom, or a salt thereof.
(297) The benzazepine derivative of the above formula [1] wherein $R^2$, $R^3$, $R^4$ and $R^5$ are the same as defined in the above compound (113), and $R^1$ is a halogen atom, or a salt thereof.
(298) The benzazepine derivative of the above formula [1] wherein $R^2$, $R^3$, $R^4$ and $R^5$ are the same as defined in the above compound (114), and $R^1$ is a halogen atom, or a salt thereof.
(299) The benzazepine derivative of the above formula [1] wherein $R^2$, $R^3$, $R^4$ and $R^5$ are the same as defined in the above compound (115), and $R^1$ is a halogen atom, or a salt thereof.
(300) The benzazepine derivative of the above formula [1] wherein $R^2$, $R^3$, $R^4$ and $R^5$ are the same as defined in the above compound (116), and $R^1$ is a halogen atom, or a salt thereof.
(301) The benzazepine derivative of the above formula [1] wherein $R^2$, $R^3$, $R^4$ and $R^5$ are the same as defined in the above compound (117), and $R^1$ is a halogen atom, or a salt thereof.
(302) The benzazepine derivative of the above formula [1] wherein $R^2$, $R^3$, $R^4$ and $R^5$ are the same as defined in the above compound (118), and $R^1$ is a halogen atom, or a salt thereof.
(303) The benzazepine derivative of the above formula [1] wherein $R^2$, $R^3$, $R^4$ and $R^5$ are the same as defined in the above compound (119), and $R^1$ is a halogen atom, or a salt thereof.
(304) The benzazepine derivative of the above formula [1] wherein $R^2$, $R^3$, $R^4$ and $R^5$ are the same as defined in the above compound (120), and $R^1$ is a halogen atom, or a salt thereof.
(305) The benzazepine derivative of the above formula [1] wherein $R^2$, $R^3$, $R^4$ and $R^5$ are the same as defined in the above compound (121), and $R^1$ is a halogen atom, or a salt thereof.

(306) The benzazepine derivative of the above formula [1] wherein $R^2$, $R^3$, $R^4$ and $R^5$ are the same as defined in the above compound (122), and $R^1$ is a halogen atom, or a salt thereof.
(307) The benzazepine derivative of the above formula [1] wherein $R^2$, $R^3$, $R^4$ and $R^5$ are the same as defined in the above compound (123), and $R^1$ is a halogen atom, or a salt thereof.
(308) The benzazepine derivative of the above formula [1] wherein $R^2$, $R^3$, $R^4$ and $R^5$ are the same as defined in the above compound (124), and $R^1$ is a halogen atom, or a salt thereof.
(309) The benzazepine derivative of the above formula [1] wherein $R^2$, $R^3$, $R^4$ and $R^5$ are the same as defined in the above compound (125), and $R^1$ is a halogen atom, or a salt thereof.
(310) The benzazepine derivative of the above formula [1] wherein $R^2$, $R^3$, $R^4$ and $R^5$ are the same as defined in the above compound (126), and $R^1$ is a halogen atom, or a salt thereof.
(311) The benzazepine derivative of the above formula [1] wherein $R^2$, $R^3$, $R^4$ and $R^5$ are the same as defined in the above compound (127), and $R^1$ is a halogen atom, or a salt thereof.
(312) The benzazepine derivative of the above formula [1] wherein $R^2$, $R^3$, $R^4$ and $R^5$ are the same as defined in the above compound (128), and $R^1$ is a halogen atom, or a salt thereof.
(313) The benzazepine derivative of the above formula [1] wherein $R^2$, $R^3$, $R^4$ and $R^5$ are the same as defined in the above compound (129), and $R^1$ is a halogen atom, or a salt thereof.
(314) The benzazepine derivative of the above formula [1] wherein $R^2$, $R^3$, $R^4$ and $R^5$ are the same as defined in the above compound (130), and $R^1$ is a halogen atom, or a salt thereof.
(315) The benzazepine derivative of the above formula [1] wherein $R^2$, $R^3$, $R^4$ and $R^5$ are the same as defined in the above compound (131), and $R^1$ is a halogen atom, or a salt thereof.
(316) The benzazepine derivative of the above formula [1] wherein $R^2$, $R^3$, $R^4$ and $R^5$ are the same as defined in the above compound (132), and $R^1$ is a halogen atom, or a salt thereof.
(317) The benzazepine derivative of the above formula [1] wherein $R^2$, $R^3$, $R^4$ and $R^5$ are the same as defined in the above compound (133), and $R^1$ is a halogen atom, or a salt thereof.
(318) The benzazepine derivative of the above formula [1] wherein $R^2$, $R^3$, $R^4$ and $R^5$ are the same as defined in the above compound (134), and $R^1$ is a halogen atom, or a salt thereof.
(319) The benzazepine derivative of the above formula [1] wherein $R^2$, $R^3$, $R^4$ and $R^5$ are the same as defined in the above compound (135), and $R^1$ is a halogen atom, or a salt thereof.
(320) The benzazepine derivative of the above formula [1] wherein $R^2$, $R^3$, $R^4$ and $R^5$ are the same as defined in the above compound (136), and $R^1$ is a halogen atom, or a salt thereof.
(321) The benzazepine derivative of the above formula [1] wherein $R^2$, $R^3$, $R^4$ and $R^5$ are the same as defined in the above compound (137), and $R^1$ is a halogen atom, or a salt thereof.
(322) The benzazepine derivative of the above formula [1] wherein $R^2$, $R^3$, $R^4$ and $R^5$ are the same as defined in the above compound (138), and $R^1$ is a halogen atom, or a salt thereof.
(323) The benzazepine derivative of the above formula [1] wherein $R^2$, $R^3$, $R^4$ and $R^5$ are the same as defined in the above compound (139), and $R^1$ is a halogen atom, or a salt thereof.
(324) The benzazepine derivative of the above formula [1] wherein $R^2$, $R^3$, $R^4$ and $R^5$ are the same as defined in the above compound (140), and $R^1$ is a halogen atom, or a salt thereof.
(325) The benzazepine derivative of the above formula [1] wherein $R^2$, $R^3$, $R^4$ and $R^5$ are the same as defined in the above compound (141), and $R^1$ is a halogen atom, or a salt thereof.
(326) The benzazepine derivative of the above formula [1] wherein $R^2$, $R^3$, $R^4$ and $R^5$ are the same as defined in the above compound (142), and $R^1$ is a halogen atom, or a salt thereof.
(327) The benzazepine derivative of the above formula [1] wherein $R^2$, $R^3$, $R^4$ and $R^5$ are the same as defined in the above compound (143), and $R^1$ is a halogen atom, or a salt thereof.
(328) The benzazepine derivative of the above formula [1] wherein $R^2$, $R^3$, $R^4$ and $R^5$ are the same as defined in the above compound (144), and $R^1$ is a halogen atom, or a salt thereof.
(329) The benzazepine derivative of the above formula [1] wherein $R^2$, $R^3$, $R^4$ and $R^5$ are the same as defined in the above compound (145), and $R^1$ is a halogen atom, or a salt thereof.
(330) The benzazepine derivative of the above formula [1] wherein $R^2$, $R^3$, $R^4$ and $R^5$ are the same as defined in the above compound (146), and $R^1$ is a halogen atom, or a salt thereof.
(331) The benzazepine derivative of the above formula [1] wherein $R^2$, $R^3$, $R^4$ and $R^5$ are the same as defined in the above compound (147), and $R^1$ is a halogen atom, or a salt thereof.
(332) The benzazepine derivative of the above formula [1] wherein $R^2$, $R^3$, $R^4$ and $R^5$ are the same as defined in the above compound (148), and $R^1$ is a halogen atom, or a salt thereof.
(333) The benzazepine derivative of the above formula [1] wherein $R^2$, $R^3$, $R^4$ and $R^5$ are the same as defined in the above compound (149), and $R^1$ is a halogen atom, or a salt thereof.
(334) The benzazepine derivative of the above formula [1] wherein $R^2$, $R^3$, $R^4$ and $R^5$ are the same as defined in the above compound (150), and $R^1$ is a halogen atom, or a salt thereof.
(335) The benzazepine derivative of the above formula [1] wherein $R^2$, $R^3$, $R^4$ and $R^5$ are the same as defined in the above compound (151), and $R^1$ is a halogen atom, or a salt thereof.
(336) The benzazepine derivative of the above formula [1] wherein $R^2$, $R^3$, $R^4$ and $R^5$ are the same as defined in the above compound (152), and $R^1$ is a halogen atom, or a salt thereof.
(337) The benzazepine derivative of the above formula [1] wherein $R^2$, $R^3$, $R^4$ and $R^5$ are the same as defined in the above compound (153), and $R^1$ is a halogen atom, or a salt thereof.
(338) The benzazepine derivative of the above formula [1] wherein $R^2$, $R^3$, $R^4$ and $R^5$ are the same as defined in the above compound (154), and $R^1$ is a halogen atom, or a salt thereof.
(339) The benzazepine derivative of the above formula [1] wherein $R^2$, $R^3$, $R^4$ and $R^5$ are the same as defined in the above compound (155), and $R^1$ is a halogen atom, or a salt thereof.

(340) The benzazepine derivative of the above formula [1] wherein $R^2$, $R^3$, $R^4$ and $R^5$ are the same as defined in the above compound (156), and $R^1$ is a halogen atom, or a salt thereof.
(341) The benzazepine derivative of the above formula [1] wherein $R^2$, $R_3$, $R^4$ and $R^5$ are the same as defined in the above compound (157), and $R^1$ is a halogen atom, or a salt thereof.
(342) The benzazepine derivative of the above formula [1] wherein $R^2$, $R^3$, $R^4$ and $R^5$ are the same as defined in the above compound (158), and $R^1$ is a halogen atom, or a salt thereof.
(343) The benzazepine derivative of the above formula [1] wherein $R^2$, $R^3$, $R^4$ and $R^5$ are the same as defined in the above compound (159), and $R^1$ is a halogen atom, or a salt thereof.
(344) The benzazepine derivative of the above formula [1] wherein $R^2$, $R^3$, $R^4$ and $R^5$ are the same as defined in the above compound (160), and $R^1$ is a halogen atom, or a salt thereof.
(345) The benzazepine derivative of the above formula [1] wherein $R^2$, $R^3$, $R^4$ and $R^5$ are the same as defined in the above compound (161), and $R^1$ is a halogen atom, or a salt thereof.
(346) The benzazepine derivative of the above formula [1] wherein $R^2$, $R^3$, $R^4$ and $R^5$ are the same as defined in the above compound (162), and $R^1$ is a halogen atom, or a salt thereof.
(347) The benzazepine derivative of the above formula [1] wherein $R^2$, $R^3$, $R^4$ and $R^5$ are the same as defined in the above compound (1 63), and $R^1$ is a halogen atom, or a salt thereof.
(348) The benzazepine derivative of the above formula [1] wherein $R^2$, $R^3$, $R^4$ and $R^5$ are the same as defined in the above compound (1 64), and $R^1$ is a halogen atom, or a salt thereof.
(349) The benzazepine derivative of the above formula [1] wherein $R^2$, $R^3$, $R^4$ and $R^5$ are the same as defined in the above compound (165), and $R^1$ is a halogen atom, or a salt thereof.
(350) The benzazepine derivative of the above formula [1] wherein $R^2$, $R^3$, $R^4$ and $R^5$ are the same as defined in the above compound (166), and $R^1$ is a halogen atom, or a salt thereof.
(351) The benzazepine derivative of the above formula [1] wherein $R^2$, $R^3$, $R^4$ and $R^5$ are the same as defined in the above compound (167), and $R^1$ is a halogen atom, or a salt thereof.
(352) The benzazepine derivative of the above formula [1] wherein $R^2$, $R^3$, $R^4$ and $R^5$ are the same as defined in the above compound (168), and $R^1$ is a halogen atom, or a salt thereof.
(353) The benzazepine derivative of the above formula [1] wherein $R^2$, $R^3$, $R^4$ and $R^5$ are the same as defined in the above compound (169), and $R^1$ is a halogen atom, or a salt thereof.
(354) The benzazepine derivative of the above formula [1] wherein $R^2$, $R^3$, $R^4$ and $R^5$ are the same as defined in the above compound (170), and $R^1$ is a halogen atom, or a salt thereof.
(355) The benzazepine derivative of the above formula [1] wherein $R^2$, $R^3$, $R^4$ and $R^5$ are the same as defined in the above compound (171), and $R^1$ is a halogen atom, or a salt thereof.
(356) The benzazepine derivative of the above formula [1] wherein $R^2$, $R^3$, $R^4$ and $R^5$ are the same as defined in the above compound (172), and $R^1$ is a halogen atom, or a salt thereof.
(357) The benzazepine derivative of the above formula [1] wherein $R^2$, $R^3$, $R^4$ and $R^5$ are the same as defined in the above compound (173), and $R^1$ is a halogen atom, or a salt thereof.
(358) The benzazepine derivative of the above formula [1] wherein $R^2$, $R^3$, $R^4$ and $R^5$ are the same as defined in the above compound (174), and $R^1$ is a halogen atom, or a salt thereof.
(359) The benzazepine derivative of the above formula [1] wherein $R^2$, $R^3$, $R^4$ and $R^5$ are the same as defined in the above compound (175), and $R^1$ is a halogen atom, or a salt thereof.
(360) The benzazepine derivative of the above formula [1] wherein $R^2$, $R^3$, $R^4$ and $R^5$ are the same as defined in the above compound (176), and $R^1$ is a halogen atom, or a salt thereof.
(361) The benzazepine derivative of the above formula [1] wherein $R^2$, $R^3$, $R^4$ and $R^5$ are the same as defined in the above compound (177), and $R^1$ is a halogen atom, or a salt thereof.
(362) The benzazepine derivative of the above formula [1] wherein $R^2$, $R^3$, $R^4$ and $R^5$ are the same as defined in the above compound (178), and $R^1$ is a halogen atom, or a salt thereof.
(363) The benzazepine derivative of the above formula [1] wherein $R^2$, $R^3$, $R^4$ and $R^5$ are the same as defined in the above compound (179), and $R^1$ is a halogen atom, or a salt thereof.
(364) The benzazepine derivative of the above formula [1] wherein $R^2$, $R^3$, $R^4$ and $R^5$ are the same as defined in the above compound (180), and $R^1$ is a halogen atom, or a salt thereof.
(365) The benzazepine derivative of the above formula [1] wherein $R^2$, $R^3$, $R^4$ and $R^5$ are the same as defined in the above compound (181), and $R^1$ is a halogen atom, or a salt thereof.
(366) The benzazepine derivative of the above formula [1] wherein $R^2$, $R^3$, $R^4$ and $R^5$ are the same as defined in the above compound (182), and $R^1$ is a halogen atom, or a salt thereof.
(367) The benzazepine derivative of the above formula [1] wherein $R^2$, $R^3$, $R^4$ and $R^5$ are the same as defined in the above compound (183), and $R^1$ is a halogen atom, or a salt thereof.
(368) The benzazepine derivative of the above formula [1] wherein $R^2$, $R^3$, $R^4$ and $R^5$ are the same as defined in the above compound (184), and $R^1$ is a halogen atom, or a salt thereof.
(369) The benzazepine derivative of the above formula [1] wherein $R^1$, $R^2$, $R^3$ and $R^4$ are the same as defined in the above compound (277), and $R^5$ is a pyrrolidinyl group, or a salt thereof.
(370) The benzazepine derivative of the above formula [1] wherein $R^1$, $R^2$, $R^3$ and $R^4$ are the same as defined in the above compound (278), and $R^5$ is a pyrrolidinyl group, or a salt thereof.
(371) The benzazepine derivative of the above formula [1] wherein $R^1$, $R^2$, $R^3$ and $R^4$ are the same as defined in the above compound (279), and $R^5$ is a pyrrolidinyl group, or a salt thereof.
(372) The benzazepine derivative of the above formula [1] wherein $R^1$, $R^2$, $R^3$ and $R^4$ are the same as defined in the above compound (280), and $R^5$ is a pyrrolidinyl group, or a salt thereof.
(373) The benzazepine derivative of the above formula [1] wherein $R^1$, $R^2$, $R^3$ and $R^4$ are the same as defined in the above compound (281), and $R^5$ is a pyrrolidinyl group, or a salt thereof.

(374) The benzazepine derivative of the above formula [1] wherein $R^1$, $R^2$, $R^3$ and $R^4$ are the same as defined in the above compound (282), and $R^5$ is a pyrrolidinyl group, or a salt thereof.
(375) The benzazepine derivative of the above formula [1] wherein $R^1$, $R^2$, $R^3$ and $R^4$ are the same as defined in the above compound (283), and $R^5$ is a pyrrolidinyl group, or a salt thereof.
(376) The benzazepine derivative of the above formula [1] wherein $R^1$, $R^2$, $R^3$ and $R^4$ are the same as defined in the above compound (284), and $R^5$ is a pyrrolidinyl group, or a salt thereof.
(377) The benzazepine derivative of the above formula [1] wherein $R^1$, $R^2$, $R^3$ and $R^4$ are the same as defined in the above compound (285), and $R^5$ is a pyrrolidinyl group, or a salt thereof.
(378) The benzazepine derivative of the above formula [1] wherein $R^1$, $R^2$, $R^3$ and $R^4$ are the same as defined in the above compound (286), and $R^5$ is a pyrrolidinyl group, or a salt thereof.
(379) The benzazepine derivative of the above formula [1] wherein $R^1$, $R^2$, $R^3$ and $R^4$ are the same as defined in the above compound (287), and $R^5$ is a pyrrolidinyl group, or a salt thereof.
(380) The benzazepine derivative of the above formula [1] wherein $R^1$, $R^2$, $R^3$ and $R^4$ are the same as defined in the above compound (288), and $R^5$ is a pyrrolidinyl group, or a salt thereof.
(381) The benzazepine derivative of the above formula [1] wherein $R^1$, $R^2$, $R^3$ and $R^4$ are the same as defined in the above compound (289), and $R^5$ is a pyrrolidinyl group, or a salt thereof.
(382) The benzazepine derivative of the above formula [1] wherein $R^1$, $R^2$, $R^3$ and $R^4$ are the same as defined in the above compound (290), and $R^5$ is a pyrrolidinyl group, or a salt thereof.
(383) The benzazepine derivative of the above formula [1] wherein $R^1$, $R^2$, $R^3$ and $R^4$ are the same as defined in the above compound (291), and $R^5$ is a pyrrolidinyl group, or a salt thereof.
(384) The benzazepine derivative of the above formula [1] wherein $R^1$, $R^2$, $R^3$ and $R^4$ are the same as defined in the above compound (292), and $R^5$ is a pyrrolidinyl group, or a salt thereof.
(385) The benzazepine derivative of the above formula [1] wherein $R^1$, $R^2$, $R^3$ and $R^4$ are the same as defined in the above compound (293), and $R^5$ is a pyrrolidinyl group, or a salt thereof.
(386) The benzazepine derivative of the above formula [1] wherein $R^1$, $R^2$, $R^3$ and $R^4$ are the same as defined in the above compound (294), and $R^5$ is a pyrrolidinyl group, or a salt thereof.
(387) The benzazepine derivative of the above formula [1] wherein $R^1$, $R^2$, $R^3$ and $R^4$ are the same as defined in the above compound (295), and $R^5$ is a pyrrolidinyl group, or a salt thereof.
(388) The benzazepine derivative of the above formula [1] wherein $R^1$, $R^2$, $R^3$ and $R^4$ are the same as defined in the above compound (296), and $R^5$ is a pyrrolidinyl group, or a salt thereof.
(389) The benzazepine derivative of the above formula [1] wherein $R^1$, $R^2$, $R^3$ and $R^4$ are the same as defined in the above compound (297), and $R^5$ is a pyrrolidinyl group, or a salt thereof.
(390) The benzazepine derivative of the above formula [1] wherein $R^1$, $R^2$, $R^3$ and $R^4$ are the same as defined in the above compound (298), and $R^5$ is a pyrrolidinyl group, or a salt thereof.
(391) The benzazepine derivative of the above formula [1] wherein $R^1$, $R^2$, $R^3$ and $R^4$ are the same as defined in the above compound (299), and $R^5$ is a pyrrolidinyl group, or a salt thereof.
(392) The benzazepine derivative of the above formula [1] wherein $R^1$, $R^2$, $R^3$ and $R^4$ are the same as defined in the above compound (300), and $R^5$ is a pyrrolidinyl group, or a salt thereof.
(393) The benzazepine derivative of the above formula [1] wherein $R^1$, $R^2$, $R^3$ and $R^4$ are the same as defined in the above compound (301), and $R^5$ is a pyrrolidinyl group, or a salt thereof.
(394) The benzazepine derivative of the above formula [1] wherein $R^1$, $R^2$, $R^3$ and $R^4$ are the same as defined in the above compound (302), and $R^5$ is a pyrrolidinyl group, or a salt thereof.
(395) The benzazepine derivative of the above formula [1] wherein $R^1$, $R^2$, $R^3$ and $R^4$ are the same as defined in the above compound (303), and $R^5$ is a pyrrolidinyl group, or a salt thereof.
(396) The benzazepine derivative of the above formula [1] wherein $R^1$, $R^2$, $R^3$ and $R^4$ are the same as defined in the above compound (304), and $R^5$ is a pyrrolidinyl group, or a salt thereof.
(397) The benzazepine derivative of the above formula [1] wherein $R^1$, $R^2$, $R^3$ and $R^4$ are the same as defined in the above compound (305), and $R^5$ is a pyrrolidinyl group, or a salt thereof.
(398) The benzazepine derivative of the above formula [1] wherein $R^1$, $R^2$, $R^3$ and $R^4$ are the same as defined in the above compound (306), and $R^5$ is a pyrrolidinyl group, or a salt thereof.
(399) The benzazepine derivative of the above formula [1] wherein $R^1$, $R^2$, $R^3$ and $R^4$ are the same as defined in the above compound (307), and $R^5$ is a pyrrolidinyl group, or a salt thereof.
(400) The benzazepine derivative of the above formula [1] wherein $R^1$, $R^2$, $R^3$ and $R^4$ are the same as defined in the above compound (308), and $R^5$ is a pyrrolidinyl group, or a salt thereof.
(401) The benzazepine derivative of the above formula [1] wherein $R^1$, $R^2$, $R^3$ and $R^4$ are the same as defined in the above compound (309), and $R^5$ is a pyrrolidinyl group, or a salt thereof.
(402) The benzazepine derivative of the above formula [1] wherein $R^1$, $R^2$, $R^3$ and $R^4$ are the same as defined in the above compound (310), and $R^5$ is a pyrrolidinyl group, or a salt thereof.
(403) The benzazepine derivative of the above formula [1] wherein $R^1$, $R^2$, $R^3$ and $R^4$ are the same as defined in the above compound (311), and $R^5$ is a pyrrolidinyl group, or a salt thereof.
(404) The benzazepine derivative of the above formula [1] wherein $R^1$, $R^2$, $R^3$ and $R^4$ are the same as defined in the above compound (312), and $R^5$ is a pyrrolidinyl group, or a salt thereof.
(405) The benzazepine derivative of the above formula [1] wherein $R^1$, $R^2$, $R^3$ and $R^4$ are the same as defined in the above compound (313), and $R^5$ is a pyrrolidinyl group, or a salt thereof.
(406) The benzazepine derivative of the above formula [1] wherein $R^1$, $R^2$, $R^3$ and $R^4$ are the same as defined in the above compound (314), and $R^5$ is a pyrrolidinyl group, or a salt thereof.
(407) The benzazepine derivative of the above formula [1] wherein $R^1$, $R^2$, $R^3$ and $R^4$ are the same as defined in the above compound (315), and $R^5$ is a pyrrolidinyl group, or a salt thereof.

(408) The benzazepine derivative of the above formula [1] wherein $R^1$, $R^2$, $R^3$ and $R^4$ are the same as defined in the above compound (316), and $R^5$ is a pyrrolidinyl group, or a salt thereof.
(409) The benzazepine derivative of the above formula [1] wherein $R^1$, $R^2$, $R^3$ and $R^4$ are the same as defined in the above compound (317), and $R^5$ is a pyrrolidinyl group, or a salt thereof.
(410) The benzazepine derivative of the above formula [1] wherein $R^1$, $R^2$, $R^3$ and $R^4$ are the same as defined in the above compound (318), and $R^5$ is a pyrrolidinyl group, or a salt thereof.
(411) The benzazepine derivative of the above formula [1] wherein $R^1$, $R^2$, $R^3$ and $R^4$ are the same as defined in the above compound (319), and $R^5$ is a pyrrolidinyl group, or a salt thereof.
(412) The benzazepine derivative of the above formula [1] wherein $R^1$, $R^2$, $R^3$ and $R^4$ are the same as defined in the above compound (320), and $R^5$ is a pyrrolidinyl group, or a salt thereof.
(413) The benzazepine derivative of the above formula [1] wherein $R^1$, $R^2$, $R^3$ and $R^4$ are the same as defined in the above compound (321), and $R^5$ is a pyrrolidinyl group, or a salt thereof.
(414) The benzazepine derivative of the above formula [1] wherein $R^1$, $R^2$, $R^3$ and $R^4$ are the same as defined in the above compound (322), and $R^5$ is a pyrrolidinyl group, or a salt thereof.
(415) The benzazepine derivative of the above formula [1] wherein $R^1$, $R^2$, $R^3$ and $R^4$ are the same as defined in the above compound (323), and $R^5$ is a pyrrolidinyl group, or a salt thereof.
(416) The benzazepine derivative of the above formula [1] wherein $R^1$, $R^2$, $R^3$ and $R^4$ are the same as defined in the above compound (324), and $R^5$ is a pyrrolidinyl group, or a salt thereof.
(417) The benzazepine derivative of the above formula [1] wherein $R^1$, $R^2$, $R^3$ and $R^4$ are the same as defined in the above compound (325), and $R^5$ is a pyrrolidinyl group, or a salt thereof.
(418) The benzazepine derivative of the above formula [1] wherein $R^1$, $R^2$, $R^3$ and $R^4$ are the same as defined in the above compound (326), and $R^5$ is a pyrrolidinyl group, or a salt thereof.
(419) The benzazepine derivative of the above formula [1] wherein $R^1$, $R^2$, $R^3$ and $R^4$ are the same as defined in the above compound (327), and $R^5$ is a pyrrolidinyl group, or a salt thereof.
(420) The benzazepine derivative of the above formula [1] wherein $R^1$, $R^2$, $R^3$ and $R^4$ are the same as defined in the above compound (328), and $R^5$ is a pyrrolidinyl group, or a salt thereof.
(421) The benzazepine derivative of the above formula [1] wherein $R^1$, $R^2$, $R^3$ and $R^4$ are the same as defined in the above compound (329), and $R^5$ is a pyrrolidinyl group, or a salt thereof.
(422) The benzazepine derivative of the above formula [1] wherein $R^1$, $R^2$, $R^3$ and $R^4$ are the same as defined in the above compound (330), and $R^5$ is a pyrrolidinyl group, or a salt thereof.
(423) The benzazepine derivative of the above formula [1] wherein $R^1$, $R^2$, $R^3$ and $R^4$ are the same as defined in the above compound (331), and $R^5$ is a pyrrolidinyl group, or a salt thereof.
(424) The benzazepine derivative of the above formula [1] wherein $R^1$, $R^2$, $R^3$ and $R^4$ are the same as defined in the above compound (332), and $R^5$ is a pyrrolidinyl group, or a salt thereof.
(425) The benzazepine derivative of the above formula [1] wherein $R^1$, $R^2$, $R^3$ and $R^4$ are the same as defined in the above compound (333), and $R^5$ is a pyrrolidinyl group, or a salt thereof.
(426) The benzazepine derivative of the above formula [1] wherein $R^1$, $R^2$, $R^3$ and $R^4$ are the same as defined in the above compound (334), and $R^5$ is a pyrrolidinyl group, or a salt thereof.
(427) The benzazepine derivative of the above formula [1] wherein $R^1$, $R^2$, $R^3$ and $R^4$ are the same as defined in the above compound (335), and $R^5$ is a pyrrolidinyl group, or a salt thereof.
(428) The benzazepine derivative of the above formula [1] wherein $R^1$, $R^2$, $R^3$ and $R^4$ are the same as defined in the above compound (336), and $R^5$ is a pyrrolidinyl group, or a salt thereof.
(429) The benzazepine derivative of the above formula [1] wherein $R^1$, $R^2$, $R^3$ and $R^4$ are the same as defined in the above compound (337), and $R^5$ is a pyrrolidinyl group, or a salt thereof.
(430) The benzazepine derivative of the above formula [1] wherein $R^1$, $R^2$, $R^3$ and $R^4$ are the same as defined in the above compound (338), and $R^5$ is a pyrrolidinyl group, or a salt thereof.
(431) The benzazepine derivative of the above formula [1] wherein $R^1$, $R^2$, $R^3$ and $R^4$ are the same as defined in the above compound (339), and $R^5$ is a pyrrolidinyl group, or a salt thereof.
(432) The benzazepine derivative of the above formula [1] wherein $R^1$, $R^2$, $R^3$ and $R^4$ are the same as defined in the above compound (340), and $R^5$ is a pyrrolidinyl group, or a salt thereof.
(433) The benzazepine derivative of the above formula [1] wherein $R^1$, $R^2$, $R^3$ and $R^4$ are the same as defined in the above compound (341), and $R^5$ is a pyrrolidinyl group, or a salt thereof.
(434) The benzazepine derivative of the above formula [1] wherein $R^1$, $R^2$, $R^3$ and $R^4$ are the same as defined in the above compound (342), and $R^5$ is a pyrrolidinyl group, or a salt thereof.
(435) The benzazepine derivative of the above formula [1] wherein $R^1$, $R^2$, $R^3$ and $R^4$ are the same as defined in the above compound (343), and $R^5$ is a pyrrolidinyl group, or a salt thereof.
(436) The benzazepine derivative of the above formula [1] wherein $R^1$, $R^2$, $R^3$ and $R^4$ are the same as defined in the above compound (344), and $R^5$ is a pyrrolidinyl group, or a salt thereof.
(437) The benzazepine derivative of the above formula [1] wherein $R^1$, $R^2$, $R^3$ and $R^4$ are the same as defined in the above compound (345), and $R^5$ is a pyrrolidinyl group, or a salt thereof.
(438) The benzazepine derivative of the above formula [1] wherein $R^1$, $R^2$, $R^3$ and $R^4$ are the same as defined in the above compound (346), and $R^5$ is a pyrrolidinyl group, or a salt thereof.
(439) The benzazepine derivative of the above formula [1] wherein $R^1$, $R^2$, $R^3$ and $R^4$ are the same as defined in the above compound (347), and $R^5$ is a pyrrolidinyl group, or a salt thereof.
(440) The benzazepine derivative of the above formula [1] wherein $R^1$, $R^2$, $R^3$ and $R^4$ are the same as defined in the above compound (348), and $R^5$ is a pyrrolidinyl group, or a salt thereof.
(441) The benzazepine derivative of the above formula [1] wherein $R^1$, $R^2$, $R^3$ and $R^4$ are the same as defined in the above compound (349), and $R^5$ is a pyrrolidinyl group, or a salt thereof.

(442) The benzazepine derivative of the above formula [1] wherein $R^1$, $R^2$, $R^3$ and $R^4$ are the same as defined in the above compound (350), and $R^5$ is a pyrrolidinyl group, or a salt thereof.
(443) The benzazepine derivative of the above formula [1] wherein $R^1$, $R^2$, $R^3$ and $R^4$ are the same as defined in the above compound (351), and $R^5$ is a pyrrolidinyl group, or a salt thereof.
(444) The benzazepine derivative of the above formula [1] wherein $R^1$, $R^2$, $R^3$ and $R^4$ are the same as defined in the above compound (352), and $R^5$ is a pyrrolidinyl group, or a salt thereof.
(445) The benzazepine derivative of the above formula [1] wherein $R^1$, $R^2$, $R^3$ and $R^4$ are the same as defined in the above compound (353), and $R^5$ is a pyrrolidinyl group, or a salt thereof.
(446) The benzazepine derivative of the above formula [1] wherein $R^1$, $R^2$, $R^3$ and $R^4$ are the same as defined in the above compound (354), and $R^5$ is a pyrrolidinyl group, or a salt thereof.
(447) The benzazepine derivative of the above formula [1] wherein $R^1$, $R^2$, $R^3$ and $R^4$ are the same as defined in the above compound (355), and $R^5$ is a pyrrolidinyl group, or a salt thereof.
(448) The benzazepine derivative of the above formula [1] wherein $R^1$, $R^2$, $R^3$ and $R^4$ are the same as defined in the above compound (356), and $R^5$ is a pyrrolidinyl group, or a salt thereof.
(449) The benzazepine derivative of the above formula [1] wherein $R^1$, $R^2$, $R^3$ and $R^4$ are the same as defined in the above compound (357), and $R^5$ is a pyrrolidinyl group, or a salt thereof.
(450) The benzazepine derivative of the above formula [1] wherein $R^1$, $R^2$, $R^3$ and $R^4$ are the same as defined in the above compound (358), and $R^5$ is a pyrrolidinyl group, or a salt thereof.
(451) The benzazepine derivative of the above formula [1] wherein $R^1$, $R^2$, $R^3$ and $R^4$ are the same as defined in the above compound (359), and $R^5$ is a pyrrolidinyl group, or a salt thereof.
(452) The benzazepine derivative of the above formula [1] wherein $R^1$, $R^2$, $R^3$ and $R^4$ are the same as defined in the above compound (360), and $R^5$ is a pyrrolidinyl group, or a salt thereof.
(453) The benzazepine derivative of the above formula [1] wherein $R^1$, $R^2$, $R^3$ and $R^4$ are the same as defined in the above compound (361), and $R^5$ is a pyrrolidinyl group, or a salt thereof.
(454) The benzazepine derivative of the above formula [1] wherein $R^1$, $R^2$, $R^3$ and $R^4$ are the same as defined in the above compound (362), and $R^5$ is a pyrrolidinyl group, or a salt thereof.
(455) The benzazepine derivative of the above formula [1] wherein $R^1$, $R^2$, $R^3$ and $R^4$ are the same as defined in the above compound (363), and $R^5$ is a pyrrolidinyl group, or a salt thereof.
(456) The benzazepine derivative of the above formula [1] wherein $R^1$, $R^2$, $R^3$ and $R^4$ are the same as defined in the above compound (364), and $R^5$ is a pyrrolidinyl group, or a salt thereof.
(457) The benzazepine derivative of the above formula [1] wherein $R^1$, $R^2$, $R^3$ and $R^4$ are the same as defined in the above compound (365), and $R^5$ is a pyrrolidinyl group, or a salt thereof.
(458) The benzazepine derivative of the above formula [1] wherein $R^1$, $R^2$, $R^3$ and $R^4$ are the same as defined in the above compound (366), and $R^5$ is a pyrrolidinyl group, or a salt thereof.
(459) The benzazepine derivative of the above formula [1] wherein $R^1$, $R^2$, $R^3$ and $R^4$ are the same as defined in the above compound (367), and $R^5$ is a pyrrolidinyl group, or a salt thereof.
(460) The benzazepine derivative of the above formula [1] wherein $R^1$, $R^2$, $R^3$ and $R^4$ are the same as defined in the above compound (368), and $R^5$ is a pyrrolidinyl group, or a salt thereof.
(461) 5-Isopropylaminocarbonylmethyl-1-[4-(1-pyrrolidinyl)-2-chlorobenzoyl]-2,3,4,5-tetrahydro-1H-benzazepine
(462) 5-[(4-Methyl-1-piperazinyl)carbonylmethyl]-1-[4-(1-pyrrolidinyl)-2-chlorobenzoyl]-2,3,4,5-tetrahydro-1H-benzazepine
(463) 5-Isopropylaminocarbonylmethyl-1-(4-n-propylamino-2-methylbenzoyl)-2,3,4,5-tetrahydro-1H-benzazepine
(464) The benzazepine derivative of the above formula [1] wherein $R^1$ is a hydrogen atom, both $R^2$ and $R^3$ are a thiazolyl group, $R^4$ is a hydrogen atom, a lower alkyl group, a hydroxy group, an amino group having optionally a lower alkanoyl substituent, a nitro group, a halogen atom or a lower alkoxy group, and $R^5$ is a group of the formula: —$NHR^6$ ($R^6$ is a lower alkyl group), or a salt thereof.
(465) The benzazepine derivative of the above formula [1] wherein $R^1$ is a hydrogen atom, both $R^2$ and $R^3$ are a phenoxy-lower alkyl group, and $R^4$ and $R^5$ are the same as defined in the above compound (464), or a salt thereof.
(466) The benzazepine derivative of the above formula [1] wherein $R^1$ is a hydrogen atom, $R^2$ and $R^3$ are different, and are a hydrogen atom or a thiazolyl group, and $R^4$ and $R^5$ are the same as defined in the above compound (464), or a salt thereof.
(467) The benzazepine derivative of the above formula [1] wherein $R^1$ is a hydrogen atom, $R^2$ and $R^3$ are different, and are a phenoxy-lower alkyl group or a thiazolyl group, and $R^4$ and $R^5$ are the same as defined in the above compound (464), or a salt thereof.
(468) The benzazepine derivative of the above formula [1] wherein $R^1$ is a hydrogen atom, $R^2$ and $R^3$ are different, and are a lower alkoxy group or a thiazolyl group, and $R^4$ and $R^5$ are the same as defined in the above compound (464), or a salt thereof.
(469) The benzazepine derivative of the above formula [1] wherein $R^1$ is a hydrogen atom, $R^2$ and $R^3$ are different, and are a thiazolyl group or a lower alkyl group having optionally a lower alkoxy substituent, and $R^4$ and $R^5$ are the same as defined in the above compound (464), or a salt thereof.
(470) The benzazepine derivative of the above formula [1] wherein $R^1$ is a hydrogen atom, $R^2$ and $R^3$ are different, and are a thiazolyl group or a hydroxy-substituted lower alkyl group, and $R^4$ and $R^5$ are the same as defined in the above compound (464), or a salt thereof.
(471) The benzazepine derivative of the above formula [1] wherein $R^1$ is a hydrogen atom, $R^2$ and $R^3$ are different, and are a thiazolyl group or an amino-substituted lower alkyl group having optionally a lower alkyl substituent, and $R^4$ and $R^5$ are the same as defined in the above compound (464), or a salt thereof.
(472) The benzazepine derivative of the above formula [1] wherein $R^1$ is a hydrogen atom, $R^2$ and $R^3$ are different, and are a thiazolyl group or a carbamoyl-substituted lower alkyl group, and $R^4$ and $R^5$ are the same as defined in the above compound (464), or a salt thereof.
(473) The benzazepine derivative of the above formula [1] wherein $R^1$ is a hydrogen atom, $R^2$ and $R^3$ are different, and are a thiazolyl group or an adamantyl-substituted lower alkyl group, and $R^4$ and $R^5$ are the same as defined in the above compound (464), or a salt thereof.

(474) The benzazepine derivative of the above formula [1] wherein $R^1$ is a hydrogen atom, $R^2$ and $R^3$ are different, and are a thiazolyl group or a lower alkylsulfonyl group, and $R^4$ and $R^5$ are the same as defined in the above compound (464), or a salt thereof.

(475) The benzazepine derivative of the above formula [1] wherein $R^1$ is a hydrogen atom, $R^2$ and $R^3$ are different, and are a thiazolyl group or a pyridyl group, and $R^4$ and $R^5$ are the same as defined in the above compound (464), or a salt thereof.

(476) The benzazepine derivative of the above formula [1] wherein $R^1$ is a hydrogen atom, $R^2$ and $R^3$ are different, and are a thiazolyl group or a pyridyl-lower alkyl group, and $R^4$ and $R^5$ are the same as defined in the above compound (464), or a salt thereof.

(477) The benzazepine derivative of the above formula [1] wherein $R^1$ is a hydrogen atom, $R^2$ and $R^3$ are different, and are a thiazolyl group or an imidazolyl-lower alkyl group having optionally a lower alkyl substituent, and $R^4$ and $R^5$ are the same as defined in the above compound (464), or a salt thereof.

(478) The benzazepine derivative of the above formula [1] wherein $R^1$ is a hydrogen atom, $R^2$ and $R^3$ are different, and are a thiazolyl group or a phenyl group having optionally a halogen substituent, and $R^4$ and $R^5$ are the same as defined in the above compound (464), or a salt thereof.

(479) The benzazepine derivative of the above formula [1] wherein $R^1$ is a hydrogen atom, $R^2$ and $R^3$ are different, and are a thiazolyl group or an imidazolyl group having optionally a lower alkyl substituent, and $R^4$ and $R^5$ are the same as defined in the above compound (464), or a salt thereof.

(480) The benzazepine derivative of the above formula [1] wherein $R^1$ is a hydrogen atom, $R^2$ and $R^3$ are different, and are a hydrogen atom or a phenoxy-lower alkyl group, and $R^4$ and $R^5$ are the same as defined in the above compound (464), or a salt thereof.

(481) The benzazepine derivative of the above formula [1] wherein $R^1$ is a hydrogen atom, $R^2$ and $R^3$ are different, and are a lower alkoxy group or a phenoxy-lower alkyl group, and $R^4$ and $R^5$ are the same as defined in the above compound (464), or a salt thereof.

(482) The benzazepine derivative of the above formula [1] wherein $R^1$ is a hydrogen atom, $R^2$ and $R^3$ are different, and are a phenoxy-lower alkyl group, or a lower alkyl group having optionally a lower alkoxy substituent, and $R^4$ and $R^5$ are the same as defined in the above compound (464), or a salt thereof.

(483) The benzazepine derivative of the above formula [1] wherein $R^1$ is a hydrogen atom, $R^2$ and $R^3$ are different, and are a phenoxy-lower alkyl group, or a hydroxy-substituted lower alkyl group, and $R^4$ and $R^5$ are the same as defined in the above compound (464), or a salt thereof.

(484) The benzazepine derivative of the above formula [1] wherein $R^1$ is a hydrogen atom, $R^2$ and $R^3$ are different, and are a phenoxy-lower alkyl group, or an amino-substituted lower alkyl group having optionally a lower alkyl substituent, and $R^4$ and $R^5$ are the same as defined in the above compound (464), or a salt thereof.

(485) The benzazepine derivative of the above formula [1] wherein $R^1$ is a hydrogen atom, $R^2$ and $R^3$ are different, and are a phenoxy-lower alkyl group, or a carbamoyl-substituted lower alkyl group, and $R^4$ and $R^5$ are the same as defined in the above compound (464), or a salt thereof.

(486) The benzazepine derivative of the above formula [1] wherein $R^1$ is a hydrogen atom, $R^2$ and $R^3$ are different, and are a phenoxy-lower alkyl group, or an adamantyl-substituted lower alkyl group, and $R^4$ and $R^5$ are the same as defined in the above compound (464), or a salt thereof.

(487) The benzazepine derivative of the above formula [1] wherein $R^1$ is a hydrogen atom, $R^2$ and $R^3$ are different, and are a phenoxy-lower alkyl group, or a lower alkylsulfonyl group, and $R^4$ and $R^5$ are the same as defined in the above compound (464), or a salt thereof.

(488) The benzazepine derivative of the above formula [1] wherein $R^1$ is a hydrogen atom, $R^2$ and $R^3$ are different, and are a phenoxy-lower alkyl group, or a pyridyl group, and $R^4$ and $R^5$ are the same as defined in the above compound (464), or a salt thereof.

(489) The benzazepine derivative of the above formula [1] wherein $R^1$ is a hydrogen atom, $R^2$ and $R^3$ are different, and are a phenoxy-lower alkyl group, or a pyridyl-lower alkyl group, and $R^4$ and $R^5$ are the same as defined in the above compound (464), or a salt thereof.

(490) The benzazepine derivative of the above formula [1] wherein $R^1$ is a hydrogen atom, $R^2$ and $R^3$ are different, and are a phenoxy-lower alkyl group, or an imidazolyl-lower alkyl group, and $R^4$ and $R^5$ are the same as defined in the above compound (464), or a salt thereof.

(491) The benzazepine derivative of the above formula [1] wherein $R^1$ is a hydrogen atom, $R^2$ and $R^3$ are different, and are a phenoxy-lower alkyl group, or a phenyl group having optionally a halogen substituent, and $R^4$ and $R^5$ are the same as defined in the above compound (464), or a salt thereof.

(492) The benzazepine derivative of the above formula [1] wherein $R^1$ is a hydrogen atom, $R^2$ and $R^3$ are different, and are a phenoxy-lower alkyl group, or an imidazolyl group having optionally a lower alkyl substituent, and $R^4$ and $R^5$ are the same as defined in the above compound (464), or a salt thereof.

(493) The benzazepine derivative of the above formula [1] wherein $R^1$, $R^2$, $R^3$ and $R^4$ are the same as defined in the above compound (464), and $R^5$ is a pyrrolidinyl group, or a salt thereof.

(494) The benzazepine derivative of the above formula [1] wherein $R^1$, $R^2$, $R^3$ and $R^4$ are the same as defined in the above compound (465), and $R^5$ is a pyrrolidinyl group, or a salt thereof.

(495) The benzazepine derivative of the above formula [1] wherein $R^1$, $R^2$, $R^3$ and $R^4$ are the same as defined in the above compound (466), and $R^5$ is a pyrrolidinyl group, or a salt thereof.

(496) The benzazepine derivative of the above formula [1] wherein $R^1$, $R^2$, $R^3$ and $R^4$ are the same as defined in the above compound (467), and $R^5$ is a pyrrolidinyl group, or a salt thereof.

(497) The benzazepine derivative of the above formula [1] wherein $R^1$, $R^2$, $R^3$ and $R^4$ are the same as defined in the above compound (468), and $R^5$ is a pyrrolidinyl group, or a salt thereof.

(498) The benzazepine derivative of the above formula [1] wherein $R^1$, $R^2$, $R^3$ and $R^4$ are the same as defined in the above compound (469), and $R^5$ is a pyrrolidinyl group, or a salt thereof.

(499) The benzazepine derivative of the above formula [1] wherein $R^1$, $R^2$, $R^3$ and $R^4$ are the same as defined in the above compound (470), and $R^5$ is a pyrrolidinyl group, or a salt thereof.

(500) The benzazepine derivative of the above formula [1] wherein $R^1$, $R^2$, $R^3$ and $R^4$ are the same as defined in the above compound (471), and $R^5$ is a pyrrolidinyl group, or a salt thereof.

(501) The benzazepine derivative of the above formula [1] wherein $R^1$, $R^2$, $R^3$ and $R^4$ are the same as defined in the above compound (472), and $R^5$ is a pyrrolidinyl group, or a salt thereof.

(502) The benzazepine derivative of the above formula [1] wherein $R^1$, $R^2$, $R^3$ and $R^4$ are the same as defined in the above compound (473), and $R^5$ is a pyrrolidinyl group, or a salt thereof.
(503) The benzazepine derivative of the above formula [1] wherein $R^1$, $R^2$, $R^3$ and $R^4$ are the same as defined in the above compound (474), and $R^5$ is a pyrrolidinyl group, or a salt thereof.
(504) The benzazepine derivative of the above formula [1] wherein $R^1$, $R^2$, $R^3$ and $R^4$ are the same as defined in the above compound (475), and $R^5$ is a pyrrolidinyl group, or a salt thereof.
(505) The benzazepine derivative of the above formula [1] wherein $R^1$, $R^2$, $R^3$ and $R^4$ are the same as defined in the above compound (476), and $R^5$ is a pyrrolidinyl group, or a salt thereof.
(506) The benzazepine derivative of the above formula [1] wherein $R^1$, $R^2$, $R^3$ and $R^4$ are the same as defined in the above compound (477), and $R^5$ is a pyrrolidinyl group, or a salt thereof.
(507) The benzazepine derivative of the above formula [1] wherein $R^1$, $R^2$, $R^3$ and $R^4$ are the same as defined in the above compound (478), and $R^5$ is a pyrrolidinyl group, or a salt thereof.
(508) The benzazepine derivative of the above formula [1] wherein $R^1$, $R^2$, $R^3$ and $R^4$ are the same as defined in the above compound (479), and $R^5$ is a pyrrolidinyl group, or a salt thereof.
(509) The benzazepine derivative of the above formula [1] wherein $R^1$, $R^2$, $R^3$ and $R^4$ are the same as defined in the above compound (480), and $R^5$ is a pyrrolidinyl group, or a salt thereof.
(510) The benzazepine derivative of the above formula [1] wherein $R^1$, $R^2$, $R^3$ and $R^4$ are the same as defined in the above compound (481), and $R^5$ is a pyrrolidinyl group, or a salt thereof.
(511) The benzazepine derivative of the above formula [1] wherein $R^1$, $R^2$, $R^3$ and $R^4$ are the same as defined in the above compound (482), and $R^5$ is a pyrrolidinyl group, or a salt thereof.
(512) The benzazepine derivative of the above formula [1] wherein $R^1$, $R^2$, $R^3$ and $R^4$ are the same as defined in the above compound (483), and $R^5$ is a pyrrolidinyl group, or a salt thereof.
(513) The benzazepine derivative of the above formula [1] wherein $R^1$, $R^2$, $R^3$ and $R^4$ are the same as defined in the above compound (484), and $R^5$ is a pyrrolidinyl group, or a salt thereof.
(514) The benzazepine derivative of the above formula [1] wherein $R^1$, $R^2$, $R^3$ and $R^4$ are the same as defined in the above compound (485), and $R^5$ is a pyrrolidinyl group, or a salt thereof.
(515) The benzazepine derivative of the above formula [1] wherein $R^1$, $R^2$, $R^3$ and $R^4$ are the same as defined in the above compound (486), and $R^5$ is a pyrrolidinyl group, or a salt thereof.
(516) The benzazepine derivative of the above formula [1] wherein $R^1$, $R^2$, $R^3$ and $R^4$ are the same as defined in the above compound (487), and $R^5$ is a pyrrolidinyl group, or a salt thereof.
(517) The benzazepine derivative of the above formula [1] wherein $R^1$, $R^2$, $R^3$ and $R^4$ are the same as defined in the above compound (488), and $R^5$ is a pyrrolidinyl group, or a salt thereof.
(518) The benzazepine derivative of the above formula [1] wherein $R^1$, $R^2$, $R^3$ and $R^4$ are the same as defined in the above compound (489), and $R^5$ is a pyrrolidinyl group, or a salt thereof.
(519) The benzazepine derivative of the above formula [1] wherein $R^1$, $R^2$, $R^3$ and $R^4$ are the same as defined in the above compound (490), and $R^5$ is a pyrrolidinyl group, or a salt thereof.
(520) The benzazepine derivative of the above formula [1 wherein $R^1$, $R^2$, $R^3$ and $R^4$ are the same as defined in the above compound (491), and $R^5$ is a pyrrolidinyl group, or a salt thereof.
(521) The benzazepine derivative of the above formula [1] wherein $R^1$, $R^2$, $R^3$ and $R^4$ are the same as defined in the above compound (492), and $R^5$ is a pyrrolidinyl group, or a salt thereof.
(522) The benzazepine derivative of the above formula [1] wherein $R^2$, $R^3$, $R^4$ and $R^5$ are the same as defined in the above compound (464), and $R^1$ is a halogen atom, or a salt thereof.
(523) The benzazepine derivative of the above formula [1] wherein $R^2$, $R^3$, $R^4$ and $R^5$ are the same as defined in the above compound (465), and $R^1$ is a halogen atom, or a salt thereof.
(524) The benzazepine derivative of the above formula [1] wherein $R^2$, $R^3$, $R^4$ and $R^5$ are the same as defined in the above compound (466), and $R^1$ is a halogen atom, or a salt thereof.
(525) The benzazepine derivative of the above formula [1] wherein $R^2$, $R^3$, $R^4$ and $R^5$ are the same as defined in the above compound (467), and $R^1$ is a halogen atom, or a salt thereof.
(526) The benzazepine derivative of the above formula [1] wherein $R^2$, $R^3$, $R^4$ and $R^5$ are the same as defined in the above compound (468), and $R^1$ is a halogen atom, or a salt thereof.
(527) The benzazepine derivative of the above formula [1] wherein $R^2$, $R^3$, $R^4$ and $R^5$ are the same as defined in the above compound (469), and $R^1$ is a halogen atom, or a salt thereof.
(528) The benzazepine derivative of the above formula [1] wherein $R^2$, $R^3$, $R^4$ and $R^5$ are the same as defined in the above compound (470), and $R^1$ is a halogen atom, or a salt thereof.
(529) The benzazepine derivative of the above formula [1] wherein $R^2$, $R^{3,}$ $R^4$ and $R^5$ are the same as defined in the above compound (471), and $R^1$ is a halogen atom, or a salt thereof.
(530) The benzazepine derivative of the above formula [1] wherein $R^2$, $R^3$, $R^4$ and $R^5$ are the same as defined in the above compound (472), and $R^1$ is a halogen atom, or a salt thereof.
(531) The benzazepine derivative of the above formula [1] wherein $R^2$, $R^3$, $R^4$ and $R^5$ are the same as defined in the above compound (473), and $R^1$ is a halogen atom, or a salt thereof.
(532) The benzazepine derivative of the above formula [1] wherein $R^2$, $R^3$, $R^4$ and $R^5$ are the same as defined in the above compound (474), and $R^1$ is a halogen atom, or a salt thereof.
(533) The benzazepine derivative of the above formula [1] wherein $R^2$, $R^3$, $R^4$ and $R^5$ are the same as defined in the above compound (475), and $R^1$ is a halogen atom, or a salt thereof.
(534) The benzazepine derivative of the above formula [1] wherein $R^2$, $R^3$, $R^4$ and $R^5$ are the same as defined in the above compound (476), and $R^1$ is a halogen atom, or a salt thereof.
(535) The benzazepine derivative of the above formula [1] wherein $R^2$, $R^3$, $R^4$ and $R^5$ are the same as defined in the above compound (477), and $R^1$ is a halogen atom, or a salt thereof.

(536) The benzazepine derivative of the above formula [1] wherein $R^2$, $R^3$, $R^4$ and $R^5$ are the same as defined in the above compound (478), and $R^1$ is a halogen atom, or a salt thereof.
(537) The benzazepine derivative of the above formula [1] wherein $R^2$, $R^3$, $R^4$ and $R^5$ are the same as defined in the above compound (479), and $R^1$ is a halogen atom, or a salt thereof.
(538) The benzazepine derivative of the above formula [1] wherein $R^2$, $R^3$, $R^4$ and $R^5$ are the same as defined in the above compound (480), and $R^1$ is a halogen atom, or a salt thereof.
(539) The benzazepine derivative of the above formula [1] wherein $R^2$, $R^3$, $R^4$ and $R^5$ are the same as defined in the above compound (481), and $R^1$ is a halogen atom, or a salt thereof.
(540) The benzazepine derivative of the above formula [1] wherein $R^2$, $R^3$, $R^4$ and $R^5$ are the same as defined in the above compound (482), and $R^1$ is a halogen atom, or a salt thereof.
(541) The benzazepine derivative of the above formula [1] wherein $R^2$, $R^3$, $R^4$ and $R^5$ are the same as defined in the above compound (483), and $R^1$ is a halogen atom, or a salt thereof.
(542) The benzazepine derivative of the above formula [1] wherein $R^2$, $R^3$, $R^4$ and $R^5$ are the same as defined in the above compound (484), and $R^1$ is a halogen atom, or a salt thereof.
(543) The benzazepine derivative of the above formula [1] wherein $R^2$, $R^3$, $R^4$ and $R^5$ are the same as defined in the above compound (485), and $R^1$ is a halogen atom, or a salt thereof.
(544) The benzazepine derivative of the above formula [1] wherein $R^2$, $R^3$, $R^4$ and $R^5$ are the same as defined in the above compound (486), and $R^1$ is a halogen atom, or a salt thereof.
(545) The benzazepine derivative of the above formula [1] wherein $R^2$, $R^3$, $R^4$ and $R^5$ are the same as defined in the above compound (487), and $R^1$ is a halogen atom, or a salt thereof.
(546) The benzazepine derivative of the above formula [1] wherein $R^2$, $R^3$, $R^4$ and $R^5$ are the same as defined in the above compound (488), and $R^1$ is a halogen atom, or a salt thereof.
(547) The benzazepine derivative of the above formula [1] wherein $R^2$, $R^3$, $R^4$ and $R^5$ are the same as defined in the above compound (489), and $R^1$ is a halogen atom, or a salt thereof.
(548) The benzazepine derivative of the above formula [1] wherein $R^2$, $R^3$, $R^4$ and $R^5$ are the same as defined in the above compound (490), and $R^1$ is a halogen atom, or a salt thereof.
(549) The benzazepine derivative of the above formula [1] wherein $R^2$, $R^3$, $R^4$ and $R^5$ are the same as defined in the above compound (491), and $R^1$ is a halogen atom, or a salt thereof.
(550) The benzazepine derivative of the above formula [1] wherein $R^2$, $R^3$, $R^4$ and $R^5$ are the same as defined in the above compound (492), and $R^1$ is a halogen atom, or a salt thereof.
(551) The benzazepine derivative of the above formula [1] wherein $R^2$, $R^3$, $R^4$ and $R^5$ are the same as defined in the above compound (493), and $R^1$ is a halogen atom, or a salt thereof.
(552) The benzazepine derivative of the above formula [1] wherein $R^2$, $R^3$, $R^4$ and $R^5$ are the same as defined in the above compound (494), and $R^1$ is a halogen atom, or a salt thereof.
(553) The benzazepine derivative of the above formula [1] wherein $R^2$, $R^3$, $R^4$ and $R^5$ are the same as defined in the above compound (495), and $R^1$ is a halogen atom, or a salt thereof.
(554) The benzazepine derivative of the above formula [1] wherein $R^2$, $R^3$, $R^4$ and $R^5$ are the same as defined in the above compound (496), and $R^1$ is a halogen atom, or a salt thereof.
(555) The benzazepine derivative of the above formula [1] wherein $R^2$, $R^3$, $R^4$ and $R^5$ are the same as defined in the above compound (497), and $R^1$ is a halogen atom, or a salt thereof.
(556) The benzazepine derivative of the above formula [1] wherein $R^2$, $R^3$, $R^4$ and $R^5$ are the same as defined in the above compound (498), and $R^1$ is a halogen atom, or a salt thereof.
(557) The benzazepine derivative of the above formula [1] wherein $R^2$, $R^3$, $R^4$ and $R^5$ are the same as defined in the above compound (499), and $R^1$ is a halogen atom, or a salt thereof.
(558) The benzazepine derivative of the above formula [1] wherein $R^2$, $R^3$, $R^4$ and $R^5$ are the same as defined in the above compound (500), and $R^1$ is a halogen atom, or a salt thereof.
(559) The benzazepine derivative of the above formula [1] wherein $R^2$, $R^3$, $R^4$ and $R^5$ are the same as defined in the above compound (501), and $R^1$ is a halogen atom, or a salt thereof.
(560) The benzazepine derivative of the above formula [1] wherein $R^2$, $R^3$, $R^4$ and $R^5$ are the same as defined in the above compound (502), and $R^1$ is a halogen atom, or a salt thereof.
(561) The benzazepine derivative of the above formula [1] wherein $R^2$, $R^3$, $R^4$ and $R^5$ are the same as defined in the above compound (503), and $R^1$ is a halogen atom, or a salt thereof.
(562) The benzazepine derivative of the above formula [1] wherein $R^2$, $R^3$, $R^4$ and $R^5$ are the same as defined in the above compound (504), and $R^1$ is a halogen atom, or a salt thereof.
(563) The benzazepine derivative of the above formula [1] wherein $R^2$, $R^3$, $R^4$ and $R^5$ are the same as defined in the above compound (505), and $R^1$ is a halogen atom, or a salt thereof.
(564) The benzazepine derivative of the above formula [1] wherein $R^2$, $R^3$, $R^4$ and $R^5$ are the same as defined in the above compound (506), and $R^1$ is a halogen atom, or a salt thereof.
(565) The benzazepine derivative of the above formula [1] wherein $R^2$, $R^3$, $R^4$ and $R^5$ are the same as defined in the above compound (507), and $R^1$ is a halogen atom, or a salt thereof.
(566) The benzazepine derivative of the above formula [1] wherein $R^2$, $R^3$, $R^4$ and $R^5$ are the same as defined in the above compound (508), and $R^1$ is a halogen atom, or a salt thereof.
(567) The benzazepine derivative of the above formula [1] wherein $R^2$, $R^3$, $R^4$ and $R^5$ are the same as defined in the above compound (509), and $R^1$ is a halogen atom, or a salt thereof.
(568) The benzazepine derivative of the above formula [1] wherein $R^2$, $R^3$, $R^4$ and $R^5$ are the same as defined in the above compound (510), and $R^1$ is a halogen atom, or a salt thereof.
(569) The benzazepine derivative of the above formula [1] wherein $R^2$, $R^3$, $R^4$ and $R^5$ are the same as defined in the above compound (511), and $R^1$ is a halogen atom, or a salt thereof.

(570) The benzazepine derivative of the above formula [1] wherein $R^2$, $R^3$, $R^4$ and $R^5$ are the same as defined in the above compound (512), and $R^1$ is a halogen atom, or a salt thereof.
(571) The benzazepine derivative of the above formula [1] wherein $R^2$, $R^3$, $R^4$ and $R^5$ are the same as defined in the above compound (513), and $R^1$ is a halogen atom, or a salt thereof.
(572) The benzazepine derivative of the above formula [1] wherein $R^2$, $R^3$, $R^4$ and $R^5$ are the same as defined in the above compound (514), and $R^1$ is a halogen atom, or a salt thereof.
(573) The benzazepine derivative of the above formula [1] wherein $R^2$, $R^3$, $R^4$ and $R^5$ are the same as defined in the above compound (515), and $R^1$ is a halogen atom, or a salt thereof.
(574) The benzazepine derivative of the above formula [1] wherein $R^2$, $R^3$, $R^4$ and $R^5$ are the same as defined in the above compound (516), and $R^1$ is a halogen atom, or a salt thereof.
(575) The benzazepine derivative of the above formula [1] wherein $R^2$, $R^3$, $R^4$ and $R^5$ are the same as defined in the above compound (517), and $R^1$ is a halogen atom, or a salt thereof.
(576) The benzazepine derivative of the above formula [1] wherein $R^2$, $R^3$, $R^4$ and $R^5$ are the same as defined in the above compound (518), and $R^1$ is a halogen atom, or a salt thereof.
(577) The benzazepine derivative of the above formula [1] wherein $R^2$, $R^3$, $R^4$ and $R^5$ are the same as defined in the above compound (519), and $R^1$ is a halogen atom, or a salt thereof.
(578) The benzazepine derivative of the above formula [1] wherein $R^2$, $R^3$, $R^4$ and $R^5$ are the same as defined in the above compound (520), and $R^1$ is a halogen atom, or a salt thereof.
(579) The benzazepine derivative of the above formula [1] wherein $R^2$, $R^3$, $R^4$ and $R^5$ are the same as defined in the above compound (521), and $R^1$ is a halogen atom, or a salt thereof.
(580) The benzazepine derivative of the above formula [1] wherein $R^1$, $R^2$, $R^3$ and $R^4$ are the same as defined in the above compound (550), and $R^5$ is a pyrrolidinyl group, or a salt thereof.
(581) The benzazepine derivative of the above formula [1] wherein $R^1$, $R^2$, $R^3$ and $R^4$ are the same as defined in the above compound (551), and $R^5$ is a pyrrolidinyl group, or a salt thereof.
(582) The benzazepine derivative of the above formula [1] wherein $R^1$, $R^2$, $R^3$ and $R^4$ are the same as defined in the above compound (552), and $R^5$ is a pyrrolidinyl group, or a salt thereof.
(583) The benzazepine derivative of the above formula [1] wherein $R^1$, $R^2$, $R^3$ and $R^4$ are the same as defined in the above compound (553), and $R^5$ is a pyrrolidinyl group, or a salt thereof.
(584) The benzazepine derivative of the above formula [1] wherein $R^1$, $R^2$, $R^3$ and $R^4$ are the same as defined in the above compound (554), and $R^5$ is a pyrrolidinyl group, or a salt thereof.
(585) The benzazepine derivative of the above formula [1] wherein $R^1$, $R^2$, $R^3$ and $R^4$ are the same as defined in the above compound (555), and $R^5$ is a pyrrolidinyl group, or a salt thereof.
(586) The benzazepine derivative of the above formula [1] wherein $R^1$, $R^2$, $R^3$ and $R^4$ are the same as defined in the above compound (556), and $R^5$ is a pyrrolidinyl group, or a salt thereof.
(587) The benzazepine derivative of the above formula [1] wherein $R^1$, $R^2$, $R^3$ and $R^4$ are the same as defined in the above compound (557), and $R^5$ is a pyrrolidinyl group, or a salt thereof.
(588) The benzazepine derivative of the above formula [1] wherein $R^1$, $R^2$, $R^3$ and $R^4$ are the same as defined in the above compound (558), and $R^5$ is a pyrrolidinyl group, or a salt thereof.
(589) The benzazepine derivative of the above formula [1] wherein $R^1$, $R^2$, $R^3$ and $R^4$ are the same as defined in the above compound (559), and $R^5$ is a pyrrolidinyl group, or a salt thereof.
(590) The benzazepine derivative of the above formula [1] wherein $R^1$, $R^2$, $R^3$ and $R^4$ are the same as defined in the above compound (560), and $R^5$ is a pyrrolidinyl group, or a salt thereof.
(591) The benzazepine derivative of the above formula [1] wherein $R^1$, $R^2$, $R^3$ and $R^4$ are the same as defined in the above compound (561), and $R^5$ is a pyrrolidinyl group, or a salt thereof.
(592) The benzazepine derivative of the above formula [1] wherein $R^1$, $R^2$, $R^3$ and $R^4$ are the same as defined in the above compound (562), and $R^5$ is a pyrrolidinyl group, or a salt thereof.
(593) The benzazepine derivative of the above formula [1] wherein $R^1$, $R^2$, $R^3$ and $R^4$ are the same as defined in the above compound (563), and $R^5$ is a pyrrolidinyl group, or a salt thereof.
(594) The benzazepine derivative of the above formula [1] wherein $R^1$, $R^2$, $R^3$ and $R^4$ are the same as defined in the above compound (564), and $R^5$ is a pyrrolidinyl group, or a salt thereof.
(595) The benzazepine derivative of the above formula [1] wherein $R^1$, $R^2$, $R^3$ and $R^4$ are the same as defined in the above compound (565), and $R^5$ is a pyrrolidinyl group, or a salt thereof.
(596) The benzazepine derivative of the above formula [1] wherein $R^1$, $R^2$, $R^3$ and $R^4$ are the same as defined in the above compound (566), and $R^5$ is a pyrrolidinyl group, or a salt thereof.
(597) The benzazepine derivative of the above formula [1] wherein $R^1$, $R^2$, $R^3$ and $R^4$ are the same as defined in the above compound (567), and $R^5$ is a pyrrolidinyl group, or a salt thereof.
(598) The benzazepine derivative of the above formula [1] wherein $R^1$, $R^2$, $R^3$ and $R^4$ are the same as defined in the above compound (568), and $R^5$ is a pyrrolidinyl group, or a salt thereof.
(599) The benzazepine derivative of the above formula [1] wherein $R^1$, $R^2$, $R^3$ and $R^4$ are the same as defined in the above compound (569), and $R^5$ is a pyrrolidinyl group, or a salt thereof.
(600) The benzazepine derivative of the above formula [1] wherein $R^1$, $R^2$, $R^3$ and $R^4$ are the same as defined in the above compound (570), and $R^5$ is a pyrrolidinyl group, or a salt thereof.
(601) The benzazepine derivative of the above formula [1] wherein $R^1$, $R^2$, $R^3$ and $R^4$ are the same as defined in the above compound (571), and $R^5$ is a pyrrolidinyl group, or a salt thereof.
(602) The benzazepine derivative of the above formula [1] wherein $R^1$, $R^2$, $R^3$ and $R^4$ are the same as defined in the above compound (572), and $R^5$ is a pyrrolidinyl group, or a salt thereof.
(603) The benzazepine derivative of the above formula [1] wherein $R^1$, $R^2$, $R^3$ and $R^4$ are the same as defined in the above compound (573), and $R^5$ is a pyrrolidinyl group, or a salt thereof.

(604) The benzazepine derivative of the above formula [1] wherein $R^1$, $R^2$, $R^3$ and $R^4$ are the same as defined in the above compound (574), and $R^5$ is a pyrrolidinyl group, or a salt thereof.
(605) The benzazepine derivative of the above formula [1] wherein $R^1$, $R^2$, $R^3$ and $R^4$ are the same as defined in the above compound (575), and $R^5$ is a pyrrolidinyl group, or a salt thereof.
(606) The benzazepine derivative of the above formula [1] wherein $R^1$, $R^2$, $R^3$ and $R^4$ are the same as defined in the above compound (576), and $R^5$ is a pyrrolidinyl group, or a salt thereof.
(607) The benzazepine derivative of the above formula [1] wherein $R^1$, $R^2$, $R^3$ and $R^4$ are the same as defined in the above compound (577), and $R^5$ is a pyrrolidinyl group, or a salt thereof.
(608) The benzazepine derivative of the above formula [1] wherein $R^1$, $R^2$, $R^3$ and $R^4$ are the same as defined in the above compound (578), and $R^5$ is a pyrrolidinyl group, or a salt thereof.
(609) The benzazepine derivative of the above formula [1] wherein $R^1$, $R^2$, $R^3$ and $R^4$ are the same as defined in the above compound (579), and $R^5$ is a pyrrolidinyl group, or a salt thereof.

Among the benzazepine derivatives of the present invention, the preferable compound is the compound of the formula [1] wherein $R^1$ is a hydrogen atom or a halogen atom, $R^2$ and $R^3$ are different, and are a hydrogen atom or a lower alkyl group, or $R^2$ and $R^3$ combine together with the nitrogen atom to which they bond to form a 5- to 7-membered saturated heterocyclic group which may be intervened or not with another nitrogen atom or an oxygen atom, wherein said heterocyclic group may optionally be substituted by a lower alkyl group, $R^4$ is a halogen atom or a lower alkyl group, $R^5$ is a pyrrolidinyl group.

Moreover, among the benzazepine derivatives of the present invention, the further preferable compound is an optionally active benzazepine compound of the formula [1], i.e. a benzazepine compound of the formula [1b]:

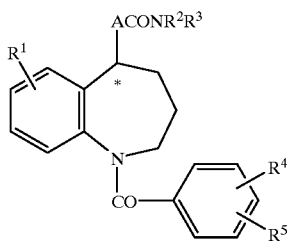

[1b]

wherein $R^1$, $R^2$, $R^3$, $R^4$, $R^5$ and A are the same as defined above, and especially an optically active benzazepine derivative of the formula [1b] wherein $R^4$ is a hydrogen atom, a halogen atom, a lower alkyl group or a lower alkoxy group, $R^5$ is a pyrrolidinyl group, $R^2$ and $R^3$ are the same or different and each are a hydrogen atom or a lower alkyl group having optionally a lower alkoxy substituent, or $R^2$ and $R^3$ combine together with the nitrogen atom to which they bond to form a 5- to 7-membered saturated heterocyclic group which may be intervened or not with another nitrogen atom or an oxygen atom, wherein said heterocyclic group may optionally be substituted by a lower alkyl group or a phenyl-lower alkyl group.

The benzazepine derivatives of the present invention can be prepared by the following processes.

Reaction Scheme-1

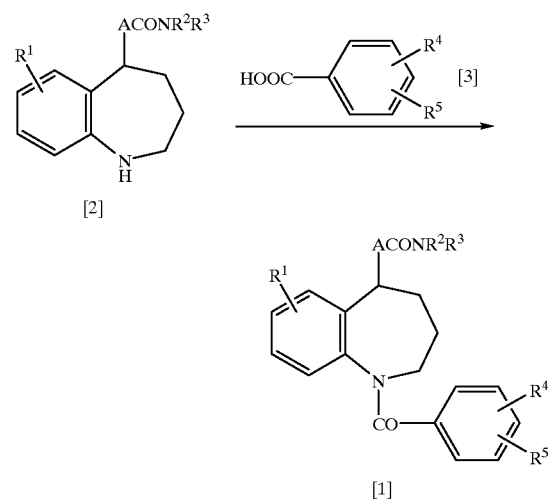

wherein $R^1$, $R^2$, $R^3$, $R^4$, $R^5$ and A are the same as defined above.

The process of Reaction Scheme-1 is carried out by reacting a benzoheterocyclic compound of the formula [2] and a carboxylic acid compound of the formula [3] by the conventional amido bond producing reaction. The amido bond producing reaction can be carried out under the conditions for the conventional amido bond producing reaction, for example, (a) a mixed acid anhydride process, i.e. a process of reacting the carboxylic acid compound [3] with an alkyl halocarbonate ester to form a mixed acid anhydride and reacting the resultant with the amine compound [2], (b) an activated ester process, i.e. a process of converting the carboxylic acid compound [3] into an activated ester such as p-nitrophenyl ester, N-hydroxysuccinimide ester, 1-hydroxybenzotriazole ester, etc., and reacting the resultant with the amine compound [2], (c) a carbodiimide process, i.e. a process of condensing the carboxylic acid compound [3] and the amine compound [2] in the presence of an activating agent such as dicyclohexylcarbodiimide, carbonyldiimidazole, etc., (d) other processes, i.e. a process of converting the carboxylic acid compound [3] into a carboxylic anhydride by treating it with a dehydrating agent such as acetic anhydride, and reacting the resultant with the amine compound [2]; a process of reacting an ester of the carboxylic acid compound [3] with a lower alcohol and the amine compound [2] at a high temperature under high pressure; a process of reacting an acid halide compound of the carboxylic acid compound [3], i.e. a carboxylic acid halide, with the amine compound [2], and the like.

The mixed acid anhydride used in the above mixed acid anhydride process (a) is obtained by the known Schötten-Baumann reaction, and the reaction product is used without isolating from the reaction mixture for the reaction with the amine compound [2] to give the desired compound [1] of the present invention. The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, 1-methylpyrrolidone, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature from −20° C. to about 100° C., preferably at a temperature from 0° C. to about 50° C., for about 5 minutes to about 10 hours, preferably for 5 minutes to about 2 hours.

The reaction between the mixed acid anhydride thus obtained and the amine compound [2] is usually carried out at a temperature from −20° C. to about 150° C., preferably at a temperature from 10° C. to about 50° C., for 5 minutes to about 10 hours, preferably for 5 minutes to about 5 hours. The mixed acid anhydride process is usually carried out in a solvent. The solvent may be any conventional solvents which are usually used in the mixed acid anhydride process and includes, for example, halogenated hydrocarbons (e.g. chloroform, dichloromethane, dichloroethane, etc.), aromatic hydrocarbons (e.g. benzene, p-chlorobenzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, acetonitrile, hexamethylphosphoric triamide, etc.), or a mixture of these solvents. The alkyl halocarbonate ester used in the mixed acid anhydride process includes, for example, methyl chloroformate, methyl bromoformate, ethyl chloroformate, ethyl bromoformate, isobutyl chloroformate, pivaloyl chloride, and the like. In said process, the carboxylic acid compound [3], the alkyl halocarbonate ester and the amine compound [2] are usually used in each equimolar amount, but preferably, the alkyl halocarbonate ester and the carboxylic acid compound [3] are used each in an amount of about 1 to 1.5 mole, to 1 mole of the amine compound [2].

Among the above other processes (d), in case of the process of reacting the carboxylic acid halide with the amine compound [2], the reaction is usually carried out in the presence of a basic compound in an appropriate solvent. The basic compound is any conventional compounds and includes, for example, in addition to the basic compounds used for the above Schötten-Baumann reaction, sodium hydroxide, potassium hydroxide, sodium hydride, potassium hydride, and the like. The solvent includes, for example, in addition to the solvents used in the mixed acid anhydride process, alcohols (e.g. methanol, ethanol, propanol, butanol, 3-methoxy-1-butanol, ethylcellosolve, methylcellosolve, etc.), pyridine, acetone, water, and the like. The amount of the amine compound [2] and the carboxylic acid halide is not critical, but the carboxylic acid halide is usually used at least in equimolar amount, preferably in an amount of about 1 to 5 moles to 1 mole of the amine compound [2]. The reaction is usually carried out at a temperature from about −20° C. to about 180° C., preferably at a temperature from 0° C. to about 150° C., for about 5 minutes to about 30 hours.

The amido bond producing reaction in the above Reaction Scheme-1 may also be carried out by reacting the carboxylic acid compound [3] and the amine compound [2] in the presence of a condensing agent such as phosphorus compounds (e.g. phenylphosphine-2,2'-dithiodipyridine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, etc.

The reaction is usually carried out in the presence of the solvent and the basic compound as used in the above reaction of the carboxylic acid halide and the amine compound [2] at a temperature from −20° C. to about 150° C., preferably at a temperature from 0° C. to about 100° C., for about 5 minutes to about 30 hours. The condensing agent and the carboxylic acid compound [3] are used at least in equimolar amount, preferably in an amount of about 1 to 2 moles, to 1 mole of the amine compound [2].

Reaction Scheme-2

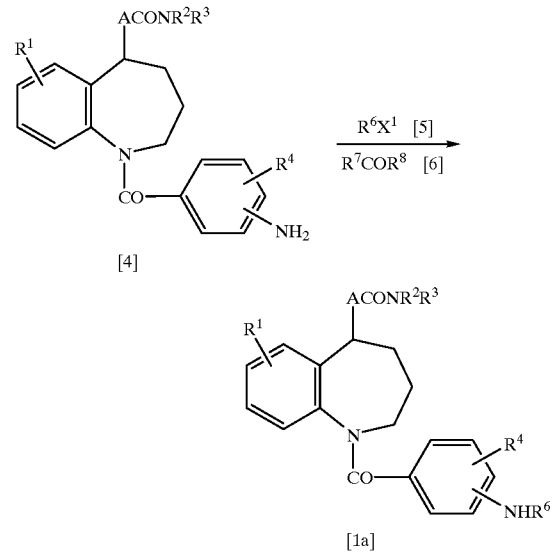

wherein $R^1$, $R^2$, $R^3$, $R^4$, $R^6$ and A are the same as defined above, $X^1$ is a halogen atom, and $R^7$ and $R^8$ are each a hydrogen atom or a lower alkyl group.

The reaction of the compound [4] and the compound [5] is carried out in the presence or absence of a basic compound in an appropriate inert solvent. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, t-butanol, etc.), acetic acid, ethyl acetate, acetone, acetonitrile, pyridine, dimethyl sulfoxide, dimethylformamide, hexamethylphosphoric triamide, or a mixture of these solvents. The basic compound includes, for example, alkali metal carbonates or hydrogen carbonates (e.g. sodium carbonate, potassium carbonate, sodium hydrogen carbonate, potassium hydrogen carbonate, etc.), alkali metal hydroxides (e.g. sodium hydroxide, potassium hydroxide, etc.), sodium hydride, potassium, sodium, sodium amide, alkali metal alcoholates (e.g. sodium methylate, sodium ethylate, etc.), organic bases (e.g. pyridine, N-ethyldiisopropylamine, dimethylaminopyridine, triethylamine, 1,5-diazabicyclo[4.3.0]nonene-5 (DBU), 1,8-diazabicyclo[5.4.0]undecene-7 (DBN), 1,4-diazabicyclo[2.2.2]octane (DABCO), etc.), and the like. The amount of the compound [4] and the compound [5] is not critical, but the compound [5] is usually used at least in an equimolar amount, preferably in an amount of 1 to 10 moles, to 1 mole of the compound [4]. The reaction is usually carried out at a temperature from 0° C. to about 200° C., preferably at a temperature from 0° C. to about 170° C., for 30 minutes to about 75 hours. There may be added an alkali metal halide such as sodium iodide, potassium iodide, etc., or copper powder into the reaction system.

The reaction of the compound [4] and the compound [6] is carried out in the presence of a reducing agent, in an appropriate solvent or without a solvent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, ammonium formate, alkali metal salts of fatty acids (e.g. sodium formate, etc.), hydrogenation agents (e.g. sodium borohydride, sodium cyanoborohydride, lithium aluminum hydride, etc.), catalytic reducing agents (e.g. palladium-black, palladium-carbon, platinum oxide, platinum black, Ranney nickel, etc.), and the like.

When formic acid is used as a reducing agent, the reaction is usually carried out at a temperature from room temperature to about 200° C., preferably at a temperature from about 50° C. to about 150° C. for about one hour to about 10 hours. Formic acid is used in an excess amount, to the amount of the compound [4].

When a hydrogenation agent is used, the reaction is usually carried out at a temperature from about −30° C. to about 100° C., preferably at a temperature from 0° C. to about 700° C., for about 30 minutes to about 12 hours. The hydrogenation agent is used in an amount of 1 mole to 20 moles, preferably in an amount of 1 mole to 6 moles, to 1 mole of the compound [4]. Especially, when lithium aluminum hydride is used as a reducing agent, the solvent is preferably ethers (e.g. diethyl ether, dioxane, tetrahydrofuran, diglyme, etc.) or aromatic hydrocarbons (e.g. benzene, toluene, xylene, etc.).

Moreover, when a catalytic reducing agent is used, the reaction is usually carried out under atmospheric pressure to about 20 atms of hydrogen gas, preferably, under atmospheric pressure to about 10 atms of hydrogen gas, or in the presence of a hydrogen donor such as formic acid, ammonium formate, cyclohexene, hydrazine hydrate, etc., at a temperature from −30° C. to about 100° C., preferably at a temperature from 0° C. to about 60° C., for about one hour to about 12 hours. The catalytic reducing agent is usually used in an amount of 0.1 to 40% by weight, preferably in an amount of 1 to 20% by weight, to the amount of the compound [4]. The hydrogen donor is usually used in an excess amount to the amount of the compound [4]. The compound [6] is usually used at least in equimolar amount, preferably in an amount of equimolar to excess amount, to 1 mole of the compound [4].

Reaction Scheme-3

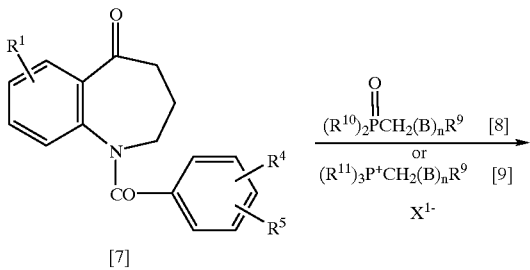

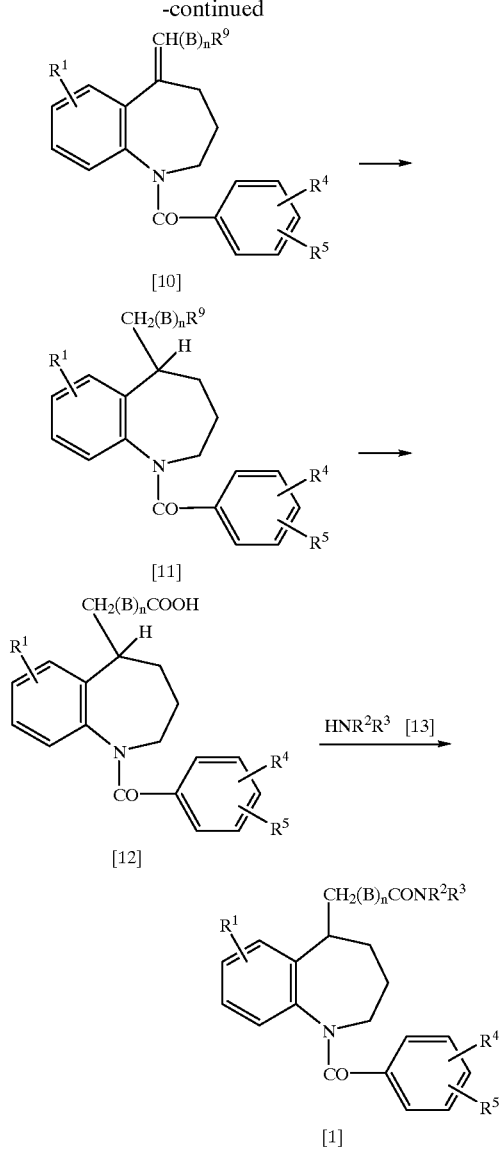

wherein $R^1$, $R^2$, $R^{3,}$ $R^4$, $R^5$ and $X^1$ are the same as defined above, $R^9$ is a lower alkoxycarbonyl group, $R^{10}$ is a lower alkoxy group, B is a lower alkylene group, n is 0 or 1, and $R^{11}$ is a phenyl group.

The reaction of the compound [7] and the compound [8] or the compound [9] is carried out in the presence of a basic compound in an appropriate solvent. The basic compound includes, for example, inorganic bases such as sodium, potassium, sodium hydride, sodium amide, sodium hydroxide, potassium hydroxide, sodium carbonate, potassium carbonate, sodium hydrogen carbonate, etc., and organic bases such as metal alcoholates (e.g. sodium methylate, sodium ethylate, potassium t-butoxide, etc.), alkyl lithium, aryl lithium or lithium amide (e.g. methyl lithium, n-butyl lithium, phenyl lithium, lithium diisopropylamide, etc.), pyridine, piperidine, quinoline, triethylamine, N,N-dimethylaniline, and the like. The solvent may be any one which does not affect the reaction, and includes, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethyl-formamide, dimethyl sulfoxide, hexamethylphosphoric triamide, etc.), alcohols (e.g. methanol, ethanol, isopropanol, etc.), and the like. The reaction is usually carried out at a temperature from −80° C. to 150° C., preferably at a temperature from −80° C. to about 120° C., for 0.5 hour to about 15 hours. The compound [8] or the compound [9] is used at least in equimolar amount, preferably in an amount of 1 to 5 moles, to 1 mole of the compound [7].

The reaction of converting the compound [10] into the compound [11] is carried out by reduction reaction. The reduction reaction is carried out by various methods, for example, by catalytic hydrogenation in the presence of a catalyst in an appropriate solvent. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium-black, palladium-carbon, platinum, platinum oxide, copper chromite, Ranney nickel, and the like. The catalyst is usually used in an amount of 0.02 to 1 mole, to 1 mole of the starting compound. The reaction is usually carried out at a temperature from −20° C. to about 100° C., preferably at a temperature from 0° C. to about 70° C., under a pressure of 1 atm to 10 atms of hydrogen gas, for 0.5 hour to about 20 hours.

The reduction reaction may be carried out under the above reduction conditions, but preferably carried out by using a hydrogenation agent. The hydrogenation agent includes, for example, lithium aluminum hydride, sodium borohydride, sodium cyanoborohydride, diborane, and the like. The hydrogenation agent is used at least in an amount of 0.1 mole, preferably in an amount of 0.1 mole to 10 moles, to 1 mole of the compound [10]. The reduction reaction is usually carried out in an appropriate solvent such as water, lower alcohols (e.g. methanol, ethanol, isopropanol, etc.), ethers (e.g. tetrahydrofuran, diethyl ether, diglyme, etc.), dimethylformamide, or a mixture thereof, at a temperature from −60° C. to 50° C., preferably at a temperature from −30° C. to room temperature, for about 10 minutes to about 5 hours. In case that lithium aluminum hydride or diborane is used as a reducing agent, it is preferable to use an anhydrous solvent such as diethyl ether, tetrahydrofuran, diglyme, and the like.

When a hydrogenation reducing agent is used, an alkali metal halide such as nickel chloride, etc. may be added into the reaction system in order to promote the reaction.

The compound [10] may also be converted into the compound [11] by reducing the compound [10] with using magnesium-methanol. The reaction is usually carried out at a temperature from 0° C. to 50° C., preferably at a temperature from 0° C. to room temperature, for about one hour to 10 hours. Metal magnesium is usually used in an amount of 1 to 10 moles, preferably in an amount of 2 to 7 moles, to 1 mole of the compound [10].

The reaction of converting the compound [11] into the compound [12] is carried out in the presence of an acid or a basic compound, in an appropriate solvent or without a solvent. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The basic compound includes, for example, metal carbonates (e.g. sodium carbonate, potassium carbonate, etc.), metal hydroxides (e.g. sodium hydroxide, potassium hydroxide, calcium hydroxide, lithium hydroxide, etc.), and the like. The reaction is usually carried out at a temperature from room temperature to about 200° C., preferably at a temperature from room temperature to about 150° C., for 10 minutes to about 25 hours.

The compound [12] may also be prepared by treating the compound [11] in an appropriate solvent in the presence of a dialkyl sulfide-Lewis acid such as dimethyl sulfide-aluminum chloride, etc. The solvent may be the same solvents as those used in the reaction of the compound [4] and the compound [5] in the above Reaction Scheme-2. The reaction is usually carried out at a temperature from 0° C. to about 70° C., preferably at a temperature from 0° C. to about 50° C., for one hour to 10 hours.

The reaction of the compound [12] and the compound [13] is carried out under the same conditions as those in the reaction of the compound [2] and the compound [3] in the above Reaction Scheme-1.

The starting compound [4] in the above Reaction Scheme-2 is prepared, for example, by the following Reaction Scheme-4.

Reaction Scheme-4

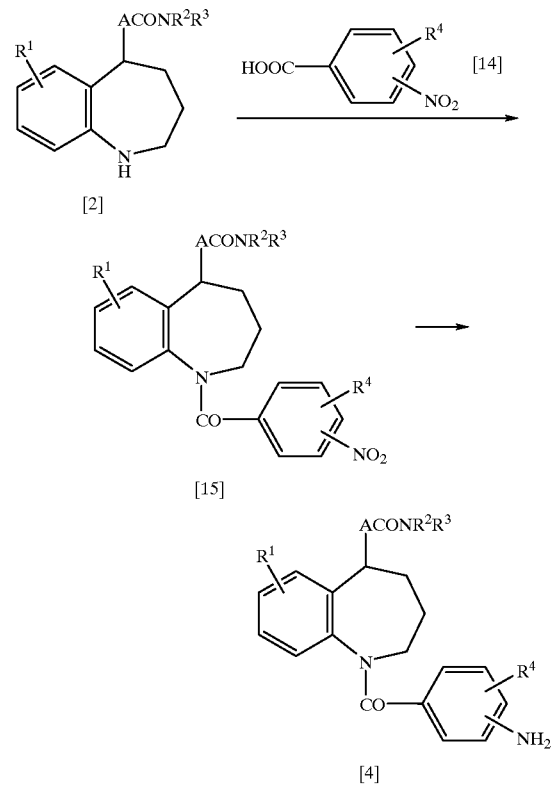

wherein $R^1$, $R^2$, $R^3$, $R^4$ and A are the same as defined above.

The reaction of the compound [2] and the compound [14] is carried out under the same conditions as those in the reaction of the compound [2] and the compound [3] in the above Reaction Scheme-1.

The reaction of converting the compound [15] into the compound [4] is carried out (i) by using a reducing catalyst in an appropriate solvent, or (ii) by using a mixture of a metal or a metal salt and an acid, or a mixture of a metal or a metal salt and an alkali metal hydroxide, sulfide, ammonium salt, etc., as a reducing agent in an appropriate inert solvent.

When the method (i) is employed, the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethyl-formamide, etc.), or a mixture of these solvents. The reducing catalyst includes, for example, palladium, palladium-black, palladium-carbon, platinum, platinum oxide, copper chromite, Ranney nickel, and the like. The catalyst is usually used in an amount of 0.02 to 1 time, to the amount of the starting compound. The reaction is usually carried out at a temperature from about −20° C. to about 150° C., preferably at a temperature from 0° C. to about 100° C., under a pressure of 1 atm to 10 atms of hydrogen gas, for 0.5 hour to about 10 hours. An acid (e.g. hydrochloric acid, etc.) may be added to the reaction system.

When the method (ii) is employed, there is used as a reducing agent a mixture of iron, zinc, tin or stannous chloride and a mineral acid (e.g. hydrochloric acid, sulfuric acid, etc.), or a mixture of iron, iron sulfide, zinc or tin and an alkali metal hydroxide (e.g. sodium hydroxide, etc.), sulfide (e.g. ammonium sulfide, etc.), aqueous ammonia, ammonium salt (e.g. ammonium chloride, etc.). The inert solvent includes, for example, water, acetic acid, methanol, ethanol, dioxane, and the like. The conditions for reduction can be selected according to the kinds of the reducing agent to be used. For example, when a mixture of stannous chloride and hydrochloric acid is used as a reducing agent, the reaction is preferably carried out at a temperature from 0° C. to about 80° C., for 0.5 hour to about 10 hours. The reducing agent may be used at least in equimolar amount, usually in an amount of 1 mole to 5 moles, to 1 mole of the starting compound.

Optically active benzazepine compound of the formula [1-i]

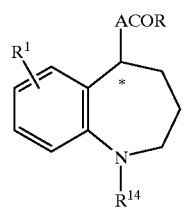

[1-i]

wherein $R^1$, A, R, $R^{14}$ are the same as defined above, which is a very important intermediate for the optically active benzazepine compound [1], may be prepared by the following processes.

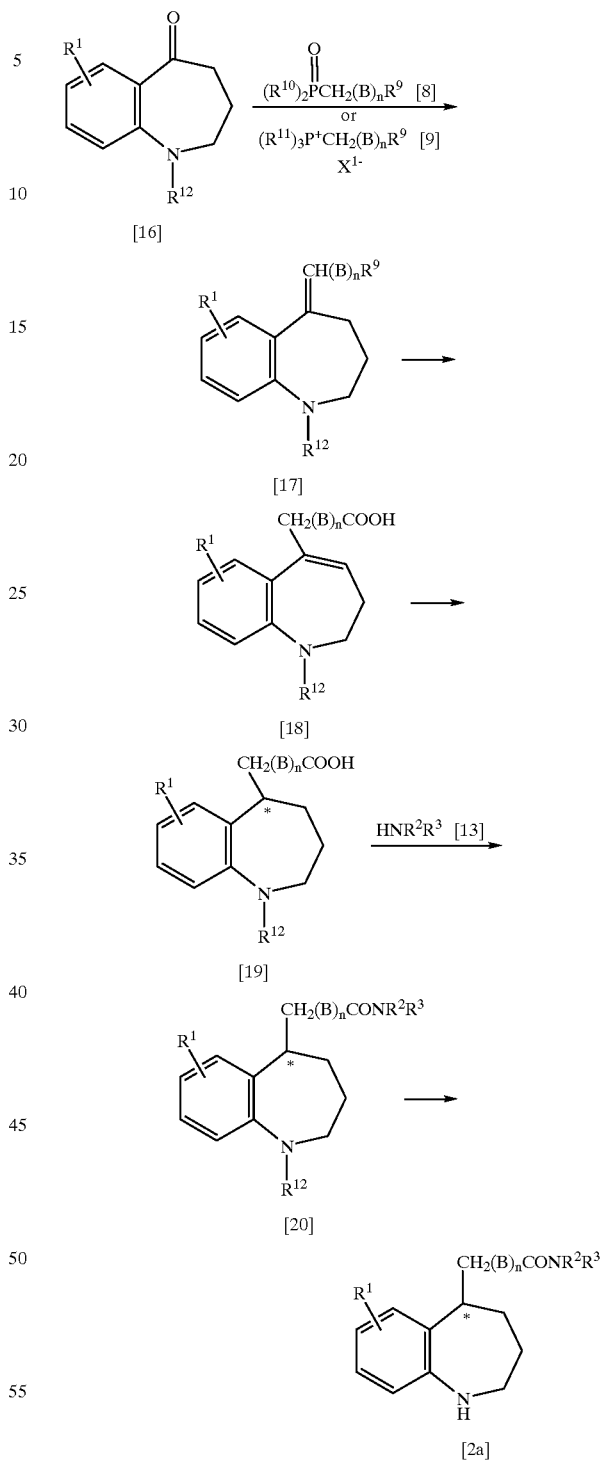

wherein $R^1$, $R^2$, $R^3$, $R^9$, $R^{10}$, $R^{11}$, $X^1$, B and n are the same as defined above, and $R^{12}$ is a phenylsulfonyl group having optionally a lower alkyl substituent on the phenyl ring.

The reaction of the compound [16] and the compound [8] or the compound [9] is carried out in the presence of a basic compound in an appropriate solvent. The basic compound includes, for example, inorganic bases such as sodium, potassium, sodium hydride, sodium amide, sodium hydroxide, potassium hydroxide, sodium carbonate, potassium carbonate, sodium hydrogen carbonate, etc., and organic bases such as metal alcoholates (e.g. sodium methylate, sodium ethylate, potassium t-butoxide, etc.), alkyl lithium, aryl lithium or lithium amide (e.g. methyl lithium, n-butyl lithium, phenyl lithium, lithium diisopropylamide, etc.), pyridine, piperidine, quinoline, triethylamine, N,N-dimethylaniline, and the like. The solvent may be any one which does not affect the reaction, and includes, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc), aprotic polar solvents (e.g., N,N-dimethylformamide, dimethyl sulfoxide, hexamethylphosphoric triamide, etc.), alcohols (e.g. methanol, ethanol, isopropanol, etc.), and the like. The reaction is usually carried out at a temperature from −80° C. to 150° C., preferably at a temperature from −80° C. to about 120° C., for 0.5 hour to about 15 hours. The compound [8] or the compound [9] is usually used at least in equimolar amount, preferably in an amount of 1 to 5 moles, to 1 mole of the compound [16].

The reaction of converting the compound [17] into the compound [18] is carried out in the presence of a basic compound, in an appropriate solvent. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. Among these solvent, methanol is especially preferable. The basic compound includes, for example, metal carbonates (e.g. sodium carbonate, potassium carbonate, etc.), metal hydroxides (e.g. sodium hydroxide, potassium hydroxide, calcium hydroxide, lithium hydroxide, etc.), and the like. The reaction is usually carried out at a temperature from room temperature to about 150° C., preferably at a temperature from room temperature to about 100° C., for 1 minute to about 25 hours.

The reaction of converting the compound [18] into the compound [19] is carried out by reduction reaction. The reduction reaction is carried out by various methods, for example, by catalytic hydrogenation in the presence of a catalyst in an appropriate solvent. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), halogenated hydrocarbons (e.g. dichloromethane, chloroform, carbon tetrachloride, etc.), aprotic polar solvents (e.g. dimethylformamide, etc.), or a mixture of these solvents. The catalyst includes, for example, the compounds as listed below.

(a) Y-(S)-BINAP ((S)-BINAP; (S)-2,2'-bis(diphenylphosphino)-1,1'-binaphthyl)
(b) Y-(R)-BINAP
(c) Y-(S)-H$_8$-BINAP ((S)-H$_8$-BINAP; (S)-2,2'-bis(diphenylphosphino)-5,5',6,6',7,7',8,8'-octahydro-1,1'-binaphthyl)
(d) Y-(R)-H$_8$-BINAP
(e) Y-(R)-(S)-BPPFA ((R)-(S)-BPPFA; (R)-N,N-dimethyl-1-[(S)-1',2'-bis(diphenylphosphino)ferrocenyl]ethylamine)
(f) Y-(+)-DIOP ((+)-DIOP; (+)-2,3-O-isopropylidene-2,3-dihydroxy-1,4-bis(diphenylphosphino)butane)
(g) Y-(−)-NORPHOS ((−)-NORPHOS; (2R,3R)-(−)-2,3-bis(diphenylphosphino)-bicyclo[2.2.1]hepto-5-ene)
(h) Y-(S,S)-CHIRAPHOS ((S,S)-CHIRAPHOS; (2S,3S)-(−)-bis(diphenylphosphino)butane)
(i) Y-(S,S)-ET-DUPHOS ((S,S)-ET-DUPHOS; (+)-1,2-bis((2S,5S)-2,5-diethylphosphorano)benzene)
(j) Y-(S)-PYBOX ((S)-PYBOX; 2,6-bis((4S)-isopropyl-2-oxazolin-2-yl)pyridine)
(k) Y-(+)-NORPHOS ((+)-NORPHOS; (2S,3S)-(+)-2,3-bis(diphenylphosphino)-bicyclo[2.2.1]hepto-5-ene)
(l) Y-(R,R)-ET-DUPHOS ((R,R)-ET-DUPHOS; (−)-1,2-bis((2R,5R)-2,5-diethylphosphorano)benzene)

In the above compounds (a) to (l), Y means a transition metal such as Ru (II), Rh (I), etc., and these metals may be coordinated with a halogen atom such as chlorine atom, etc., a group of the formula: —OR$^{15}$ (R$^{15}$ is a lower alkanoyl group), a cycloalkenyl group such as cyclooctadiene, etc., or benzene, etc., based on the coordination capacity of these metals.

The above catalyst is usually used in an amount of 0.001 to 1 time, to the amount of the starting compound. The reaction is usually carried out at a temperature from −20° C. to about 100° C., preferably at a temperature from room temperature to about 100° C., under a pressure of 1 atm to 150 atms of hydrogen gas, for 0.5 hour to about 50 hours.

By the reduction reaction, there is obtained stereoselectively, safely and in easy and simple procedures, in high purity and high yield, the compound [19] either in the form of (S)-isomer, or in the form of (R)-isomer, based on the stereostructure of the catalyst to be used, under moderate reaction conditions.

The reaction of the compound [19] and the compound [13] is carried out by the conventional amido bond producing reaction. The amido bond producing reaction can be carried out under the conditions for the conventional amido bond producing reaction, for example, (a) a mixed acid anhydride process, i.e. a process of reacting the carboxylic acid compound [19] with an alkyl halocarbonate ester to form a mixed acid anhydride and reacting the resultant with the amine compound [13], (b) an activated ester process, i.e. a process of converting the carboxylic acid compound [19] into an activated ester such as p-nitrophenyl ester, N-hydroxysuccinimide ester, 1-hydroxybenzotriazole ester, etc., and reacting the resultant with the amine compound [13], (c) a carbodiimide process, i.e. a process of condensing the carboxylic acid compound [19] and the amine compound [13] in the presence of an activating agent such as dicyclohexylcarbodiimide, carbonyldiimidazole, etc., (d) other processes, i.e. a process of converting the carboxylic acid compound [19] into a carboxylic anhydride by treating it with a dehydrating agent such as acetic anhydride, and reacting the resultant with the amine compound [13]; a process of reacting an ester of the carboxylic acid compound [19] with a lower alcohol and the amine compound [13] at a high temperature under high pressure; a process of reacting an acid halide compound of the carboxylic acid compound [19], i.e. a carboxylic acid halide, with the amine compound [13], and the like.

The mixed acid anhydride used in the above mixed acid anhydride process (a) is obtained by the known Schötten-Baumann reaction, and the reaction product is used without isolating from the reaction mixture for the reaction with the amine compound [13] to give the compound [20].

The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, 4-dimethylaminopyridine, dimethylaniline, N-methylmorpholine, 1,5-diazabicyclo[4.3.0]-nonene-5 (DBN), 1,8-diazabicyclo[5.4.0]undecene-7 (DBU), 1,4-diazabicyclo-[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature from −20° C. to about 100° C., preferably at a temperature from 0° C. to about 50° C., for about 5 minutes to about 10 hours, preferably for 5 minutes to about 2 hours.

The reaction between the mixed acid anhydride thus obtained and the amine compound [13] is usually carried out at a temperature from −20° C. to about 150° C., preferably at a temperature from 10° C. to about 50° C., for 5 minutes to about 10 hours, preferably for 5 minutes to about 5 hours. The mixed acid anhydride process is usually carried out in a solvent. The solvent may be any conventional solvents which are usually used in the mixed acid anhydride process, and includes, for example, halogenated hydrocarbons (e.g. chloroform, dichloromethane, dichloroethane, etc.), aromatic hydrocarbons (e.g. benzene, p-chlorobenzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, acetonitrile, hexamethylphosphoric triamide, etc.), or a mixture of these solvents. The alkyl halocarbonate ester used in the mixed acid anhydride process includes, for example, methyl chloroformate, methyl bromoformate, ethyl chloroformate, ethyl bromoformate, isobutyl chloroformate, pivaloyl chloride, and the like. In said process, the carboxylic acid compound [19], the alkyl halocarbonate ester and the amine compound [13] are usually used in each equimolar amount, but preferably, the alkyl halocarbonate ester and the amine compound [13] are used each in an amount of about 1 to 1.5 mole, to 1 mole of the carboxylic acid compound [19].

Among the above other processes (d), in case of the process of reacting a carboxylic acid halide with the amine compound [13], the reaction is usually carried out in the presence of a basic compound in an appropriate solvent. The basic compound is any conventional compounds, and includes, for example, in addition to the basic compounds used for the above Schötten-Baumann reaction, sodium hydroxide, potassium hydroxide, sodium hydride, potassium hydride, and the like. The solvent includes, for example, in addition to the solvents used in the mixed acid anhydride process, alcohols (e.g. methanol, ethanol, propanol, butanol, 3-methoxy-1-butanol, ethylcellosolve, methylcellosolve, etc.), pyridine, acetone, water, and the like. The amount of the amine compound [13] and the carboxylic acid halide is not critical, but the amine compound [13] is usually used at least in equimolar amount, preferably in an amount of about 1 to 5 moles, to 1 mole of the carboxylic acid halide. The reaction is usually carried out at a temperature from about −20° C. to about 180° C., preferably at a temperature from 0° C. to about 150° C., for about 5 minutes to about 30 hours.

The amido bond producing reaction in the above Reaction Scheme-5 may also be carried out by reacting the carboxylic acid compound [19] and the amine compound [13] in the presence of a condensing agent such as phosphorus compounds (e.g. phenylphosphine-2,2'-dithiodipyridine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, etc.).

The reaction is usually carried out in the presence of the solvent and the basic compound as used in the above reaction of the carboxylic acid halide and the amine compound [13] at a temperature from −20° C. to about 150° C., preferably at a temperature from 0° C. to about 100° C., for about 5 minutes to about 30 hours. The condensing agent and the amine compound [13] are used at least in equimolar amount, preferably in an amount of about 1 to 5 moles, to 1 mole of the carboxylic acid compound [19].

The reaction of converting the compound [20] into the compound [2a] is carried out by reacting the compound [20] with metal magnesium in an appropriate solvent. The solvent includes, for example, alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), aromatic hydrocarbons (e.g. benzene, toluene, xylene, etc.), aliphatic hydrocarbons (e.g. hexane, cyclohexane, heptane, etc.), aprotic polar solvents (e.g. dimethylformamide, dimethyl sulfoxide, hexamethylphosphoric triamide, etc.), or a mixture of these solvents. Metal magnesium is usually used in excess amount, preferably in an amount of 5 to 20 moles, to 1 mole of the compound [20]. The reaction is usually carried out at a temperature from room temperature to about 120° C., preferably at a temperature from room temperature to about 100° C., for one hour to about 15 hours.

The compound [2a] may also be prepared by treating the compound [20] in an appropriate solvent in the presence of an acid such as sulfuric acid, etc. The solvent includes, for example, in addition to aromatic hydrocarbons (e.g. benzene, toluene, xylene, etc.), the above mentioned alcohols, ethers, aliphatic hydrocarbons, aprotic polar solvents, or a mixture of these solvents. The acid is usually used in an excess amount, to the compound [20]. The reaction is usually carried out at a temperature from room temperature to 150° C., preferably at a temperature from 50° C. to about 120° C., for one hour to about 10 hours. There is added anisole, etc. to the reaction system in order to promote the reaction.

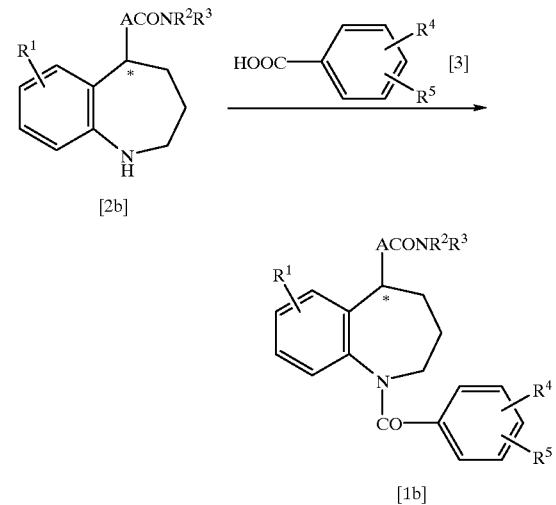

Reaction Scheme-6 wherein $R^1$, $R^2$, $R^3$, $R^4$, $R^5$ and A are the same as defined above.

The reaction of the compound [2b] and the compound [3] is carried out under the same conditions as those in the reaction of the compound [19] and the compound [13] in the above Reaction Scheme-5. The compound [3] is usually used at least in an equimolar amount, preferably in an amount of 1 to 5 moles, to 1 mole of the compound [2b].

The solvent includes, for example, aliphatic hydrocarbons (e.g. cyclohexane, n-hexane, etc.), aromatic hydrocarbons (e.g. benzene, toluene, xylene, etc.), ethers (e.g. diethyl ether, diisopropyl ether, dioxane, tetra-hydrofuran, etc.), halogenated hydrocarbons (e.g. dichloromethane,

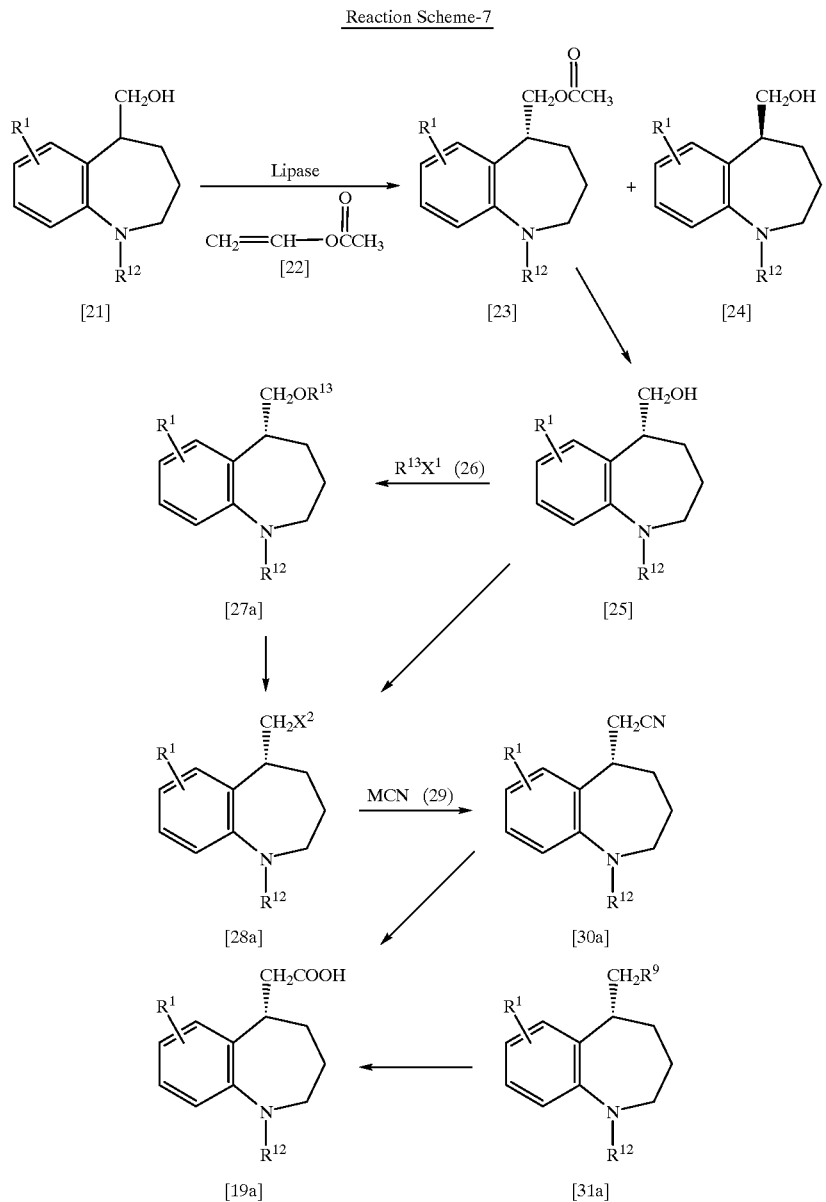

Reaction Scheme-7 wherein $R^1$, $X^1$, $R^9$ and $R^{12}$ are the same as defined above, $X^2$ is a halogen atom, $R^{13}$ is a lower alkylsulfonyl group, and M is an alkali metal atom such as sodium, potassium, etc.

The lower alkylsulfonyl group includes a straight chain or branched chain alkylsulfonyl group having 1 to 6 carbon atoms, for example, methylsulfonyl, ethylsulfonyl, propylsulfonyl, isopropylsulfonyl, butylsulfonyl, tert-butylsulfonyl, pentylsulfonyl, hexylsulfonyl, and the like.

The reaction of converting the compound [21] into the compound [23] and the compound [24] is carried out by reacting the compound [21] with vinyl acetate [22] in the presence of a lipase in an appropriate solvent, or without a solvent.

chloroform, carbon tetrachloride, etc.), esters (e.g. methyl acetate, ethyl acetate, etc.), acetonitrile, or a mixture of these solvents.

The lipase may be any lipase produced by various organisms such as animals, yeasts, fungi, bacteria, etc., or any commercially available ones. The commercially available lipases are, for example, Lipase QL (manufactured by Meito Sangyo, Co., Ltd., produced by *Alcaligenes, sp.*), Lipase PL (manufactured by Meito Sangyo, Co., Ltd., produced by a species of the genus Alcaligenes), Lipase QLG (manufactured by Meito Sangyo, Co., Ltd., produced by a species of the genus Alcaligenes), Lipase OF (manufactured by Meito Sangyo, Co., Ltd., produced by *Candida cylindrasea*), Lipozyme IM (manufactured by Novo Nordisk A/A, produced by *Mucor miehei*), Novozymes 435, SO523, SP524, SP525, SP526 (manufactured by Novo Nordisk A/A, produced by *Aspergillus oryzae*), Subtilisin A (manufactured by Novo Nordisk A/A, produced by *Basillus licheniformis*), Toyozyme LIP (manufactured by Toyo Boseki Kabushiki Kaisha), PPL (manufactured by Sigma, Israeli Chemicals Ltd., isolated from porcine pancreas), CCL (manufactured by Sigma, Israeli Chemicals Ltd., produced by a species of the genus Candida), Nacalai lipase (manufactured by Nacalai Teaque Inc., produced by *Pseudomonas fluorescens*), etc. Among these commercially available lipases, Lipase QL is especially preferable. The amount of lipase is not critical, but it is usually used in a catalytic amount, preferably in an amount of 0.001 to 0.1 time by weight, to the weight of the compound [21].

In the reaction, the amount of the viny acetate [22] is not critical, but it is usually used in an amount of 1 to 10 moles, preferably in an amount of 1 to 5 moles, to 1 mole of the compound [21]. The reaction is usually carried out at a temperature from −10° C. to about 60° C., preferably at a temperature from −10° C. to room temperature, for 30 minutes to about 5 hours.

In the reaction, the compound [24] is also obtained, but the compound [23] and the compound [24] are easily separated by a conventional separation method, such as column chromatography, preparative thin layer chromatography, etc.

The reaction of converting the compound [23] into the compound [25] is carried out in the presence of an acid or a basic compound in an appropriate solvent or without a solvent. The solvent includes, for example, water, alcohols (e.g. methanol, ethanol, isopropanol, etc.), ketones (e.g. acetone, methyl ethyl ketone, etc.), ethers (e.g. diethyl ether, dioxane, tetrahydrofuran, ethylene glycol dimethyl ether, etc.), fatty acids (e.g. formic acid, acetic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature from room temperature to about 200° C., preferably at a temperature from room temperature to about 150° C., for 0.05 hour to about 25 hours.

The reaction of converting the compound [25] into the compound [28a] is carried out in the presence of a halogenating agent in an appropriate inert solvent, or without a solvent, at a temperature from room temperature to about 100° C., preferably at a temperature from 50° C. to about 80° C., for 30 minutes to about 6 hours. The halogenating agent includes, for example, thionyl chloride, phosphorus oxychloride, phosphorus oxybromide, phosphorus pentachloride, phosphorus pentabromide, etc., and the solvent includes, for example, halogenated hydrocarbons (e.g. chloroform, methylene chloride, carbon tetrachloride, etc.), ethers (e.g. dioxane, tetrahydrofuran, diethyl ether, etc.), and the like. The halogenating agent is usually used in an excess amount to the amount of the compound [25] when the reaction is carried out without a solvent. When the reaction is carried out in a solvent, the halogenating agent is used at least in an equimolar amount, preferably in an amount of 2 to 4 moles, to 1 mole of the compound [25].

The compound [28a] may also be prepared by reacting the compound [25] with a carbon tetrahalide such as carbon tetrachloride, carbon tetrabromide, in the presence of triphenylphosphine in the above mentioned solvent. The amounts of triphenylphosphine and a carbon tetrahalide are at least in an equimolar amount, preferably in an amount of 1 to 3 moles, to 1 mole of the compound [25], respectively. The reaction is usually carried out at a temperature from 0° C. to 100° C., preferably at a temperature from 0° C. to about 70° C., for 10 minutes to about 5 hours.

The reaction of the compound [28a] and the compound [29] is usually carried out in an appropriate inert solvent. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, tert-butanol, etc.), acetic acid, ethyl acetate, acetone, acetonitrile, pyridine, dimethyl sulfoxide, dimethylformamide, hexamethylphosphoric triamide, or a mixture of these solvents. The amounts of the compound [28a] and the compound [29] are not critical, but the compound [29] is used at least in an equimolar amount, preferably in an amount of 1 to 5 moles, to 1 mole of the compound [28a]. The reaction is usually carried out at a temperature from 0° C. to about 150° C., preferably at a temperature from 0° C. to about 100° C., for 30 minutes to about 10 hours. There may be added a crown ester such as 18-crown-6, etc. into the reaction system.

The reaction of converting the compound [30a] into the compound [31a] is carried out in the presence of an acid in an appropriate solvent. The solvent includes, for example, water, alcohols (e.g. methanol, ethanol, isopropanol, ethylene glycol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The reaction is usually carried out at a temperature from room temperature to about 200° C., preferably at a temperature from room temperature to about 150° C., for 10 minutes to about 10 hours.

The reaction of converting the compound [30a] into the compound [19a] is carried out in the presence of a basic compound in an appropriate solvent. The solvent may be the same solvents as those used in the above reaction of the compound [30a] and the compound [31a]. The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at a temperature from room temperature to 250° C., preferably at a temperature from room temperature to about 200° C., for one hour to about 10 hours.

The reaction of converting the compound [31a] into the compound [19a] is carried out under the same conditions as those in the reaction of converting the compound [17] into the compound [18] in the above Reaction Scheme-5.

The reaction of the compound [25] and the compound [26] is usually carried out in the presence or absence of a basic compound, in an appropriate inert solvent. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, tert-butanol, etc.), acetic acid, ethyl acetate, acetone, acetonitrile, pyridine, dimethyl sulfoxide, dimethylformamide, hexamethylphosphoric triamide, or a mixture of these solvents. The basic compound includes, for example, metal carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, alkali metal alcoholates (e.g. sodium methylate, sodium ethylate, etc.), organic bases (e.g. pyridine, N-ethyldiisopropylamine, dimethylaminopyridine, triethylamine, 1,5-diazabicyclo[4.3.0]nonene-5 (DBU), 1,8-diazabicyclo[5.4.0]undecene-7 (DBU), 1,4-diazabicyclo[2.2.2]octane (DABCO), etc.), and the like. The amounts of the compound [25] and the compound [26] are not critical, but the compound [26] is usually used at least in an equimolar amount, preferably in an amount of 1 to 5 moles, to 1 mole of the compound [25]. The reaction is usually carried out at a temperature from 0° C. to about 150° C., preferably at a temperature from 0° C. to about 100° C., for 30 minutes to about 30 hours. There may be added an alkali metal halide such as sodium iodide, potassium iodide, etc., into the reaction system.

The reaction of converting the compound [27a] into the compound [28a] is carried out by reacting the compound [27a] with a compound of the formula: $MX^2$ (M and $X^2$ are the same as defined above), in an appropriate solvent. The solvent may be the same solvent as those used in the reaction of the compound [25] and the compound [26]. The compound of the formula: $MX^2$ is used at least in an equimolar amount, preferably in an amount of 1 to 5 moles, to 1 mole of the compound [27a]. The reaction is usually carried out at a temperature from room temperature to 150° C., preferably at a temperature from room temperature to about 100° C., for one hour to about 5 hours.

Reaction Scheme-8

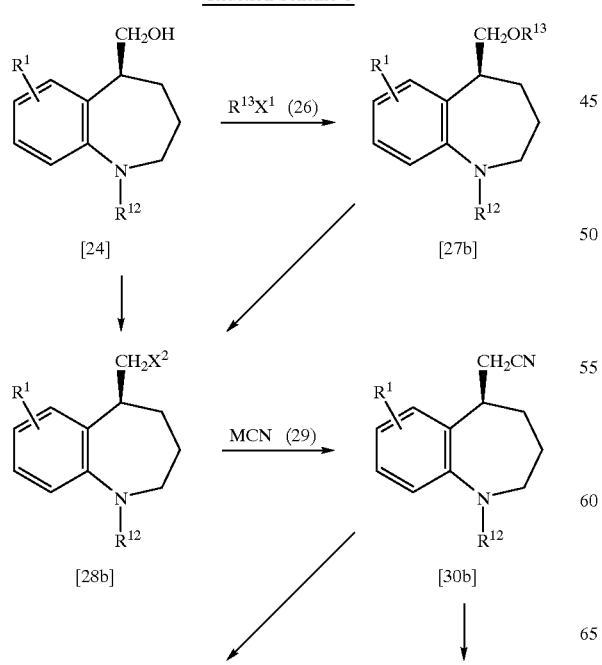

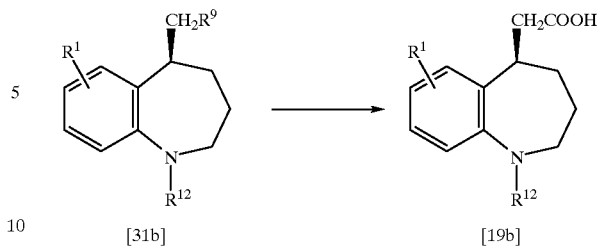

wherein $R^1$, $R^{12}$, $R^{13}$, $X^1$ and $R^9$ are the same as defined above.

The reaction of the compound [24] and the compound [26] is carried out under the same conditions as those in the reaction of the compound [25] and the compound [26] in the above Reaction Scheme-7.

The reaction of converting the compound [27b] into the compound [28b] is carried out under the same conditions as those in the reaction of converting the compound [27a] into the compound [28a] in the above Reaction Scheme-7.

The reaction of converting the compound [24] into the compound [28b] is carried out under the same conditions as those in the reaction of converting the compound [25] into the compound [28a] in the above Reaction Scheme-7.

The reaction of the compound [28b] and the compound [29] is carried out under the same conditions as those in the reaction of the compound [28a] and the compound [29] in the above Reaction Scheme-7.

The reaction of converting the compound [30b] into the compound [31b] is carried out under the same conditions as those in the reaction of converting the compound [30a] into the compound [31a] in the above Reaction Scheme-7.

The reaction of converting the compound 13b] into the compound [19b] is carried out under the same conditions as those in the reaction of converting the compound [31a] into the compound [19a] in the above Reaction Scheme-7.

The reaction of converting the compound [30b] into the compound [19b] is carried out under the same conditions as those in the reaction of converting the compound [30a] into the compound [19a] in the above Reaction Scheme-7.

The starting compound [21] used in the above Reaction Scheme-7 may be prepared by the following process.

Reaction Scheme-9

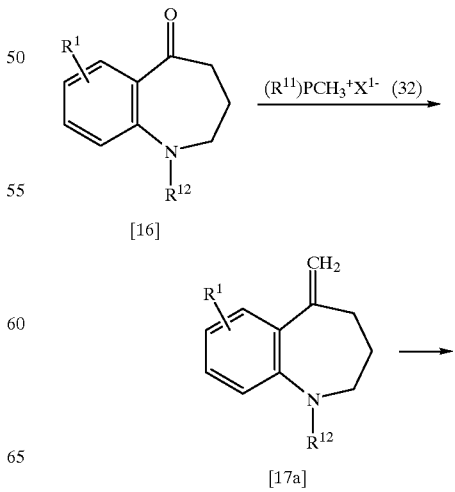

-continued

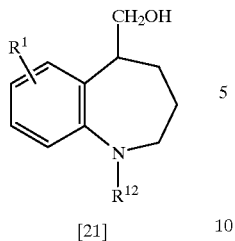

[21]

wherein $R^1$, $R^{11}$, $R^{12}$ and $X^1$ are the same as defined above.

The reaction of the compound [16] and the compound [32] is carried out under the same conditions as those in the reaction of the compound [16] and the compound [9] in the above Reaction Scheme-5.

The reaction of converting the compound [17a] into the compound [21] is carried out by hydroboration reaction, and then followed by oxidization of the product.

The hydroboration reaction is carried out in the presence of a hydroborating agent in a solvent such as ethers (e.g. diethyl ether, tetrahydrofuran, dioxane, etc.), at a temperature from 0° C. to 50° C., preferably at a temperature from 0° C. to room temperature, for one hour to about 10 hours. The hydroborating agent may be boron hydride compounds as listed below.

Boron hydride compounds $BH_3$.tetrahydrofuran, $BH_3$.$S(CH_3)_2$, $BH_2Cl$, $(CH_3)_2CHC(CH_3)_2BH_2$, $(CH_3)_2CHCH(CH_3)BH$,

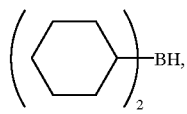

-continued

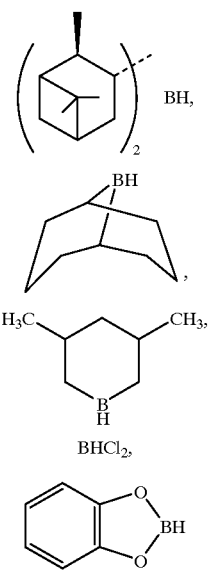

$BHCl_2$, and the like.

The subsequent oxidization reaction is carried out in the presence of an oxidizing agent in water. The oxidizing agent includes, for example, alkaline hydrogen peroxide such as hydrogen peroxide-sodium hydroxide, etc., oxidation by air, etc. The reaction is usually carried out at a temperature from room temperature to 150° C., preferably at a temperature from room temperature to about 100° C., for 0.5 hour to about 7 hours.

The hydroborating agent and the oxidizing agent are usually used at least in an equimolar amount, preferably in an amount of 1 to 2 moles, to 1 mole of the compound [17a].

Reaction Scheme-10

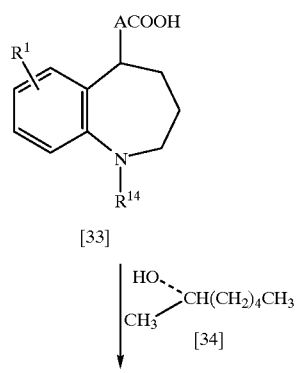

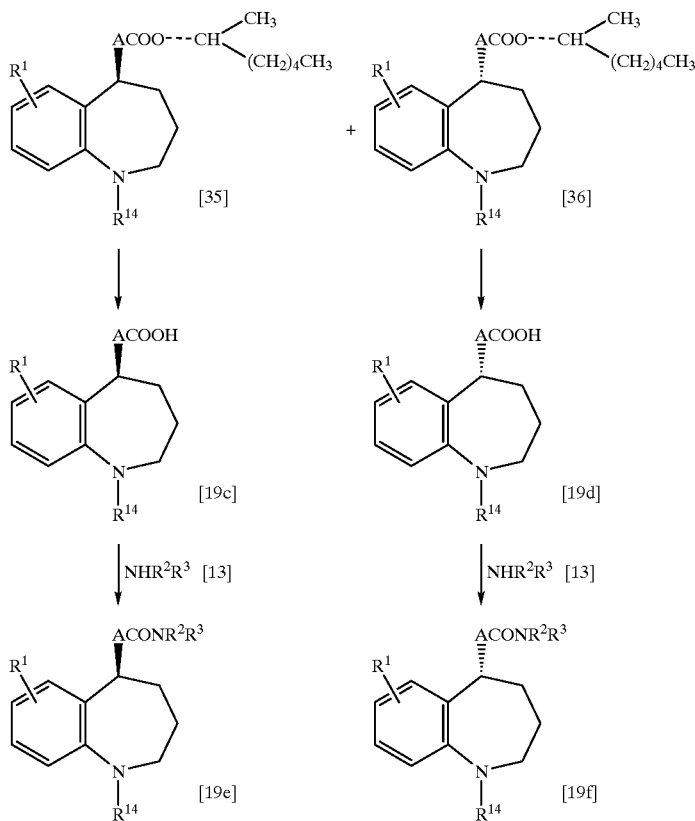

wherein $R^1$, $R^2$, $R^3$, $R^{14}$ and A are the same as defined above.

The reaction of the compound [33] and the compound [34] is carried out in the presence of a basic compound and an activation agent in an appropriate solvent. The solvent and the basic compound are the same ones as those used in the reaction of the carboxylic acid halide with the amine compound [13] in the above Reaction Scheme-5, respectively. The activating agent includes, for example, dicyclohexylcarbodiimide, carbonyldiimidazole, a water soluble carbodiimide, etc. The amounts of the compound [34] and the activating agent are at least in an equimolar amount, preferably in an amount of 1 to 2 moles, to 1 mole of the compound [33], respectively. The reaction is usually carried out at a temperature from 0° C. to 150° C., preferably at a temperature from 0° C. to about 100° C., for 1 hour to 10 hours. The optically active compounds [35] and [36] thus obtained are easily separated by a conventional separation method, for example, by recrystallization to give the compounds [35] and [36] separately with optically high purity.

The reaction of converting the compound [35] into the compound [19c], and the reaction of converting the compound [36] into the compound [19d] are carried out under the same conditions as those in the reaction of converting the compound [17] into the compound [18] in the above Reaction Scheme-5.

The reaction of the compound [19c] and the compound [13], and the reaction of the compound [19d] and the compound [13] are carried out under the same conditions as those in the reaction of the compound [19] and the compound [13] in the above Reaction Scheme-5.

The starting compound [33] used in the above Reaction Scheme-10 is prepared by the following process.

Reaction Scheme-11

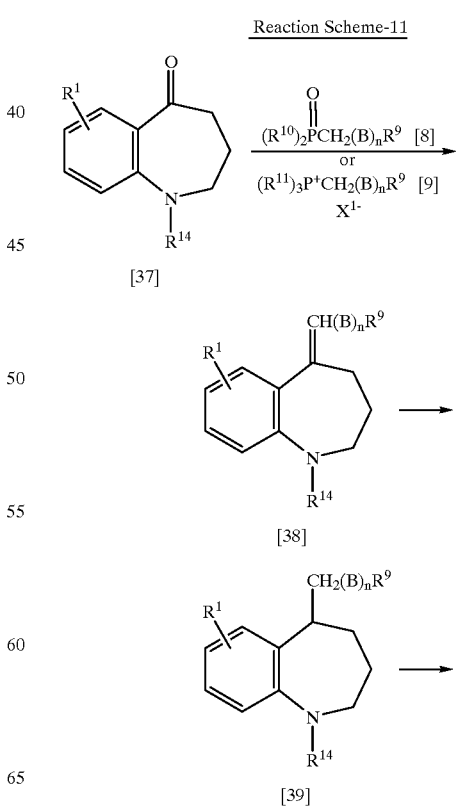

-continued

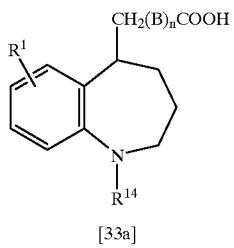

[33a]

wherein $R^1$, $R^9$, $R^{10}$, $R^{11}$, $R^{14}$, B, n and $X^1$ are the same as defined above.

The reaction of the compound [37] and the compound [8] or the compound [9] is carried out in the presence of a basic compound in an appropriate solvent. The basic compound includes, for example, inorganic bases such as sodium, potassium, sodium hydride, sodium amide, sodium hydroxide, potassium hydroxide, sodium carbonate, potassium carbonate, sodium hydrogen carbonate, etc., organic bases such as metal alcoholates (e.g. sodium methylate, sodium ethylate, potassium t-butoxide, etc.), alkyl lithium, aryl lithium and lithium amide (e.g. methyl lithium, n-butyl lithium, phenyl lithium, lithium diisopropylamide, etc.), pyridine, piperidine, quinoline, triethylamine, N,N-dimethylaniline, and the like. The solvent may be any conventional ones which do not affect the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethyl sulfoxide, hexamethylphosphoric triamide, etc.), alcohols (e.g. methanol, ethanol, isopropanol, etc.), and the like. The reaction is usually carried out at a temperature from −80° C. to 150° C., preferably at a temperature from −80° C. to about 120° C., for 0.5 hour to about 15 hours. The compound [8] or the compound [9] is usually used at least in equimolar amount, preferably in an amount of 1 to 5 moles, to 1 mole of the compound [37].

The reaction of converting the compound [38] into the compound [39] is carried out by reduction reaction. The reduction reaction is carried out by various methods, for example, by catalytic hydrogenation in the presence of a catalyst in an appropriate solvent. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium-black, palladium-carbon, platinum, platinum oxide, copper chromite, Ranney nickel, and the like. The catalyst is usually used in an amount of 0.02 to 1 time, to the amount of the starting compound. The reaction is usually carried out at a temperature from −20° C. to about 100° C., preferably at a temperature from 0° C. to about 70° C., under a pressure of 1 atm to 10 atms of hydrogen gas, for 0.5 hour to about 20 hours.

The reduction reaction may be carried out under the above reduction conditions, but preferably carried out by using a hydrogenation agent. The hydrogenation agent includes, for example, lithium aluminum hydride, sodium borohydride, sodium cyanoborohydride, diborane, and the like. The hydrogenation agent is used at least in an amount of 0.1 mole, preferably in an amount of 0.1 mole to 10 moles, to 1 mole of the compound [38]. The reduction reaction is usually carried out in an appropriate solvent such as water, lower alcohols (e.g. methanol, ethanol, isopropanol, etc.), ethers (e.g. tetrahydrofuran, diethyl ether, diglyme, etc.), dimethylformamide, or a mixture thereof, at a temperature from −60° C. to 50° C., preferably at a temperature from −30° C. to room temperature, for about 10 minutes to about 5 hours. In case that lithium aluminum hydride or diborane is used as a reducing agent, it is preferable to use an anhydrous solvent such as diethyl ether, tetrahydrofuran, diglyme, and the like.

When a hydrogenation reducing agent is used, an alkali metal halide such as nickel chloride, etc. may be added into the reaction system in order to promote the reaction.

The compound [38] may also be converted into the compound [39] by reducing the compound [38] with using metal magnesium-methanol. The reaction is usually carried out at a temperature from 0° C. to 50° C., preferably at a temperature from 0° C. to room temperature, for about one hour to about 10 hours. Metal magnesium is usually used in an amount of 1 to 10 moles, preferably in an amount of 1 to 7 moles, to 1 mole of the compound [38].

The reaction of converting the compound [39] into the compound [33a] is carried out in the presence of an acid or a basic compound, in an appropriate solvent or without a solvent. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The basic compound includes, for example, metal carbonates (e.g. sodium carbonate, potassium carbonate, etc.), metal hydroxides (e.g. sodium hydroxide, potassium hydroxide, calcium hydroxide, lithium hydroxide, etc.), and the like. The reaction is usually carried out at a temperature from room temperature to about 200° C., preferably at a temperature from room temperature to about 150° C., for 10 minutes to about 25 hours.

Reaction Scheme-12

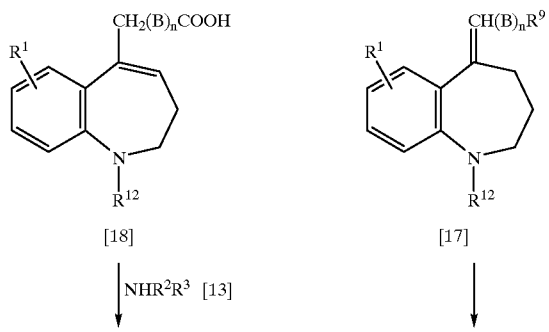

[18]     [17]

NHR²R³ [13]

-continued

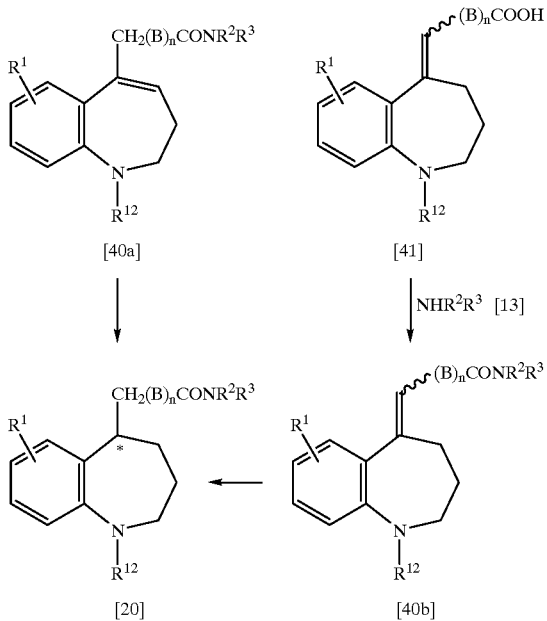

wherein $R^1$, $R^2$, $R^3$, $R^9$, $R^{12}$, B and n are the same as defined above.

The reaction of the compound [18] and the compound [13], and the reaction of the compound [41] and the compound [13] are carried out under the same conditions as those in the reaction of the compound [19] and the compound [13] in the above Reaction Scheme-5.

The reaction of converting the compound [17] into the compound [41] is carried out under the same conditions as those in the reaction of converting the compound [39] into the compound [33a] in the above Reaction Scheme-11.

The reaction of converting the compound [40a] or the compound [40b] into the compound [20] is carried out under the same conditions as those in the reaction of converting the compound [18] into the compound [19] in the above Reaction Scheme-5.

The starting compound [7] used in the Reaction Scheme-3 may be prepared by reacting a compound of the formula:

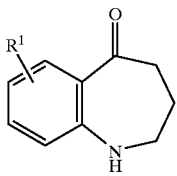

wherein $R^1$ is the same as defined above, with a compound of the formula:

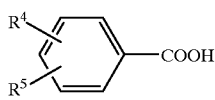

wherein $R^4$ and $R^5$ are the same as defined above, under the same conditions as those in the reaction of the compound [2] and the compound [3] in the above Reaction Scheme-1.

Among the desired compounds [1] of the present invention, the compounds having an acidic group can easily be converted into salts by treating with a pharmaceutically acceptable basic compound. The basic compound includes, for example, metal hydroxides (e.g. sodium hydroxide, potassium hydroxide, lithium hydroxide, calcium. hydroxide, etc.), alkali metal carbonates or hydrogen carbonates (e.g. sodium carbonate, sodium hydrogen carbonate, etc.) and alkali metal alcoholates (e.g. sodium methylate, potassium ethylate, etc.). Besides, among the desired compounds [1] of the present invention, the compounds having a basic group can easily be converted into acid addition salts thereof by treating with a pharmaceutically acceptable acid. The acid includes, for example, inorganic acids (e.g. sulfuric acid, nitric acid, hydrochloric acid, hydrobromic acid, etc.), and organic acids (e.g. acetic acid, p-toluenesulfonic acid, ethanesulfonic acid, oxalic acid, maleic acid, fumaric acid, citric acid, succinic acid, benzoic acid, etc.). These salts show as well excellent pharmacological activities as the desired compounds [1].

In addition, the compounds [1] of the present invention include stereoisomers and optical isomers, and these isomers also show excellent pharmacological activities as well, and can be used as an active ingredient of the pharmaceutical compositions of the present invention.

The compounds of the present invention obtained in the above processes can easily be isolated and purified by conventional isolation methods from the reaction system. The isolation methods are, for example, distillation method, recrystallization method, column chromatography, ion exchange chromatography, gel chromatography, affinity chromatography, preparative thin layer chromatography, extraction with a solvent, and the like.

The desired compounds [1] of the present invention and salts thereof are useful as a vasopressin antagonist, an oxytocin antagonist, and a vasopressin agonist, and are used in the form of a conventional pharmaceutical preparation. The preparation is prepared by using powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of the present invention and the above carriers into hard gelatin capsules or soft capsules in usual manner. In the preparation of injections, the solutions, emulsions and suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agent, preservatives, perfumes, flavors, sweeting agents, and other medicaments, if required.

The amount of the desired compound of the present invention to be incorporated into the pharmaceutical composition is not specified but may be selected from a broad range, but usually, it is preferably in the range of 1 to 70% by weight, more preferably in the range of 5 to about 50% by weight.

The pharmaceutical composition containing as an active ingredient the compounds [1] of the present invention or a salt thereof may be administered in any method, and the suitable method for administration may be determined in accordance with various forms of preparations, ages, sexes and other conditions of the patients, the degree of severity of diseases, and the like. For example, tablets, pills, solutions, suspensions, emulsions, granules and capsules are administered orally. The injections are intravenously administered alone or together with a conventional auxiliary liquid (e.g. glucose, amino acid, etc.), and further are optionally administered alone in intramuscular, intracutaneous, subcutaneous, or intraperitoneal route, if required. Suppositories are administered in intrarectal route.

The dosage of the pharmaceutical composition of the present invention may be selected in accordance with the usage, ages, sexes and other conditions of the patients, the degree of severity of the diseases, and the like, but it is usually in the range of about 0.6 to 50 mg of the active compound of the present invention per 1 kg of body weight of the patient per day. The active compound is preferably contained in an amount of about 10 mg to about 1000 mg per dosage unit.

BEST MODE FOR CARRYING OUT THE INVENTION

EXAMPLES

The present invention is illustrated in more detail by the following Preparations of pharmaceutical composition, Reference Examples of processes for preparing the starting compounds to be used for preparing the desired compounds of the present invention, and Examples of processes for preparing the desired compounds, and Experiment of the activities of the desired compounds of the present invention.

Preparation 1

Film coated tablets are prepared from the following compounds.

| Components | Amount |
| --- | --- |
| 5-Isopropylaminocarbonylmethyl-1-(2-chloro-4-propylaminobenzoyl)-2,3,4,5-tetrahydro-1H-benzazepine | 150 g |
| Avicel (trade mark of microcrystalline cellulose manufactured by Asahi Chemical Industry, Co., Ltd.) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded, and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 7-Chloro-5-[(4-methyl-1-piperazinyl)carbonylmethyl]-1-(2-chloro-4-isopropylaminobenzoyl)-2,3,4,5-tetrahydro-1H-benzazepine | 150 g |
| Citric acid | 1.0 g |

| Components | Amount |
| --- | --- |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed.

The mixture is screened with No. 60 screen and is granulated with an alcohol solution containing polyvinylpyrrolidone, Carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
| --- | --- |
| 7-Chloro-5-isopropylaminocarbonylmethyl-1-(3-methoxy-4-isobutylaminobenzoyl)-2,3,4,5-tetrahydro-1H-benzazepine | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved with stirring in distilled water of half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Preparation 4

Film coated tablets are prepared from the following compounds.

| Components | Amount |
|---|---|
| (S)-5-Isopropylaminocarbonylmethyl-1-(2-chloro-4-propylaminobenzoyl)-2,3,4,5-tetrahydro-1H-benzazepine | 1 g |
| Avicel (trade mark of microcrystalline cellulose manufactured by Asahi Chemical Industry, Co., Ltd.) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded, and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 5

Tablets are prepared from the following components.

| Components | Amount |
|---|---|
| 7-Chloro-(R)-5-[(4-methyl-1-piperazinyl)carbonylmethyl]-1-(2-chloro-4-isopropylaminobenzoyl)-2,3,4,5-tetrahydro-1H-benzazepine | 1.0 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed.

The mixture is screened with No. 60 screen and is granulated with an alcohol solution containing polyvinylpyrrolidone, Carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 6

An injection preparation is prepared from the following components.

| Components | Amount |
|---|---|
| 7-Chloro-(S)-5-isopropylaminocarbonylmethyl-1-(3-methoxy-4-isobutylaminobenzoyl)-2,3,4,5-tetrahydro-1H-benzazepine | 0.1 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved with stirring in distilled water of half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Reference Example 1

To a suspension of 60% NaH (33.8 g) in tetrahydrofuran (2 liters) is added dropwise triethylphosphonoacetate (189 ml) under ice-cooling, and the mixture is stirred at room temperature for 1.5 hour. To the mixture is added 1-(p-toluenesulfonyl)-5-oxo-2,3,4,5-tetrahydro-1H-benzazepine (150 g) in portions at room temperature, and the mixture is stirred at 50° C. for 8 hours. To the reaction solution is added water, and the mixture is extracted three time with ethyl acetate. The organic layer is washed with water, dried over anhydrous magnesium sulfate, and concentrated under reduced pressure. The resulting crystals are collected by filtration, washed with n-hexane, and dried to give 1-(p-toluenesulfonyl)-5-ethoxycarbonylmethylidene-2,3,4,5-tetrahydro-1H-benzazepine (170.4 g).

White powder $^1$H-NMR (CDCl$_3$, 200 MHz) δ ppm: 1.09, 1.31 (3H, each t, each J=7.1 Hz), 1.44–1.90 (2H, m), 2.15–2.50 (1H, m), 2.36, 2.37 (3H, each s), 2.57–2.89 (1H, m), 3.65–4.03 (2H, m), 3.97, 4.14 (2H, each q, each J=7.1 Hz), 5.29, 5.62 (1H, each s), 6.98–7.76 (8H, m)

Reference Example 2

A mixture of 5-ethoxycarbonylmethylidene-1-(p-toluenesulfonyl)-2,3,4,5-tetrahydro-1H-benzazepine (18.6 g), methanol (130 ml) and a 4N sodium hydroxide solution in methanol (9.7 ml) is refluxed for three hours. To the mixture is added a 4N sodium hydroxide solution in methanol (12 ml), and the mixture is refluxed for 4.5 hours. Further, to the mixture is added a 5N aqueous sodium hydroxide solution (9.7 ml), and the mixture is refluxed for one hour and concentrated. To residue are added water and ethyl acetate, and the mixture is acidified with conc. hydrochloric acid. The mixture is extracted with ethyl acetate. The organic layer is washed with water, and dried over magne sium sulfate, and concentrated. The residue is crystallized from diethyl ether—n-hexane, and recrystallized from methanol—water to give 5-carboxymethyl-2,3-dihydro-1-(p-toluenesulfonyl)-1H-benzazepine (17.1 g).

M.p. 114–116° C.

Colorless needles

Reference Example 3

To a suspension of 1-(p-toluenesulfonyl)-5-ethoxycarbonylmethylidine-2,3,4,5-tetrahydro-1H-benzazepine (229 g) in methanol (3 liters) is added with stirring magnesium (117 g) in five portions at room temperature. That is, hydrogen gas is generated during the reaction, and when the generation of hydrogen gas is stopped, then another portion of magnesium is added. When hydrogen gas generates vigorously, the mixture is cooled over an ice bath. After the magnesium thus added is duly dissolved, the mixture is further stirred at room temperature for 12 hours. The reaction solution is cooled with ice, and thereto is added dropwise conc. sulfuric acid (270 ml) with stirring by a mechanical stirrer, and the mixture is stirred for 30 minutes. The precipitated magnesium sulfate is removed by filtration, and the filtrate is concentrated under reduced pressure to remove the methanol. The pH value of the mixture is adjusted to about pH 8 with a saturated aqueous sodium hydrogen carbonate, and the mixture is extracted with dichloromethane. The dichloromethane layer is washed with water, dried over magnesium sulfate, and concentrated under reduced pressure to remove the dichloromethane. The residue is purified by silica gel column chromatography (solvent; ethyl acetate:n-hexane=1:10) to give 5-methoxycarbonylmethyl-2,3,4,5-tetrahydro-1H-benzazepine (100 g).

Colorless oil $^1$H-NMR (CDCl$_3$, 200 MHz) δ ppm: 1.53–2.12 (4H, m), 2.64–2.99 (3H, m), 3.13–3.35 (1H, m), 3.36–3.79 [5H, m (3.58, 3H, s)], 6.69 (1H, dd, J=1.3 Hz, J=8.0 Hz), 6.82 (1 H, td, J=1.3 Hz, J=7.4 Hz), 7.01 (1H, dd, J=1.6 Hz, J=7.4 Hz), 7.09 (1H, td, J=1.6 Hz, J=8.0 Hz)

Reference Example 4

To 2-chloro-4-pyrrolidinylbenzoic acid (112 g) are added thionyl chloride (150 ml) and 1-methyl-2-pyrrolidone (1 ml), and the mixture is stirred at room temperature for 4 hours. The mixture is concentrated under reduced pressure to remove the thionyl chloride, and the mixture is subjected to azeotrophic distillation with toluene. The resulting residue is dissolved in dichloromethane (300 ml), and the mixture is added dropwise into a solution of 5-methoxycarbonylmethyl-2,3,4,5-tetrahydro-1H-benzazepine (110 g) and pyridine (70 ml) in dichloromethane (700 ml) under ice-cooling. The mixture is stirred for two hours, and acidified with hydrochloric acid. The precipitated crystals are removed by filtration, and the pH value of the filtrate is adjusted to about pH 8, and extracted with dichloromethane. The dichloromethane layer is dried over anhydrous magnesium sulfate, and concentrated under reduced pressure to remove the dichlomethane. The resulting crystals are collected by filtration, an dissolved in hot methanol. The mixture is treated with activated carbon, and the mixture is filtered through celite layer to remove the activated carbon. The filtrate is cooled, and the precipitated crystals are collected by filtration, washed with diethyl ether, recrystallized from methanol, and dried to give 5-methoxycarbonylmethyl-1-[4-(1-pyrrolidinyl)-2-chlorobenzoyl]-2,3,4,5-tetrahydro-1H-benzazepine (183 g).

M.p. 157.5–158° C.

Colorless prisms

Reference Example 5

5-Methoxycarbonylmethyl-1-[4-(1-pyrrolidinyl)-2-chlorobenzoyl]-2,3,4,5-tetrahydro-1H-benzazepine (183 g) is suspended in methanol (2 liters), and thereto is added a 5N sodium hydroxide (171 ml), and the mixture is stirred at 60° C. for four hours. To the mixture is added a 5N sodium hydroxide (60 ml), and the mixture is stirred at 70° C. for one hour. The mixture is acidified with hydrochloric acid, and concentrated under reduced pressure to remove the methanol. The crystals are collected by filtration, washed with water, and dried to give 5-carboxymethyl-1-[4-(1-pyrrolidinyl)-2-chlorobenzoyl]-2,3,4,5-tetrahydro-1H-benzazepine (142 g).

M.p. 227.5–228° C.

White powder

Reference Example 6

To 5-carboxymethyl-1-[4-(1-pyrrolidinyl)-2-chlorobenzoyl]-2,3,4,5-tetrahydro-1H-benzazepine (204 g) are added a water soluble carbodiimide (132.6 g), 4-dimethylaminopyridine (66.4 g) and (R)-(−)-2-heptanol (68.9 g) at room temperature, and the mixture is stirred at room temperature for 5–6 hours. The reaction mixture is acidified with hydrochloric acid, and extracted with ethyl acetate. The ethyl acetate layer is washed with water, dried over anhydrous magnesium sulfate, and concentrated under reduced pressure to remove ethyl acetate. The residue is purified by silica gel column chromatography (solvent; ethyl acetate:n-hexane=1:10→1:7→1:5→1:3) to give an oily distillate(30 g) containing mainly (5S)-5-((R)-2-heptyloxycarbonylmethyl)-1-[4-(1-pyrrolidinyl)-2-chlorobenzoyl]-2,3,4,5-tetrahydro-1H-benzazepine (hereinafter, referred to as Compound A), and crystals (33 g) of (5R)-5-((R)-2-heptyloxycarbonylmethyl)-1-[4-(1-pyrrolidinyl)-2-chlorobenzoyl]-2,3,4,5-tetrahydro-1H-benzazepine (hereinafter, referred to as Compound B).

Subsequently, the distillate containing mainly Compound A is treated as follows. Besides, the crystals of Compound B are recrystallized from diethyl ether-n-hexane to give Compound B (33 g).

The distillate (30 g) containing mainly Compound A is dissolved in methanol (120 ml) at 50–60° C., and thereto is added a 6N aqueous sodium hydroxide solution (25 ml), and the mixture is stirred at the same temperature for three hours. The mixture is weakly acidified with conc. hydrochloric acid (about pH 5–6), and concentrated under reduced pressure. To the resulting residue are added ethyl acetate and water, and the mixture is separated to remove the organic layer. The aqueous layer is basified with a 25% aqueous sodium hydroxide solution, and the mixture is extracted with methylene chloride. Since the above organic layer contains the same compound on the silica gel column chromatograph as the compound contained in the methylene chloride layer, these two layers are combined, dried over magnesium sulfate, and evaporated under reduced pressure to remove the solvent. The resulting solid is washed with ethyl acetate, collected by filtration, and dried to give a white powder (18.5 g).

The above white powder (18.5 g) is dissolved in DMF (180 ml), and thereto are added 4-dimethylaminopyridine (6 g), a water soluble carbodiimide (12 g) and (S)-(+)-2-heptanol (7.7 ml), and the mixture is stirred at room temperature overnight. The mixture is diluted with ethyl acetate (1 liter), washed with a 5% hydrochloric acid (150 ml) and water (1 liter), and separated. The washing procedure is repeated three times, and the organic layers are combined, and dried over magnesium sulfate. The resultant is evaporated under reduced pressure to remove the solvent to give an oily crude product (24 g), which is purified by silica gel column chromatography (solvent; ethyl acetate:n-hexane= 1:4), and recrystallized from ethyl acetate—n-hexane to give (5S)-5-((S)-2-heptyloxycarbonylmethyl)-1-[4-(1-pyrrolidinyl)-2-chlorobenzoyl]-2,3,4,5-tetrahydro-1H-benzazepine (hereafter, referred to as Compound A') (7.74 g) as colorless needles.

Compound A'

M.p. 106–107° C. (recrystallized from ethyl acetate—n-hexane)

Colorless needles $[\alpha]_D^{23}$: +217° (C=0.55, ethanol)

Optical purity: >99% e.e.

Compound B

M.p. 104–105° C. (recrystallized from diethyl ether—n-hexane)

Colorless prisms $[\alpha]_D^{22}$: −231.2° (C=0.5, ethanol)

$^1$H-NMR (CDCl$_3$, 200 MHz) δ ppm: 0.65–2.25 (23H, m), 2.48–3.97, 4.38– 4.68, 4.78–5.24 [total 9H, m (2.67, 1H, dd, J=7.4 Hz, J=6 Hz) (2.89, 1H, dd, J=8.1 Hz, J=16 Hz)], 5.93–6.19, 6.27–7.50 [total 7H, m (6.09, dd, J=2.4 Hz, J=8.0 Hz) (6.38, d, J=2.3 Hz)]

Optical purity: 99% e.e.

Conditions for HPLC analysis of optical purity:

Column: TSK-80Tm (manufactured by TOSO CO., LTD.)

Solvent: Acetonitrile:water:acetic acid=75:25:1

Detection: UV$_{254nm}$

Flow rate: 1.0 ml/min.

Retention time: 15 minutes ((R-R)-isomer), 16 minutes ((S-R)-isomer)

Reference Example 7

5-Hydroxymethyl-1-(p-toluenesulfonyl)-2,3,4,5-tetrahydro-1H-benzazepine (9.94 g) is dissolved in diisopropyl ether (150 ml), and thereto are added with stirring vinyl acetate (7.75 g) and Lipase QL (8%) (0.80 g) at −2° C. The mixture is stirred at −2° C. to 1° C. for 1.5 hour. The Lipase QL is removed by filtration on celite, and the filtrate is evaporated under reduced pressure, and the resulting residue is purified by silica gel column chromatography (solvent; n-hexane:ethyl acetate=3:1→1:1) to give (5S)-5-hydroxymethyl-1-(p-toluenesulfonyl)-2,3,4,5-tetrahydro-1H-benzazepine (hereinafter, referred to as Compound C) (4.54 g) and (5R)-5-acetyloxymethyl-1-(p-toluenesulfonyl)-2,3,4,5-tetrahydro-1H-benzazepine (hereinafter, referred to as Compound D) (5.63 g).

Compound C

Colorless oil $[\alpha]_D^{25}$: +9.1° (C=1, chloroform)

$^1$H-NMR (CDCl$_3$, 250 MHz) δ ppm: 1.00–2.25 (4H, br), 2.44 (3H, s), 2.50–3.50 (2H, br), 3.70–4.00 (2H, br), 4.00–4.35 (2H, br), 6.90–7.40 (6H, m), 7.60–7.80 (2H, m)

Optical purity: >99% e.e.

Conditions for HPLC analysis of optical purity:

Column: CHIRALCEL OJ (manufactured by DAICEL CHEMICAL INDUSTRIES, LTD.)

Solvent: n-Hexane:isopropyl alcohol:diethyl amine= 700:300:1

Detection: UV$_{254nm}$

Chart speed: 1 mm/min.

Retention time: 8.2 minutes (R-isomer), 6.9 minutes (S-isomer)

Compound D

M.p. 97–99° C. (recrystallized from ethyl acetate—n-hexane)

Colorless needles $[\alpha]_D^{25}$: −13.7° (C=1, chloroform)

Optical purity: 99.1% e.e.

Conditions for HPLC analysis of optical purity:

Column: CHIRALCEL OJ (manufactured by DAICEL CHEMICAL INDUSTRIES, LTD.)

Solvent: n-Hexane:isopropyl alcohol:diethyl amine= 700:300:1

Detection: UV$_{254nm}$

Chart speed: 1 mm/min.

Retention time: 17.0 minutes (R-isomer), 12.5 minutes (S-isomer)

Reference Example 8

To (5S)-5-hydroxymethyl-1-(p-toluenesulfonyl)-2,3,4,5-tetrahydro-1H-benzazepine (4.44 g) and dichloromethane (70 ml) are added with stirring pyridine (3.18 g) and methanesulfonyl chloride (3.87 g) under ice-cooling, and the mixture is stirred overnight at room temperature. To the reaction solution is added a 5% hydrochloric acid, and the mixture is extracted with dichloromethane. The extract is dried over sodium sulfate, and evaporated under reduced pressure to remove the solvent, and the resulting residue is purified by silica gel column chromatography (solvent; n-hexane:ethyl acetate=2:1→1:1) to give (5S)-5-methylsulfonyloxy-1-(p-toluenesulfonyl)-2,3,4,5-tetrahydro-1H-benzazepine (5.18 g).

Colorless amorphous $^1$H-NMR (CDCl$_3$, 250 MHz) δ ppm: 1.00–2.25 (4H, br), 2.46 (3H, s), 2.95 (3H, s), 2.90–3.50 (2H, br), 4.00–4.80 (3H, br), 6.90–7.40 (6H, m), 7.60–7.80 (2H, m)

Reference Example 9

A mixture of (5S)-5-methylsulfonyloxy-1-(p-toluenesulfonyl)-2,3,4,5-tetrahydro-1H-benzazepine (5.16 g), acetonitrile (45 ml), and sodium iodide (2.65 g) is refluxed for 30 minutes, and thereto is added sodium iodide (2.65 g). The mixture is refluxed for totally two hours, and thereto is added ice, and extracted with dichloromethane. The dichloromethane layer is washed with a 5% aqueous sodium thiosulfate pentahydrate solution, and dried over sodium sulfate. The resultant is evaporated under reduced pressure, and the residue is purified by silica gel column chromatography (solvent; n-hexane:ethyl acetate=3:1) to give (5S)-4-iodomethyl-1-(p-toluenesulfonyl)-2,3,4,5-tetrahydro- 1H-benzazepine (1.89 g).

Yellow oil $^1$H-NMR (CDCl$_3$, 250 MHz) δ ppm: 1.00–2.05 (4H, br), 2.45 (3H, s), 2.80–3.80 (3H, br), 3.80–4.50 (2H, br), 7.10–7.45 (6H, m), 7.50–7.90 (2H, m)

Reference Example 10

A mixture of (5S)-5-iodomethyl-1-(p-toluenesulfonyl)-2,3,4,5-tetrahydro-1H-benzazepine (1.41 g), potassium cyanide (0.42 g), a catalytic amount of 18-crown-6 and dimethylformamide (16 ml) is heated with stirring at 85° C. for one hour. To the mixture is added potassium cyanide (0.42 g), and the mixture is further stirred at 85° C. for totally 6 hours. To the reaction solution is added ice, and the mixture is extracted with ethyl acetate—toluene. The extract is dried over sodium sulfate, and concentrated under reduced pressure to remove the solvent. The residue is purified by silica gel column chromatography (solvent; n-hexane:ethyl acetate=4:1), and recrystallized from ethyl acetate—n-hexane to give (5R)-5-cyanomethyl-1-(p-toluenesulfonyl)-2,3,4,5-tetrahydro-1H-benzazepine (0.41 g).

M.p. 106° C.

Colorless needles

[α]$_D^{25}$: +16.0° (C=0.1, methanol)

Reference Example 11

A mixture of (5R)-5-cyanomethyl-1-(p-toluenesulfonyl)-2,3,4,5-tetrahydro-1H-benzazepine (0.51 g), water (27 ml) and a 20% hydrochloric acid in methanol (15 ml) is refluxed for 3.5 hours. The mixture is evaporated under reduced pressure to remove the solvent, and extracted with dichloromethane. The extract is dried over sodium sulfate, evaporated under reduced pressure to remove the solvent, and the residue is purified by silica gel column chromatography (solvent; n-hexane:ethyl acetate=4:1) to give (5R)-5-methoxycarbonylmethyl-1-(p-toluenesulfonyl)-2,3,4,5-tetrahydro-1H-benzazepine (0.30 g).

White powder $^1$H-NMR (DMSO-d$_6$, 250 MHz) δ ppm: 1.60–1.95 (4H, br), 2.43 (3H, s), 2.50–2.90 (2H, br), 2.90–3.55 (2H, br), 3.64 (3H, s), 3.80–4.40 (1H, br), 7.00–7.40 (6H, m)

Optical purity: 96.4% e.e.

Conditions for HPLC analysis of optical purity:

Column: CHIRALCEL OJ (manufactured by DAICEL CHEMICAL INDUSTRIES, LTD.)

Solvent: n-Hexane:ethanol:trifluoroacetic acid=800:200:3

Detection: UV$_{254nm}$

Chart speed: 1 mm/min.

Retention time: 14.6 minutes (R-isomer), 24.4 minutes (S-isomer)

Reference Example 12

A mixture of (5S)-5-hydroxymethyl-1-(p-toluenesulfonyl)-2,3,4,5-tetrahydro-1H-benzazepine (1.33 g), triphenylphosphine (2.10 g), carbon tetrabromide (2.65 g) and dichloromethane (50 ml) is stirred at room temperature for 30 minutes. The reaction solution is poured into a saturated aqueous sodium hydrogen carbonate solution, and the mixture is extracted with dichloromethane. The extract is dried over sodium sulfate, and concentrated under reduced pressure to remove the solvent, and the resulting residue is purified by silica gel column chromatography (solvent; dichloromethane:n-hexane=4:1), and recrystallized from diethyl ether—n-hexane to give (5S)-5-bromomethyl-1-(p-toluenesulfonyl)-2,3,4,5-tetrahydro-1H-benzazepine (1.26 g).

M.p. 110–111° C.

[α]$_D^{25}$: +3.6° (C=0.1, methanol)

Reference Example 13

A mixture of (5S)-5-bromomethyl-1-(p-toluenesulfonyl)-2,3,4,5-tetrahydro-1H-benzazepine (0.83 g), potassium cyanide (0.27 g) and dimethyl sulfoxide (9 ml) is heated with stirring at 45–50° C. for three hours. To the reaction solution is added ice, and the mixture is extracted with ethyl acetate—diethyl ether. The extract is dried over sodium sulfate, and evaporated under reduced pressure to remove the solvent. The resulting residue is purified by silica gel column chromatography (solvent; n-hexane: ethyl acetate=6:1), and recrystallized from ethyl acetate—n-hexane to give (5R)-5-cyanomethyl-1-(p-toluenesulfonyl)-2,3,4,5-tetrahydro-1H-benzazepine (0.60 g).

M.p. 106° C.

Colorless needles

[α]$_D^{25}$: +16.0° (C=0.1, methanol)

Reference Example 14

A mixture of (5R)-5-acetyloxymethyl-1-(p-toluenesulfonyl)-2,3,4,5-tetrahydro-1H-benzazepine (1.49 g), potassium carbonate (1.11 g) and methanol (15 ml) is stirred at room temperature for 20 minutes. The reaction solution is poured into water, and the mixture is extracted with dichloromethane. The extract is dried over sodium sulfate, and concentrated under reduced pressure to give (5S)-5-hydroxymethyl-1-(p-toluenesulfonyl)-2,3,4,5-tetrahydro-1H-benzazepine (1.33 g).

Colorless oil

[α]$_D^{25}$: −8.9° (C=1, chloroform)

$^1$H-NMR (CDCl$_3$, 250 MHz) δ ppm: 1.00–2.25 (4H, br), 2.44 (3H, s), 2.50–3.50 (2H, br), 3.70–4.00 (2H, br), 4.00–4.35 (2H, br), 6.90–7.40 (6H, m), 7.60–7.80 (2H, m)

Optical purity: 98.7% e.e.

Conditions for HPLC analysis of optical purity:

Column: CHIRALCEL OJ (manufactured by DAICEL CHEMICAL INDUSTRIES, LTD.)

Solvent: n-Hexane:isopropyl alcohol:diethyl amine=700:300:1

Detection: UV$_{254nm}$

Chart speed: 1 mm/min.

Retention time: 8.2 minutes (R-isomer), 6.9 minutes (S-isomer)

Reference Example 15

The corresponding starting compounds are treated in the same manner as in Reference Example 12 to give the following compound.

(5R)-5-Bromomethyl-1-(p-toluenesulfonyl)-2,3,4,5-tetrahydro-1H-benzazepine

M.p. 110–111° C. (recrystallized from diethyl ether—n-hexane)

White powder

[α]$_D^{25}$: −2.4° (C=0.1, methanol)

Reference Example 16

The corresponding starting compounds are treated in the same manner as in Reference Example 13 to give the following compound.

(5R)-5-Cyanomethyl-1-(p-toluenesulfonyl)-2,3,4,5-tetrahydro-1H-benzazepine

M.p. 108–111° C. (recrystallized from ethyl acetate—n-hexane)

Colorless needles $[\alpha]_D^{25}$: –16.0° (C=0.1, methanol)

Reference Example 17

The corresponding starting compounds are treated in the same manner as in Reference Example 11 to give the following compound.

(5R)-5-Methoxycarbonylmethyl-1-(p-toluenesulfonyl)-2,3,4,5-tetrahydro-1H-benzazepine Colorless needles $^1$H-NMR (DMSO-$d_6$, 250 MHz) δ ppm: 1.60–1.95 (4H, br), 2.43 (3H, s), 2.50–2.90 (2H, br), 2.90–3.55 (2H, br), 3.64 (3H, s), 3.80–4.40 (1H, br), 7.00–7.40 (6H, m), 7.70–7.85 (2H, m)

Optical purity: 98.8% e.e.

Conditions for HPLC analysis of optical purity:

Column: CHIRALCEL OJ (manufactured by DAICEL CHEMICAL INDUSTRIES, LTD.)

Solvent: n-Hexane:ethanol:trifluoroacetic acid=800:200:3

Detection: $UV_{254nm}$

Chart speed: 1 mm/min.

Retention time: 14.6 minutes (R-isomer), 24.4 minutes (S-isomer)

Reference Example 18

To a solution of 5-carboxymethylidene-1-(p-toluenesulfonyl)-2,3,4,5-tetrahydro-1H-benzazepine (3.0 g) and isopropylamine (2.5 g) in dimethylformamide (30 ml) is added diethyl cyanophosphate (2.1 g), and the mixture is stirred at room temperature for 30 minutes. To the mixture is added water, and the mixture is extracted with ethyl acetate. The extract is washed with water, dried, concentrated, and the precipitated crystals are recrystallized from chloroform—diisopropyl ether to give 5-isopropylaminomethylidene-1-(p-toluenesulfonyl)-2,3,4,5-tetrahydro-1H-benzazepine (trans-compound) (3.2 g).

White powder $^1$H-NMR (DMSO-$d_6$, 250 MHz) δ ppm: 1.09 (6H, d, J=6.6 Hz), 1.55–1.75 (2H, m), 2.35 (3H, s), 2.77 (2H, br), 3.60–3.73 (2H, m), 3.84 (1H, sextet, J=7.0 Hz), 5.48 (1H, s), 7.14–7.50 (8H, m), 7.73 (1H, d, J=7.3 Hz)

The corresponding starting compounds are treated in the same manner as in Reference Example 18 to give the following compounds.

5-Isopropylaminocarbonylmethyl-1-(p-toluenesulfonyl)-2,3-dihydro-1H-benzazepine

White powder (recrystallized from chloroform—diisopropyl ether)

$^1$H-NMR (DMSO-$d_6$, 200 MHz) δ ppm: 1.03 (6H, d, J=6.6 Hz), 1.95–2.20 (2H, m), 2.38 (3H, s), 2.70 (2H, s), 3.70–4.20 (3H, m), 5.83 (1H, t, J=6.2 Hz), 7.20–7.45 (6H, m), 7.49 (2H, d, J=8.3 Hz), 7.64 (1H, d, J=7.8 Hz)

5-Isopropylaminocarbonylmethylidene-1-(p-toluenesulfonyl)-2,3,4,5-tetrahydro-1H-benzazepine (cis-compound)

White powder (recrystallized from chloroform—diisopropyl ether)

$^1$H-NMR (DMSO-$d_6$, 200 MHz) δ ppm: 0.82 (6H, d, J=6.5 Hz), 1.77 (2H, br), 2.29 (2H, br), 2.41 (3H, s), 3.50–3.90 (3H, m), 5.91 (1H, s), 6.73 (1H, d, J=7.8 Hz), 6.79–6.92 (1H, m), 7.00–7.55 (5H, m), 7.71 (2H, d, J=8.1 Hz)

Example 1

A suspension of 5-methoxycarbonylmethyl-1-(4-amino-2-chlorobenzoyl)-2,3,4,5-tetrahydro-1H-benzazepine (50 g), n-iodopropane (130 ml) and sodium carbonate (185 g) in dimethylformamide (1.0 liter) is stirred overnight at 60° C. To the mixture is added ethyl acetate, and the mixture is washed with water, dried, concentrated, and purified by silica gel column chromatography (solvent; dichloromethane:methanol=50:1) to give 5-methoxycarbonylmethyl-1-(4-n-propylamino-2-chlorobenzoyl)-2,3,4,5-tetrahydro-1H-benzazepine (30 g) as a white powder.

The above product, 5-methoxycarbonylmethyl-1-(4-n-propylamino-2-chlorobenzoyl)-2,3,4,5-tetrahydro-1H-benzazepine (880 mg) is dissolved in ethanol (20 ml), and thereto is added a 6N aqueous sodium hydroxide solution (1 ml), and the mixture is stirred overnight at room temperature. The mixture is acidified with hydrochloric acid, and extracted with ethyl acetate. The extract is dried, and concentrated to give 5-carboxymethyl-1-(4-n-propylamino-2-chlorobenzoyl)-2,3,4,5-tetrahydro-1H-benzazepine (800 mg) as a white powder.

To a solution of the above product, 5-carboxymethyl-1-(4-n-propylamino-2-chlorobenzoyl)-2,3,4,5-tetrahydro-1H-benzazepine (800 mg) and isopropylamine (1.0 ml) in dimethylformamide (20 ml) is added dropwise diethyl cyanophosphate (391 mg) at room temperature. The mixture is stirred overnight, and thereto is added ethyl acetate. The mixture is washed with water, dried, concentrated, and purified by silica gel column chromatography (solvent; dichloromethane:methanol=50:1), and further crystallized from diethyl ether to give 5-isopropylaminocarbonylmethyl-1-(4-n-propylamino-2-chlorobenzoyl)-2,3,4,5-tetrahydro-1H-benzazepine (840 mg).

M.p. 140–143° C.

Using the suitable starting compounds, the following compounds listed in Table 1 are obtained in the same manner as in Example 1. Table 2 shows the NMR analysis data of these compounds.

TABLE 1

[Structure: benzazepine core with R¹ on benzene ring, ACONR²R³ at 5-position, and N-CO-phenyl(R⁴,R⁵) substituent]

Example 2

R¹: 7-Cl    R⁴: 3-OCH₃    R⁵: 4—NHCH₂CH(CH₃)₂

—ACONR²R³: —CH₂CONHCH(CH₃)₂

Crystalline form: Colorless amorphous    Form: Free

Example 3

R¹: 7-Cl    R⁴: 2-Cl    R⁵: 4—NHCH(CH₃)₂

—ACONR²R³: —CH₂CO—N(piperazine)N—CH₃

M.p.: 174–176° C.

Crystalline form: Colorless needles    Form: Free

Recrystallization solvent: Dichloromethane-diethyl ether-n-hexane

Example 4

R¹: 7-Cl    R⁴: 2-Cl    R⁵: 4—NHCH(CH₃)₂

—ACONR²R³: —CH₂CONHCH(CH₃)₂

Crystalline form: Colorless amorphous    Form: Free

Example 5

R¹: H    R⁴: 2-Cl    R⁵: 4-NH(CH₂)₃CH₃

—ACONR²R³: —CH₂CONH-(3-pyridyl)

Crystalline form: Colorless amorphous    Form: Free

TABLE 1-continued

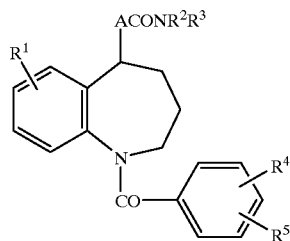

Example 6

R¹: H            R⁴: 2-Cl            R⁵: 4-NHC₂H₅

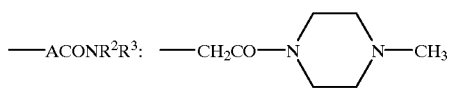

Crystalline form: Colorless amorphous            Form: Dihydrochloride

Example 7

R¹: H            R⁴: 2-Cl            R⁵: 4-NHC₂H₅

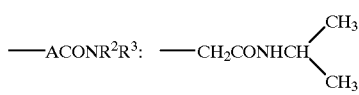

M.p.: 176–178° C.
Crystalline form: White powder            Form: Free
Recrystallization solvent: Acetone-diethyl ether Example 8

R¹: H            R⁴: 2-Cl            R⁵: 4-NHC₂H₅

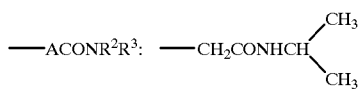

M.p.: 193–195° C.
Crystalline form: White powder            Form: Free
Recrystallization solvent: Diethyl ether Example 9

R¹: H            R⁴: 2-Cl            R⁵: 4-NH(CH₂)₂CH₃

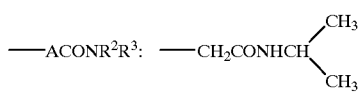

M.p.: 140–143° C.
Crystalline form: White powder            Form: Free
Recrystallization solvent: Diethyl ether Example 10

R¹: H            R⁴: 2-Cl            R⁵: 4-NH(CH₂)₄CH₃

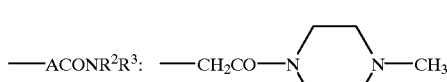

Crystalline form: Colorless amorphous            Form: Dihydrochloride

Example 11

R¹: H            R⁴: 2-Cl            R⁵: 4-NH(CH₂)₄CH₃

TABLE 1-continued

[Structure: benzazepine core with R¹ on aromatic ring, ACONR²R³ substituent at position 5, and N-CO-phenyl group with R⁴ and R⁵ substituents]

—ACONR²R³: —CH₂CONHCH(CH₃)(CH₃)

Crystalline form: Colorless amorphous    Form: Hydrochloride

Example 12

R¹: H    R⁴: 2-Cl    R⁵: 4-NH(CH₂)₂CH₃

—ACONR²R³: —CH₂CO—N(pyrrolidine)

M.p.: 94–97° C.
Crystalline form: White powder    Form: Free
Recrystallization solvent: Chloroform-diethyl ether-n-hexane Example 13

R¹: H    R⁴: 2-Cl    R⁵: 4-NH(CH₂)₂CH₃
—ACONR²R³: —CH₂CONHCH₂CH₂OCH₃
M.p.: 118–119° C.
Crystalline form: White powder    Form: Free
Recrystallization solvent: Chloroform-diethyl ether-n-hexane Example 14

R¹: H    R⁴: 2-Cl    R⁵: 4-NH(CH₂)₂CH₃

—ACONR²R³: —CH₂CONHCH₂CH(CH₃)(CH₃)

M.p.: 155–156° C.
Crystalline form: White powder    Form: Free
Recrystallization solvent: Chloroform-diethyl ether-n-hexane Example 15

R¹: H    R⁴: 2-Cl    R⁵: 4-NH(CH₂)₂CH₃

—ACONR²R³: —CH₂CO—N(piperazine)N—CH₃

Crystalline form: Colorless amorphous    Form: Free

Example 16

R¹: H    R⁴: 2-Cl    R⁵: 4-NH(CH₂)₂CH₃

—ACONR²R³: —CH₂CON((CH₂)₂OCH₃)((CH₂)₂OCH₃)

Crystalline form: Colorless viscous oil

Example 17

R¹: H    R⁴: 2-Cl    R⁵: 4-NH(CH₂)₂CH₃

TABLE 1-continued

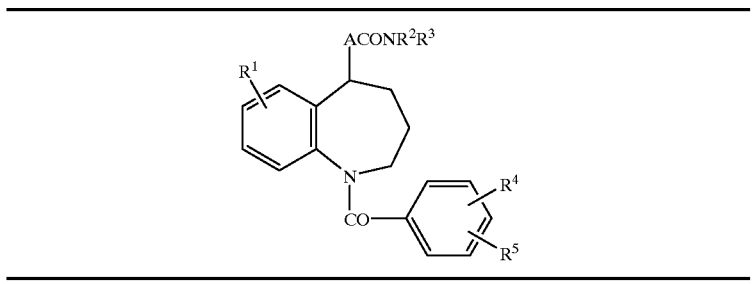

—ACONR²R³: 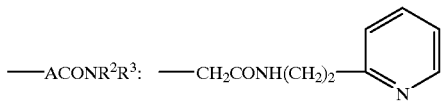

Crystalline form: Colorless amorphous        Form: Free
Example 18

R¹: H                R⁴: 2-Cl              R⁵: 4-NH(CH₂)₂CH₃

—ACONR²R³: 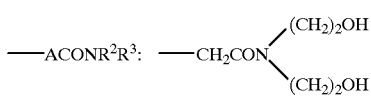

Crystalline form: Colorless amorphous        Form: Free
Example 19

R¹: H                R⁴: 2-Cl              R⁵: 4-NH(CH₂)₂CH₃

—ACONR²R³: —CH₂CONHC₂H₅
Crystalline form: Colorless amorphous        Form: Free
Example 20

R¹: H                R⁴: 2-Cl              R⁵: 4-NH(CH₂)₂CH₃

—ACONR²R³: 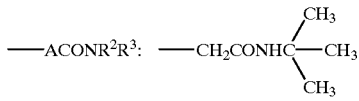

Crystalline form: Colorless amorphous        Form: Free
Example 21

R¹: H                R⁴: 2-Cl              R⁵: 4-NH(CH₂)₂CH₃

—ACONR²R³: 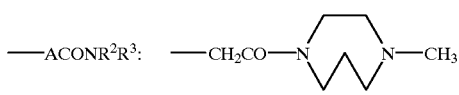

Crystalline form: Colorless amorphous        Form: Free
Example 22

R¹: H                R⁴: 2-Cl              R⁵: 4-NH(CH₂)₂CH₃

—ACONR²R³: 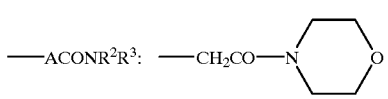

Crystalline form: Colorless amorphous        Form: Free
Example 23

R¹: H                R⁴: 2-Cl              R⁵: 4-NH(CH₂)₂CH₃

—ACONR²R³: —CH₂CONHOCH₃
Crystalline form: Colorless amorphous        Form: Free
Example 24

R¹: H                R⁴: 2-Cl              R⁵: 4-NH(CH₂)₂CH₃

TABLE 1-continued

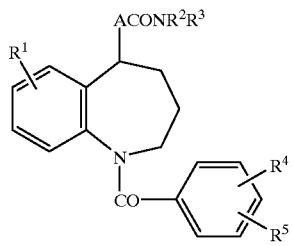

—ACONR²R³: —CH₂CONH₂
M.p.: 196–198° C.
Crystalline form: White powder                     Form: Free Example 25

R¹: H                 R⁴: 2-Cl                 R⁵: 4-NH(CH₂)₂CH₃

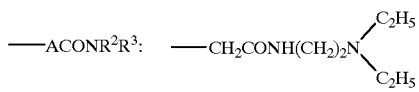

Crystalline form: Colorless amorphous              Form: Free

Example 26

R¹: H                 R⁴: 2-Cl                 R⁵: 4-NH(CH₂)₂CH₃

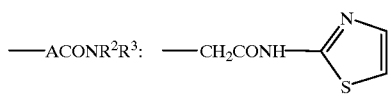

Crystalline form: Colorless amorphous              Form: Free

Example 27

R¹: H                 R⁴: 2-Cl                 R⁵: 4-NH(CH₂)₂CH₃

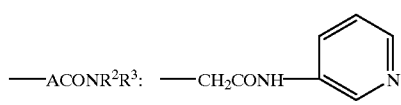

Crystalline form: Colorless amorphous              Form: Free

Example 28

R¹: H                 R⁴: 2-Cl                 R⁵: 4-NH(CH₂)₂CH₃

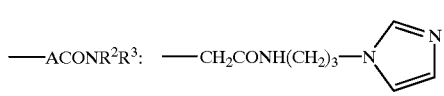

Crystalline form: Colorless amorphous              Form: Free

Example 29

R¹: H                 R⁴: 2-Cl                 R⁵: 4-NH(CH₂)₂CH₃

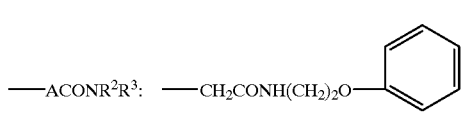

M.p.: 122.5–123.5° C.
Crystalline form: White powder                     Form: Free
Recrystallization solvent: Chloroform-diethyl ether Example 30

R¹: H                 R⁴: 2-Cl

R⁵: 4—

TABLE 1-continued

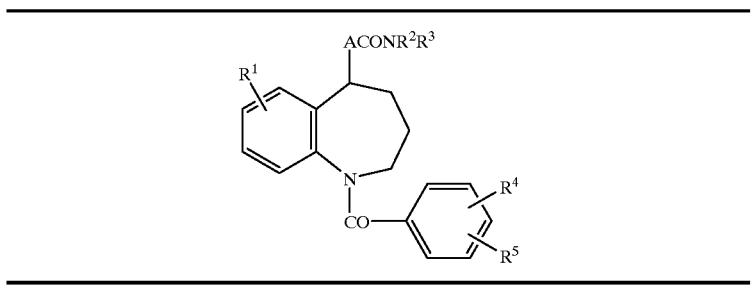

—ACONR²R³: 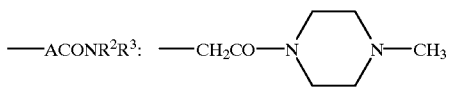

Crystalline form: Colorless amorphous  Form: Free
Example 31

R¹: H        R⁴: 2-Cl        R⁵: 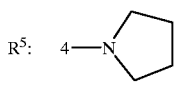

—ACONR²R³: 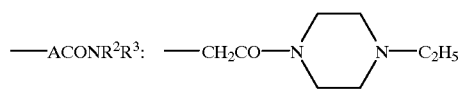

Crystalline form: Colorless amorphous  Form: Hydrochloride
Example 32

R¹: H        R⁴: 2-Cl        R⁵: 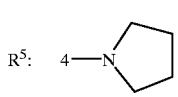

—ACONR²R³: 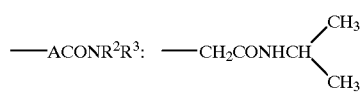

M.p.: 191° C.
Crystalline form: White powder  Form: Free
Recrystallization solvent: Acetone-diethyl ether
Example 33

R¹: 7-Cl     R⁴: 2-Cl        R⁵: 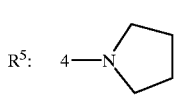

—ACONR²R³: 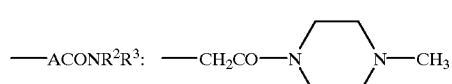

Crystalline form: Colorless amorphous  Form: Hydrochloride
Example 34

R¹: 7-Cl     R⁴: 2-Cl        R⁵: 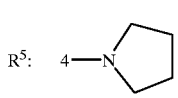

—ACONR²R³: 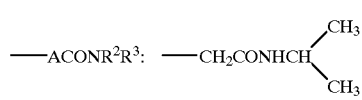

Crystalline form: Colorless amorphous  Form: Free

TABLE 1-continued

[Structure: benzazepine core with R¹ on benzene ring, ACONR²R³ substituent, N-CO-phenyl with R⁴ and R⁵ on phenyl]

Example 35

R¹: H  R⁴: 2-Cl

R⁵: 4—[pyrrolidin-1-yl]

—ACONR²R³: —CH₂CONH(CH₂)₂N(C₂H₅)(C₂H₅)

Crystalline form: Colorless amorphous  Form: Hydrochloride

Example 36

R¹: H  R⁴: 2-Cl

R⁵: 4—[pyrrolidin-1-yl]

—ACONR²R³: —CH₂CO—[piperazin-1-yl]—N—CH₃

Crystalline form: Colorless amorphous  Form: Hydrochloride

Example 37

R¹: H  R⁴: 2-Cl

R⁵: 4—[pyrrolidin-1-yl]

—ACONR²R³: —CH₂CON(CH₃)(CH₂)₂N(C₂H₅)(C₂H₅)

Crystalline form: Colorless amorphous  Form: Hydrochloride

Example 38

R¹: H  R⁴: 2-Cl

R⁵: 4—[pyrrolidin-1-yl]

—ACONR²R³: —CH₂CONHC₂H₅
M.p.: 159–161° C.
Crystalline form: White powder  Form: Free
Recrystallization solvent: Acetone-diethyl ether Example 39

R¹: H  R⁴: 2-Cl

R⁵: 4—[pyrrolidin-1-yl]

—ACONR²R³: —CH₂CON(C₂H₅)(C₂H₅)

TABLE 1-continued

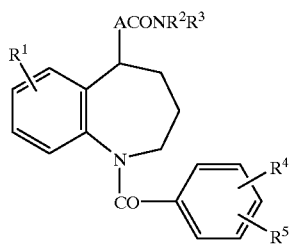

M.p.: 123–124° C.
Crystalline form: Pale yellow powder
Recrystallization solvent: Acetone
Form: Free Example 40

R$^1$: H         R$^4$: 2-Cl         R$^5$: 4—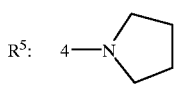

—ACONR$^2$R$^3$: —CH$_2$CONH$_2$
M.p.: 222–224° C.
Crystalline form: White powder
Recrystallization solvent: Ethanol-diethyl ether
Form: Free Example 41

R$^1$: H         R$^4$: H         R$^5$: 4—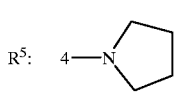

—ACONR$^2$R$^3$: —CH$_2$CONHCH(CH$_3$)$_2$

M.p.: 92–95° C.
Crystalline form: White powder
Recrystallization solvent: Diethyl ether
Form: Free Example 42

R$^1$: H         R$^4$: H         R$^5$: 4—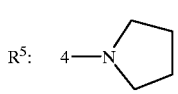

—ACONR$^2$R$^3$: —CH$_2$CONH$_2$
Crystalline form: Colorless amorphous
Form: Free Example 43

R$^1$: H         R$^4$: 2-Cl         R$^5$: 4—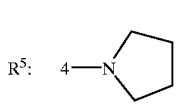

—ACONR$^2$R$^3$: —CH$_2$CONHCH$_2$CONH$_2$
Crystalline form: White powder
Recrystallization solvent: Acetone-diethyl ether
Form: Free Example 44

R$^1$: H         R$^4$: 2-Cl         R$^5$: 4—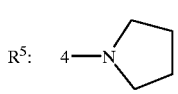

—ACONR$^2$R$^3$: —CH$_2$CONH-(thiazol-2-yl)

M.p.: 209–210° C. (decomposed)
Crystalline form: Yellow powder
Recrystallization solvent: Acetone-diethyl ether
Form: Free TABLE 1-continued

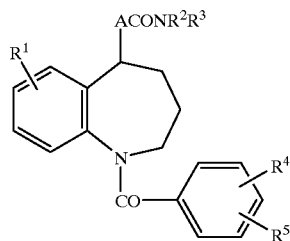

Example 45

R¹: H  R⁴: 2-Cl

R⁵: 4—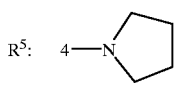

ACONR²R³: —CH₂CONH(CH₂)₂OCH₃
M.p.: 178–179° C.
Crystalline form: White powder  Form: Free
Recrystallization solvent: Acetone-diethyl ether Example 46

R¹: H  R⁴: 2-Cl

R⁵: 4—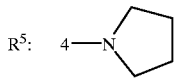

—ACONR²R³: —CH₂CH₂CONHCH(CH₃)₂

M.p.: 194–195° C.
Crystalline form: White powder  Form: Free
Recrystallization solvent: Acetone-diethyl ether Example 47

R¹: H  R⁴: 2-Cl

R⁵: 4—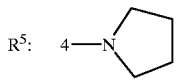

—ACONR²R³: —CH₂CONH—(3-pyridyl)

M.p.: 237–238° C.
Crystalline form: White powder
Recrystallization solvent: Acetone-diethyl ether Example 48

R¹: H  R⁴: 2-Cl

R⁵: 4—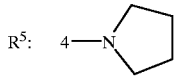

—ACONR²R³: —CH₂CON(C₂H₅)₂

Crystalline form: Colorless amorphous  Form: Free

Example 49

R¹: H  R⁴: 2-Cl

R⁵: 4—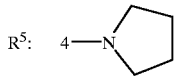

TABLE 1-continued

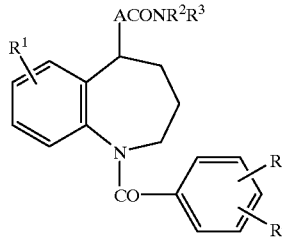

| —ACONR²R³: | —CH₂CH₂CO—N⟨ ⟩N—CH₃ |

| Crystalline form: Colorless amorphous | Form: Free |

Table 2
Data of NMR analysis:

Example 2

$^1$H-NMR (CDCl$_3$) δ ppm: 0.4–1.4, 1.4–2.4, 2.4–2.85, 2.85–3.3, 3.3–5.0 and 5.0–5.8 (total 29H, m), 6.29 and 6.5–7.5 [total 6H, m, 6.29 (d, J=8.4 Hz)]

Example 4

$^1$H-NMR (CDCl$_3$) δ ppm: 0.59 (3H, d, J=6.5 Hz), 0.97 (3H, d, J=6.5 Hz), 1.1–2.7, 2.8–3.1 and 3.25–4.0 [total 16H, m, 3.02 (s)], 6.4–6.7 and 7.15–7.35 (total 7H, m)

Example 5

$^1$H-NMR (CDCl$_3$) δ ppm: 1.65–4.65 [total 29H, m, 2.35 (s)], 5.85–7.68 (total 7H, m)

Example 6

$^1$H-NMR (DMSO-d$_6$) δ ppm: 0.69–2.28 {7H, m [1.08 (t), 1.19 (t)]}, 2.30–5.02 (18H, m), 5.52–7.61 (9H, m), 11.08–11.71 (1H, m)

Example 10

$^1$H-NMR (DMSO-d$_6$) δ ppm: 0.70–2.08, 2.30–3.75 and 4.15–4.66 {total 31H, m [2.75 (s)]}, 6.12–7.65 (9H, m), 11.2–11.7 (1H, m)

Example 11

$^1$H-NMR (DMSO-d$_6$) δ ppm: 0.50–2.05, 2.22–4.00, 4.18–4.50, 4.80–4.98 and 5.50–5.70 {total 27H, m [3.84 (t, J=6.85 Hz), 4.33 (t, J=7.7 Hz)]}, 6.15–7.58 and 7.82–8.11 (total 10H, m), 8.38–9.50 (1 H, m)

Example 15

$^1$H-NMR (CDCl$_3$) δ ppm: 0.80–1.10, 1.10–1.42, 1.42–4.20, 4.42–4.60 and 4.95–5.15 {total 27H, m [2.17 (s), 2.33 (s)]}, 5.95–6.22 (1H, m), 6.38–7.50 (7H, m)

Example 16

$^1$H-NMR (CDCl$_3$) δ ppm: 0.75–1.12, 1.15–1.47, 1.47–2.32, 2.49–4.60 and 4.92–5.08 {total 30H, m [3.30 (s), 3.42 (s)]}, 6.75–7.90 (8H, m)

Example 17

$^1$H-NMR (CDCl$_3$) δ ppm: 0.82–1.10, 1.10–1.38, 1.38–2.18, 2.18–4.20 and 4.38–4.55 (total 20H, m), 6.00–6.21 and 6.38–6.70 (total 2H, m), 6.75–7.70 (10H, m), 8.38–8.58 (1H, m)

Example 18

$^1$H-NMR (CDCl$_3$) δ ppm: 0.80–1.10, 1.15–2.40 and 2.65–4.70 [total 27H, m, 1.02 (t, J=7.2 Hz), 1.67 (q, J=7.2 Hz)], 6.05–6.18, 6.40–6.70 and 6.80–7.50 (total 7H, m)

Example 19

$^1$H-NMR (CDCl$_3$) δ ppm: 0.65 (3H, t, J=7.3 Hz), 0.85–1.50, 1.50–2.15, 2.15–2.50 and 2.50–4.20 [total 19H, m, 1.02 (t, J=7.3 Hz)], 6.50–6.75 [total 3H, m, 6.55 (dd, J=2.2 Hz, 8.3 Hz), 6.63 (d, J=2.2 Hz)], 7.10–7.40 (5H, m)

Example 20

$^1$H-NMR (CDCl$_3$) δ ppm: 0.90–1.10, 1.25–1.50, 1.50–2.25, 2.30–2.85, 2.85–3.20, 3.30–3.55 and 3.70–4.10 [total 26H, m, 0.999 (s)], 6.41 (1H, brs), 6.50–6.65 (2H, m), 7.10–7.45 (5H, m)

Example 21

$^1$H-NMR (CDCl$_3$) δ ppm: 0.85–1.10, 1.18–1.42, 1.42–2.20, 2.20–4.10 and 4.45–4.60 (total 30H, m), 5.95–6.23 (1H, m), 6.36–6.70 (3H, m), 6.80–7.50 (3H, m)

Example 22

$^1$H-NMR (CDCl$_3$) δ ppm: 0.80–1.11, 1.15–2.20, 2.30–2.50, 2.50–4.20, 4.42–4.65 and 4.95–5.15 (total 25H, m), 6.00 and 6.17 (1H, dd, J=2.3 Hz, 8.5 Hz), 6.38–6.67 and 6.67–7.40 (total 6H, m)

Example 23

$^1$H-NMR (CDCl$_3$) δ ppm: 0.85–1.13, 1.50–2.12, 2.12–2.35, 2.35–2.90, 2.90–3.30 and 3.30–4.20 [total 20H, m, 1.03 (t, J=7.3 Hz)], 6.55 (1H, dd, J=2.2 Hz, 8.3 Hz), 6.63 (1H, d, J=2.2 Hz), 7.12–7.45 (5H, m), 9.53 (1H, s)

Example 25

$^1$H-NMR (CDCl$_3$) δ ppm: 0.85–1.40, 1.40–4.10 and 4.40–4.60 (total 31H, m), 6.12–6.20 and 6.38–7.50 (total 8H, m)

Example 26

$^1$H-NMR (CDCl$_3$) δ ppm: 0.85–1.10, 1.45–2.20, 2.48–2.65 and 2.80–4.61 [total 17H, m, 1.03 (t, J=7.3 Hz)], 6.02–6.10 and 6.35–7.48 (9H, m), 10.60–11.59 (1H, brs)

Example 27

¹H-NMR (CDCl₃) δ ppm: 0.90–1.10, 1.55–2.20, 2.35–2.55, 2.62–3.60 and 3.90–4.20 [total 17H, m, 1.03 (t, J=7.2 Hz)], 6.57 (1H, dd, J=2.2 Hz, 8.4 Hz), 6.65 (1H, d, J=2.2 Hz), 6.96–7.50 (6H, m), 7.65–7.78 (1H, m), 8.18 (1H, dd, J=1.5 Hz, 4.8 Hz), 8.33 (1H, d, J=2.3 Hz), 8.89 (1H, s)

Example 28

¹H-NMR (CDCl₃) δ ppm: 0.90–1.10, 1.20–2.10, 2.20–2.40, 2.50–3.60 and 3.90–4.20 [total 23H, m, 1.03 (t, J=6.7 Hz)], 6.57 (1H, dd, J=2.2 Hz, 8.4 Hz), 6.65 (1H, d, J=2.2 Hz), 6.76–6.95 (2H, m), 6.98 (1H, s), 7.08–7.38 (5H, m), 7.42 (1H, s)

Example 30

¹H-NMR (DMSO-d₆) δ ppm: 0.94–2.25 (8H, m), 2.31–5.02 (20H, m), 5.99–7.56 [total 7H, m, 6.11 (d, J=8.8 Hz)], 11.04–11.60 (1H, brs)

Example 31

¹H-NMR (DMSO-d₆) δ ppm: 0.92–2.27 [total 11H, m, 1.28 (t, J=7.2 Hz)], 2.32–5.00 (19H, m), 6.01–7.53 [total 7H, m, 6.11 (d, J=8.8 Hz)], 10.98–11.62 (1H, brs)

Example 33

¹H-NMR (DMSO-d₆) δ ppm: 0.98–2.10 (8H, m), 2.37–3.76, 4.17–4.62 and 4.78–4.99 (total 20H, m), 6.10–7.55 [total 6H, m, 6.17 (d, J=8.3 Hz)], 11.15–11.58 (1H, brs)

Example 34

¹H-NMR (CDCl₃) δ ppm: 0.59 and 0.99 (each 3H, each d, J=6.5 Hz, 2.6 Hz), 1.08–1.33, 1.42–2.39 and 2.40–4.09 (total 18H, m), 6.08–7.41 (7H, m)

Example 35

¹H-NMR (DMSO-d₆) δ ppm: 1.04–2.20 (14H, m), 2.39–3.84, 4.15–4.43 and 4.80–5.02 (total 17H, m), 6.05–7.55 (7H, m), 8.43–8.67 (1H, m), 9.85–10.23 (1H, m)

Example 36

¹H-NMR (DMSO-d₆) δ ppm: 0.90–4.50 (30H, m), 6.01–7.50 (7H, m), 10.54–11.10 (1H, m)

Example 37

¹H-NMR (DMSO-d₆) δ ppm: 0.99–2.22 (14H, m), 2.42–4.49 (20H, m), 5.98–7.39 (7H, m), 9.72–10.11 (1H, m)

Example 42

¹H-NMR (CDCl₃) δ ppm: 1.16–2.40 (8H, m), 2.47–5.78 (11H, m), 5.95–7.69 (8H, m)

Example 48

¹H-NMR (CDCl₃) δ ppm: 0.95–2.40, 2.80–3.40, 3.75–4.42 and 5.20–5.45 (total 26H, m), 5.95–6.19 and 6.30–7.45 (total 7H, m)

Example 49

¹H-NMR (CDCl₃) δ ppm: 1.10–2.60, 2.80–4.00, 4.22–4.41 and 5.03–5.20 [total 30H, m, 2.32 (s), 1.95 (s)], 5.97–6.18 (1H, m), 6.26–7.45 (6H, m)

Example 50

5-Carboxymethyl-2,3-dihydro-1-(p-toluenesulfonyl)-1H-benzazepine (120 g) and [(S)-(−)-2,2'-bis (diphenylphosphino)-1,1'-binaphthyl]ruthenium (II) acetate [Ru(OCOCH₃)₂-(S)-BINAP] (1.41 g) are dissolved in degassed dry methanol (400 ml), and the mixture is stirred for 36 hours under a pressure of 4 atms of hydrogen gas. After the reaction is completed, the mixture is evaporated under reduced pressure to remove the methanol, and the resulting residue is dissolved in toluene (2 liters), and extracted with a 1N aqueous sodium hydroxide solution. The extract is acidified with conc. hydrochloric acid, and extracted twice with ethyl acetate (each 2 liters), dried over magnesium sulfate, and concentrated under reduced pressure to remove the solvent to give (5R)-5-carboxymethyl-1-(p-toluenesulfonyl)-2,3,4,5-tetrahydro-1H-benzazepine (118 g).

White solid

¹H-NMR (DMSO-d₆, 200 MHz) δ ppm: 1.26–2.00 (3H, br), 2.41 (3H, s), 2.52–2.80, 2.80–4.30 (total 6H, m), 6.90–7.09 (1H, br), 7.09–7.33 (3H, m), 7.35–7.55 (2H, m), 7.60–7.90 (2H, m), 12.18 (1H, s)

Optical purity: 76% e.e.

Conditions for HPLC analysis of optical purity:

Column: CHIRALPAK AD (manufactured by DAICEL CHEMICAL INDUSTRIES, LTD.) 4.6 mm×250 mm Solvent: n-Hexane:ethanol:trifluoroacetic acid=900:100:3

Detection: $UV_{254nm}$

Flow rate: 1.0 ml/min.

Retention time: 15 minutes (R-isomer), 14 minutes (S-isomer)

Example 51

To a solution of (5R)-5-carboxymethyl-1-(p-toluenesulfonyl)-2,3,4,5-tetrahydro-1H-benzazepine (115.6 g) in dry dichloromethane (700 ml) are added thionyl chloride (70 ml) and 1-methyl-2-pyrrolidone (1 ml), and the mixture is refluxed with stirring for three hours. The solution is added dropwise into a solution of isopropylamine (274 ml) in dichloromethane (300 ml) under ice-cooling, and the mixture is stirred for 12 hours. The mixture is evaporated under reduced pressure to remove the dichloromethane, and to the residue is added a 3N aqueous sodium hydroxide solution (1 liter), and the mixture is extracted with ethyl acetate. The organic layer is washed with water, dried over anhydrous magnesium sulfate, and concentrated under reduced pressure. The residue is recrystallized from a 75% aqueous methanol (700 ml) to give (5R)-5-isopropylaminocarbonylmethyl-1-(p-toluenesulfonyl)-2,3,4,5-tetrahydro-1H-benzazepine (63.2 g).

M.p. 131–133° C.

$[\alpha]_D$: −21.8° (c=0.5, ethanol)

Optical purity: >99% e.e.

Conditions for HPLC analysis of optical purity:

Column: CHIRALCEL OD-R (manufactured by DAICEL CHEMICAL INDUSTRIES, LTD.) 4.6 mm×250 mm Solvent: Acetonitrile:0.5M aqueous sodium perchloride=1:1

Detection: $UV_{254nm}$

Flow rate: 1.0 ml/min.

Retention time: 11 minutes (R-isomer), 10 minutes (S-isomer)

Example 52

A mixture of (5S)-5-isopropylaminocarbonylmethyl-1-(p-toluenesulfonyl)-2,3,4,5-tetrahydro-1H-benzazepine (1 g), anisole (1 g) and conc. sulfuric acid (2 ml) is stirred at 98–104° C. (external temperature) for 3.5 hours. The mixture is diluted with water (60 ml), washed with diethyl ether, and the pH value of the aqueous layer is adjusted to pH 9–10 with an aqueous sodium hydroxide. The mixture is extracted twice with ethyl acetate (100 ml), and the ethyl acetate layer is washed with an aqueous sodium chloride solution, dried over magnesium sulfate, and concentrated under reduced pressure to remove the solvent to give an oily product (630 mg). The product thus obtained is crystallized from a small amount of ethyl acetate—n-hexane (1:15). The precipitated crystals are collected by filtration, recrystallized from ethyl acetate—n-hexane to give (5S)-5-isopropylaminocarbonylmethyl-2,3,4,5-tetrahydro-1H-benzazepine (470 mg).

White powder

M.p. 91–92° C.

$[\alpha]_D^{25}$: +81.891° (c=1.005, ethanol)

Optical purity: >99% e.e.

Conditions for HPLC analysis of optical purity:

Column: CHIRALCEL OD-R (manufactured by DAICEL CHEMICAL INDUSTRIES, LTD.) 4.6 mm×250 mm Solvent: Acetonitrile:0.5M aqueous sodium perchloride=35:65

Detection: $UV_{254nm}$

Flow rate: 1.0 ml/min.

Retention time: 12 minutes (R-isomer), 7 minutes (S-isomer)

Example 53

To 2-chloro-4-pyrrolidinylbenzoic acid (1 g) is added thionyl chloride (10 ml), and a drop of N-methylpyrrolidone is added to the mixture. The mixture is stirred at room temperature for one hour. Subsequently, the mixture is concentrated under reduced pressure, and the residue is dissolved in toluene (10 ml), and further concentrated under reduced pressure to give 2-chloro-4-pyrrolidinylbenzoyl chloride (acid chloride) as a pale yellow powder. Separately, (5R)-5-isopropylaminocarbonylmethyl-2,3,4,5-tetrahydro-1H-benzazepine (1 g) is dissolved in dichloromethane (20 ml), and thereto is added pyridine (1.64 ml). To the mixture is added drowpise with stirring a solution of the above obtained acid chloride in dichloromethane (5 ml) at room temperature. The mixture is stirred for one hour, and thereto is added 1N aqueous sodium hydroxide solution (10 ml), and then stirred for 30 minutes. The mixture is extracted with ethyl acetate (20 ml), and the extract is dried over sodium carbonate, crystallized from acetonitrile, and further recrystallized from acetone—n-hexane to give (5R)-5-isopropylaminocarbonylmethyl-1-[4-(1-pyrrolidinyl)-2-chlorobenzoyl]-2,3,4,5-tetrahydro-1H-benzazepine (0.45 g).

White powder

M.p. 183–184° C.

$[\alpha]_D^{20}$: −144° (c=0.5, ethanol)

Optical purity: >99% e.e.

Conditions for HPLC analysis of optical purity:

Column: CHIRALCEL OD-R (manufactured by DAICEL CHEMICAL INDUSTRIES, LTD.) 4.6 mm×250 mm Solvent: n-Hexane:ethanol=9:1

Detection: $UV_{254nm}$

Flow rate: 1.0 ml/min.

Retention time: 9 minutes (R-isomer), 12 minutes (S-isomer)

Example 54

To a suspension of (5R)-5-((R)-2-heptyloxycarbonylmethyl)-1-[4-(1-pyrrolidinyl)-2-chlorobenzoyl]-2,3,4,5-tetrahydro-1H-benzazepine (33 g) in methanol (500 ml) is added a 5N aqueous sodium hydroxide solution (25.8 ml), and the mixture is heated with stirring at 40–50° C. for two hours. To the mixture is further added a 5N aqueous sodium hydroxide solution (15 ml), and the mixture is heated with stirring at 50° C. for three hours. The reaction solution is acidified with hydrochloric acid, and concentrated under reduced pressure to remove the methanol, and extracted with ethyl acetate. The ethyl acetate layer is washed with water, dried over magnesium sulfate, and concentrated under reduced pressure to remove the ethyl acetate. The resultant is crystallized from ethyl acetate—diethyl ether, washed with diethyl ether—n-hexane to give (5R)-5-carboxymethyl-1-[4-(1-pyrrolidinyl)-2-chlorobenzoyl]-2,3,4,5-tetrahydro-1H-benzazepine (21.1 g).

White powder

M.p. 191–192° C.

$[\alpha]_D^{22}$: −281.2° (c=0.5, ethanol)

Optical purity: >99% e.e.

Conditions for HPLC analysis of optical purity:

Column: CHIRALCEL OD-R (manufactured by DAICEL CHEMICAL INDUSTRIES, LTD.) 4.6 mm×250 mm Solvent: Acetonitrile:0.5M aqueous sodium perchloride solution (pH=2)=45:55

Detection: $UV_{254nm}$

Flow rate: 1.0 ml/min.

Retention time: 20 minutes (R-isomer), 17 minutes (S-isomer)

Example 55

To a solution of (5R)-5-carboxymethyl-1-[4-(1-pyrrolidinyl)-2-chlorobenzoyl]-2,3,4,5-tetrahydro-1H-benzazepine (21 g) in dimethylformamide (400 ml) are added isopropylamine (21.7 ml) and diethyl cyanophosphate (10 g) at room temperature, and the mixture is stirred at room temperature for two hours. To the reaction solution are added water and ethyl acetate—n-hexane (10:1), and the mixture is extracted twice. The organic layer is washed successively with a 5% citric acid, a saturated aqueous sodium hydrogen carbonate solution, and water, and dried over anhydrous magnesium sulfate. The mixture is concentrated under reduced pressure to remove the solvent, and the resulting residue is purified by silica gel column chromatography (solvent; dichloromethane:methanol:ammonium hydroxide=1000:5:0.2→1000:15:0.5), and recrystallized from acetone—n-hexane to give (5R)-5-isopropylaminocarbonylmethyl-1-[4-(1-pyrrolidinyl)-2-chlorobenzoyl]-2,3,4,5-tetrahydro-1H-benzazepine (12.5 g).

White powder

M.p. 183–184° C.

$[\alpha]_D^{20}$: −144° (c=0.5, ethanol)

Optical purity: >99% e.e.

Conditions for HPLC analysis of optical purity:

Column: CHIRALCEL OD-R (manufactured by DAICEL CHEMICAL INDUSTRIES, LTD.) 4.6 mm×250 mm Solvent: n-Hexane:ethanol=9:1

Detection: $UV_{254nm}$

Flow rate: 1.0 ml/min.

Retention time: 9 minutes (R-isomer), 12 minutes (S-isomer)

Example 56

A mixture of (5R)-5-cyanomethyl-1-(p-toluenesulfonyl)-2,3,4,5-tetrahydro-1H-benzazepine (102 mg), potassium hydroxide (84 mg) and ethylene glycol (2 ml) is heated with stirring at 170–175° C. for 6 hours. The reaction solution is acidified with conc. hydrochloric acid, extracted with ethyl acetate, dried over sodium sulfate, and the resulting residue is purified by silica gel column chromatography (solvent; dichloromethane:methanol;=9:1) to give (5R)-5-carboxymethyl-1-(p-toluenesulfonyl)-2,3,4,5-tetrahydro-1H-benzazepine (108 mg).

Colorless amorphous $^1$H-NMR (DMSO-d$_6$, 250 MHz) δ ppm: 1.26–2.00 (3H, br), 2.41 (3H, s), 2.52–2.80, 2.80–4.30 (total 6H, br), 6.90–7.09 (1H, br), 7.09–7.33 (3H, m), 7.35–7.55 (2H, m), 7.60–7.90 (2H, m), 12.18 (1H, s)

$[α]_D^{25}$: +2.8° (c=0.5, methanol)

Optical purity: 96.8% e.e.

Conditions for HPLC analysis of optical purity:

Column: CHIRALCEL OJ (manufactured by DAICEL CHEMICAL INDUSTRIES, LTD.)

Solvent: n-Hexane:ethanol:trifluoroacetic acid=800:200:3

Detection: UV$_{254nm}$

Chart speed: 1 mm/min.

Retention time: 8.1 minutes (R-isomer), 9.9 minutes (S-isomer)

Example 57

The corresponding starting compounds are treated in the same manner as in Example 56 to give (5S)-5-carboxymethyl-1-(p-toluenesulfonyl)-2,3,4,5-tetrahydro-1H-benzazepine.

Colorless amorphous $^1$H-NMR (DMSO-d$_6$, 250 MHz) δ ppm: 1.26–2.00 (3H, br), 2.41 (3H, s), 2.52–2.80, 2.80–4.30 (total 6H, br), 6.90–7.09 (1H, br), 7.09–7.33 (3H, m), 7.35–7.55 (2H, m), 7.60–7.90 (2H, m), 12.18 (1H, s)

$[α]_D^{25}$: -2.4° (c=0.5, methanol)

Optical purity: 95.4% e.e.

Conditions for HPLC analysis of optical purity:

Column: CHIRALCEL OJ (manufactured by DAICEL CHEMICAL INDUSTRIES, LTD.)

Solvent: n-Hexane:ethanol:trifluoroacetic acid=800:200:3

Detection: UV$_{254nm}$

Chart speed: 1 mm/min.

Retention time: 8.1 minutes (R-isomer), 9.9 minutes (S-isomer)

Example 58

A mixture of (5S)-5-methoxycarbonylmethyl-1-(p-toluenesulfonyl)-2,3,4,5-tetrahydro-1H-benzazepine (0.20 g), a 5% aqueous sodium hydroxide solution (10 ml) and methanol (10 ml) is heated with stirring at 80° C. for three hours. To the reaction solution is added ice, and the mixture is acidified with conc. hydrochloric acid, and extracted with dichloromethane. The extract is dried over sodium sulfate, and concentrated under reduced pressure to remove the solvent to give (5S)-5-carboxymethyl-1-(p-toluenesulfonyl)-2,3,4,5-tetrahydro-1H-benzazepine (0.19 g).

White powder $^1$H-NMR (DMSO-d$_6$, 250 MHz) δ ppm: 1.26–2.00 (3H, br), 2.41 (3H, s), 2.52–2.80, 2.80–4.30 (total 6H, br), 6.90–7.09 (1H, br), 7.09–7.33 (3H, m), 7.35–7.55 (2H, m), 7.60–7.90 (2H, m), 12.18 (1H, s)

Example 59

The corresponding starting compounds are treated in the same manner as in Example 58 to give the compound of Example 56.

Example 60

The corresponding starting compounds are treated in the same manner as in Example 54 to give the following compound.

(5S)-5-Carboxymethyl-1-[4-(1-pyrrolidinyl)-2-chlorobenzoyl]-2,3,4,5-tetrahydro-1H-benzazepine M.p. 191–192° C. (recrystallized from ethyl acetate—n-hexane)

Colorless powder $[α]_D^{24}$: +283.5° (c=0.6, ethanol)

Optical purity: >96.8% e.e.

Conditions for HPLC analysis of optical purity:

Column: CHIRALCEL OD-R (manufactured by DAICEL CHEMICAL INDUSTRIES, LTD.) 4.6 mm×250 mm Solvent: n-Hexane:ethanol:diethylamine=900:100;1

Detection: UV$_{254nm}$

Flow rate: 1.0 ml/min.

Retention time: 20 minutes (R-isomer), 16 minutes (S-isomer)

Example 61

The corresponding starting compounds are treated in the same manner as in Example 55 to give the following compound.

(5S)-5-Isopropylaminocarbonylmethyl-1-[4-(1-pyrrolidinyl)-2-chlorobenzoyl]-2,3,4,5-tetrahydro-1H-benzazepine M.p. 182.5–184.5° C. (recrystallized from ethyl acetate)

White powder $[α]_D^{24}$: +144.27° (c=0.515, ethanol)

Optical purity: 99.8% e.e.

Conditions for HPLC analysis of optical purity:

Column: CHIRALCEL OD-R (manufactured by DAICEL CHEMICAL INDUSTRIES, LTD.) 4.6 mm×250 mm Solvent: n-Hexane:ethanol=9:1

Detection: UV$_{254nm}$

Flow rate: 1.0 ml/min.

Retention time: 9 minutes (R-isomer), 12 minutes (S-isomer)

Example 62

The corresponding starting compounds are treated in the same manner as in Example 51 to give the following compound.

(5S)-5-Isopropylaminocarbonylmethyl-1-(p-toluenesulfonyl)-2,3,4,5-tetrahydro-1H-benzazepine M.p. 131–133° C. (recrystallized from ethyl acetate—n-hexane)

White powder $[α]_D^{25}$: +21.2° (c=0.5, ethanol)

Optical purity: 99% e.e.

Conditions for HPLC analysis of optical purity:

Column: CHIRALCEL OD-R (manufactured by DAICEL CHEMICAL INDUSTRIES, LTD.) 4.6 mm×250 mm Solvent: Acetonitrile:0.5 M aqueous sodium peroxide solution=1:1

Detection: $UV_{254nm}$

Flow rate: 1.0 ml/min.

Retention time: 11 minutes (R-isomer), 10 minutes (S-isomer)

Example 63

The corresponding starting compounds are treated in the same manner as in Example 52 to give the following compound.

(5S)-5-Isopropylaminocarbonylmethyl-2,3,4,5-tetrahydro-1H-benzazepine

M.p. 89.5–91° C.

White powder $[\alpha]_D^{26}$: −85.00° (c=0.52, ethanol)

Optical purity: 99.8% e.e.

Conditions for HPLC analysis of optical purity:

Column: CHIRALCEL OD-R (manufactured by DAICEL CHEMICAL INDUSTRIES, LTD.) 4.6 mm×250 mm Solvent: Acetonitrile:0.5 M aqueous sodium peroxide solution=35:65

Detection: $UV_{254nm}$

Flow rate: 1.0 ml/min.

Retention time: 12 minutes (R-isomer), 7 minutes (S-isomer)

Example 64

5-Isopropylaminocarbonylmethylidene-1-(p-toluenesulfonyl)-2,3,4,5-tetrahydro-1H-benzazepine (trans-compound) (473 mg) and [(S)-(−)-2,2'-bis(diphenylphosphino)-1,1'-binaphthyl]ruthenium (II) acetate (10 mg) are dissolved in degassed dry methanol (9.5 ml), and the mixture is subjected to hydrogenation under a pressure of 5 atms of hydrogen gas for 48 hours. The mixture is concentrated under reduced pressure to remove the solvent to give (5S)-5-isopropylaminocarbonylmethyl-1-(p-toluenesulfonyl)-2,3,4,5-tetrahydro-1H-benzazepine (366 mg).

M.p. 131–133° C.

White powder (recrystallized from ethyl acetate—n-hexane)

$[\alpha]_D^{25}$: −20.8° (c=1, ethanol)

Optical purity: 85.6% e.e.

Conditions for HPLC analysis of optical purity:

Column: CHIRALCEL OD-R (manufactured by DAICEL CHEMICAL INDUSTRIES, LTD.) 4.6 mm×250 mm Solvent: Acetonitrile:0.5 M aqueous sodium peroxide solution=1:1

Detection: $UV_{254nm}$

Flow rate: 1.0 ml/min.

Retention time: 11 minutes (R-isomer), 10 minutes (S-isomer)

Example 65

5-Isopropylaminocarbonylmethyl-1-(p-toluenesulfonyl)-2,3-dihydro-1H-benzazepine is subjected to reduction in the same manner as in Example 64 to give (5R)-5-isopropylaminocarbonylmethyl-1-(p-toluenesulfonyl)-2,3,4,5-tetrahydro-1H-benzazepine (371 mg).

M.p. 131–133° C.

White powder (recrystallized from ethyl acetate—n-hexane)

$[\alpha]_D^{25}$: −20.0° (c=1, ethanol)

Optical purity: 86.8% e.e.

Conditions for HPLC analysis of optical purity:

Column: ULTRON ES-OVM (manufactured by Sinwa Kako Kabushiki Kaisha) 4.6 mm×250 mm Solvent: Acetonitrile:20 mM aqueous potassium hydrogen phosphate solution=15:85

Detection: $UV_{254nm}$

Flow rate: 1.0 ml/min.

Retention time: 12 minutes (R-isomer), 6 minutes (S-isomer)

Example 66

5-Isopropylaminocarbonylmethylidene-1-(p-toluenesulfonyl)-2,3,4,5-tetrahydro-1H-benzazepine (cis-compound) is subjected to reduction in the same manner as in Example 64 to give (5R)-5-isopropylaminocarbonylmethyl-1-(p-toluenesulfonyl)-2,3,4,5-tetrahydro-1H-benzazepine (30 mg).

M.p. 131–133° C.

White powder (recrystallized from ethyl acetate—n-hexane)

$[\alpha]_D^{25}$: −1.17° (c=1, ethanol)

Optical purity: 9% e.e.

Conditions for HPLC analysis of optical purity:

Column: ULTRON ES-OVM (manufactured by Sinwa Kako Kabushiki Kaisha) 4.6 mm×250 mm Solvent: Acetonitrile:20 mM aqueous potassium hydrogen phosphate solution=15:85

Detection: $UV_{254nm}$

Flow rate: 1.0 ml/min.

Retention time: 12 minutes (R-isomer), 6 minutes (S-isomer)

Pharmacological Experiment

Using cells stably expressing human $V_2$ receptor (hereinafter, referred to as $V_2$-HeLa) which are prepared by introducing a gene coding human $V_2$ receptor into HeLa cells derived from human cervical cancer, the vasopressin agonistic activity of the present compound was estimated by using as an index the cAMP amount increased by the present compound.

A DMEM solution (Dulbecco modified Eagle's medium) was previously prepared wherein the pH value thereof was adjusted to pH 7.4 with a 10 mM HEPES containing 1 mM MIBMX (isobutylmethylxanthine) and 0.3% BSA (bovine serum albumin). The subcultured HeLa cells was inoculated into a 24-well plate, and incubated for a few days. The plate was washed twice with an iced phosphate-buffered saline (PBS), and thereto was added the above DMEM solution (200 μl) and a DMEM solution (50 μl) containing a test compound (the compound obtained in Example 30), and the plate was incubated at 37° C. for 10 minutes. In the control group, a DMEM solution (250 μl) was added instead of DMEM solution (200 μl) and the test compound solution (50 μl), and the plate was also incubated at 37° C. for 10 minutes. After the reaction was completed, the reaction solution was removed by suction, and the plate was washed once with an iced PBS. The plate was extracted with a 0.1 N aqueous hydrochloric acid solution (500 μl) to extract the cAMP from the cells, which was stored at −20° C. until the assay. The cAMP amount in each group was determined by using a cAMP Kit (manufactured by YAMASA SHOYU CO., LTD.). The increase ratio (%) of the cAMP amount in the test compound-treated group was calculated based on the cAMP amount of the control group. The result is shown in Table 3.

TABLE 3

| Test Compound | Concentration of test compound (mole concentration) | Increase ratio (%) of the cAMP amount |
| --- | --- | --- |
| Example 30 | 1 × 10⁻⁶ | 419 |

We claim:

1. A benzazepine compound of the formula [1]:

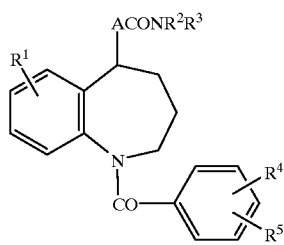

wherein $R^1$ is a hydrogen atom or a halogen atom,
A is a lower alkylene group,
$R^2$ and $R^3$ are the same or different and each are a hydrogen atom, a lower alkoxy group, a lower alkyl group which may have a lower alkoxy substituent, a hydroxy-substituted lower alkyl group, an amino-substituted lower alkyl group which may have a lower alkyl substituent, a carbamoyl-substituted lower alkyl group, a thiazolyl group, a phenoxy-lower alkyl group, a pyridyl group, a pyridyl-lower alkyl group, an imidazolyl-lower alkyl group, or an imidazolyl group which may have a lower alkyl substituent, or $R^2$ and $R^3$ may combine together with the nitrogen atom to which they bond to form a 5- to 7-membered saturated heterocyclic group which may be intervened or not with another nitrogen atom or an oxygen atom, wherein said heterocyclic group may be substituted by a lower alkyl group or a phenyl-lower alkyl group,
$R^4$ is a hydrogen atom, a lower alkyl group, a hydroxy group, an amino group which may have a lower alkanoyl substituent, a nitro group, a halogen atom or a lower alkoxy group, and
$R^5$ is a group of the formula: —NHR⁶ (wherein R⁶ is a lower alkyl group) or a pyrrolidinyl group,
provided that when $R^5$ is a pyrrolidinyl group, $R^2$ and $R^3$ should not be a lower alkoxy group or an amino-substituted lower alkyl group which may have a lower alkyl substituent,
or a salt thereof.

2. The benzazepine compound according to claim 1, wherein $R^1$ is a hydrogen atom, or a salt thereof.

3. The benzazepine compound according to claim 1, wherein $R^1$ is a halogen atom, or a salt thereof.

4. The benzazepine compound according to claim 2, wherein $R^2$ and $R^3$ are the same or different, and each are a hydrogen atom, a lower alkoxy group, a lower alkyl group which may have a lower alkoxy substituent, a hydroxy-substituted lower alkyl group, an amino-substituted lower alkyl group which may have a lower alkyl substituent, a carbamoyl-substituted lower alkyl group, a thiazolyl group, a phenoxy-lower alkyl group, a pyridyl group, a pyridyl-lower alkyl group, an imidazolyl-lower alkyl group, or an imidazolyl group which may have a lower alkyl substituent, or a salt thereof.

5. The benzazepine compound according to claim 2, wherein $R^2$ and $R^3$ combine together with the nitrogen atom to which they bond to form a 5- to 7-membered saturated heterocyclic group which may be intervened or not with another nitrogen atom or an oxygen atom, wherein said heterocyclic group may be substituted by a lower alkyl group or a phenyl-lower alkyl group, or a salt thereof.

6. The benzazepine compound according to claim 3, wherein $R^2$ and $R^3$ are the same or different, and each are a hydrogen atom, a lower alkoxy group, a lower alkyl group which may have a lower alkoxy substituent, a hydroxy-substituted lower alkyl group, an amino-substituted lower alkyl group which may have a lower alkyl substituent, a carbamoyl-substituted lower alkyl group, a thiazolyl group, a phenoxy-lower alkyl group, a pyridyl group, a pyridyl-lower alkyl group, an imidazolyl-lower alkyl group, or an imidazolyl group which may have a lower alkyl substituent, or a salt thereof.

7. The benzazepine compound according to claim 3, wherein $R^2$ and $R^3$ combine together with the nitrogen atom to which they bond to form a 5- to 7-membered saturated heterocyclic group which may be intervened or not with another nitrogen atom or an oxygen atom, wherein said heterocyclic group may be substituted by a lower alkyl group or a phenyl-lower alkyl group, or a salt thereof.

8. The benzazepine compound according to claim 4, wherein $R^5$ is a group of the formula: —NHR⁶ (R⁶ is a lower alkyl group), or a salt thereof.

9. The benzazepine compound according to claim 4, wherein $R^5$ is a pyrrolidinyl group, or a salt thereof.

10. The benzazepine compound according to claim 5, wherein $R^5$ is a group of the formula: —NHR⁶ (R⁶ is a lower alkyl group), or a salt thereof.

11. The benzazepine compound according to claim 5, wherein $R^5$ is a pyrrolidinyl group, or a salt thereof.

12. The benzazepine compound according to claim 6, wherein $R^5$ is a group of the formula: —NHR⁶ (R⁶ is a lower alkyl group), or a salt thereof.

13. The benzazepine compound according to claim 6, wherein $R^5$ is a pyrrolidinyl group, or a salt thereof.

14. The benzazepine compound according to claim 7, wherein $R^5$ is a group of the formula: —NHR⁶ (R⁶ is a lower alkyl group), or a salt thereof.

15. The benzazepine compound according to claim 7, wherein $R^5$ is a pyrrolidinyl group, or a salt thereof.

16. 5-Isopropylaminocarbonylmethyl-1-[4-(1-pyrrolidinyl)-2-chlorobenzoyl]-2,3,4,5-tetrahydro-1H-benzazepine.

17. (5S)-5-Isopropylaminocarbonylmethyl-1-[4-(1-pyrrolidinyl)-2-chlorobenzoyl]-2,3,4,5-tetrahydro-1H-benzazepine.

18. (5R)-5-Isopropylaminocarbonylmethyl-1-[4-(1-pyrrolidinyl)-2-chlorobenzoyl]-2,3,4,5-tetrahydro-1H-benzazepine.

19. A process for preparing an optical active benzazepine compound of the formula [1b]:

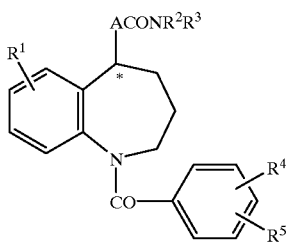

wherein R¹ is a hydrogen atom or a halogen atom,
A is lower alkylene group,
R² and R³ are the same or different and each are a hydrogen atom, a lower alkoxy group, a lower alkyl group which may have a lower alkoxy substituent, a hydroxy-substituted lower alkyl group, an amino-substituted lower alkyl group which may have a lower alkyl substituent, a carbamoyl-substituted lower alkyl group, a thiazolyl group, a phenoxy-lower alkyl group, a pyridyl group, a pyridyl-lower alkyl group, an imidazolyl-lower alkyl group, or imidazolyl group which may have a lower alkyl substituent, or R² or R³ may combine together with the nitrogen atom to which they bond to form a 5- to 7-membered saturated heterocyclic group which may be intervened or not with another nitrogen atom or an oxygen atom, wherein said heterocyclic group may be substituted by a lower alkyl group or a phenyl-lower alkyl group,
R⁴ is a hydrogen atom, a lower alkyl group, a hydroxy group, an amino group which may have a lower alkanoyl substituent, a nitro group, a halogen atom or a lower alkoxy group, and
R⁵ is a group of the formula: —NHR⁶ (wherein R⁶ is a lower alkyl group) or a pyrrolidinyl group, or a salt thereof, which comprises reacting a compound of the formula [2a]:

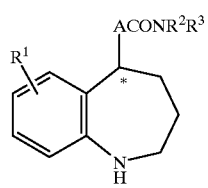

provided that when r⁵ is a pyrrolidinyl group, R² and R³ should not be a lower alkoxy group or an amino-substituted lower alkyl group which may have a lower alkyl substituent, wherein R¹, R², R³ and A are the same as defined above, with a compound of the formula [3]:

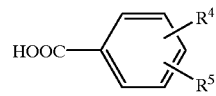

wherein R⁴ and R⁵ are the same as defined above, by a conventional amido bond producing reaction, and if necessary, followed by converting the product into a salt thereof.

20. A pharmaceutical composition which comprises as an active ingredient a therapeutically effective amount of the compound of claim 1, or a salt thereof, in admixture with a pharmaceutically acceptable carrier or diluent.

21. A method of agonizing vasopressin, which comprises administering to a warm-blooded animal including a human being a therapeutically effective amount of the compound of claim 1, or a pharmaceutically acceptable salt thereof.

22. A method of treatment of pollakisuria, diabetes, insipidus, urine incontinence, enuresis, nocturnal enuresis, spontaneous hemorrhage, hemophilia, von Willebrand's disease, uremia, congenital and acquired platelet dysfinction, hemostatic derangement caused by surgical procedures or accidental trauma or hepatocirrhosis, which comprises administering to a warm-blooded animal being a therapeutically effective amount of the compound of claim 1, or a pharmaceutically acceptable salt thereof.

23. The benzazepine compound according to claim 1, wherein R² is a hydrogen atom, a lower alkyl group which may have a lower alkoxy substituent, a hydroxy-substituted lower alkyl group, a thiazolyl group, a phenoxy-lower alkyl group, a pyridyl group, a pyridyl-lower alkyl group, or a imidazolyl-lower alkyl group, and R³ is a lower alkyl group having a lower alkoxy substituent, a hydroxy-substituted lower alkyl group, a thiazolyl group, a phenoxy-lower alkyl group, a pyridyl group, a pyridyl-lower alkyl group, or an imidazolyl-lower alkyl group, or a salt thereof.

24. The benzazepine compound according to claim 1 wherein R² and R³ are the same or different and are each a hydrogen atom or a lower alkyl group, R⁴ is a hydrogen atom, or a halogen atom, and R⁵ is a pyrrolidinyl group, or a salt thereof.

* * * * *

UNITED STATES PATENT AND TRADEMARK OFFICE
CERTIFICATE OF CORRECTION

PATENT NO.   : 6,096,736
DATED        : August 01, 2000
INVENTORS    : Hidenori OGAWA et al.

It is certified that errors appear in the above-identified patent and that said Letters Patent is hereby corrected as shown below:

In Claim 19, column 118, line 1, "$r^5$" should read --$R^5$--.

In Claim 22, column 118, line 29, "dysfinction" should read --dysfunction--.

Signed and Sealed this

Tenth Day of April, 2001

Attest:

NICHOLAS P. GODICI

*Attesting Officer*    *Acting Director of the United States Patent and Trademark Office*